United States Patent
Platzek et al.

(10) Patent No.: US 7,226,578 B2
(45) Date of Patent: *Jun. 5, 2007

(54) METAL COMPLEXES THAT CONTAIN PERFLUOROALKYL, PROCESS FOR THEIR PRODUCTION AND THEIR USE IN NMR DIAGNOSIS

(75) Inventors: Johannes Platzek, Berlin (DE); Ulrich Niedballa, Berlin (DE); Bernd Radüchel, Berlin (DE); Wolfgang Schlecker, Berlin (DE); Hanns-Joachim Weinmann, Berlin (DE); Thomas Frenzel, Berlin (DE); Bernd Misselwitz, Berlin (DE); Wolfgang Ebert, Berlin (DE)

(73) Assignee: Shering aG, Berlin (DE)

( * ) Notice: Subject to any disclaimer, the term of this patent is extended or adjusted under 35 U.S.C. 154(b) by 138 days.

This patent is subject to a terminal disclaimer.

(21) Appl. No.: 10/957,628

(22) Filed: Oct. 5, 2004

(65) Prior Publication Data

US 2005/0147563 A1    Jul. 7, 2005

Related U.S. Application Data

(60) Division of application No. 10/197,421, filed on Jul. 18, 2002, now Pat. No. 6,916,461, which is a division of application No. 09/435,918, filed on Nov. 8, 1999, now Pat. No. 6,468,502, which is a continuation of application No. 08/784,381, filed on Jan. 17, 1997, now abandoned.

(60) Provisional application No. 60/012,505, filed on Feb. 29, 1996.

(30) Foreign Application Priority Data

Jan. 19, 1996   (DE) ................................ 196 03 033

(51) Int. Cl.
    A61B 5/055         (2006.01)
(52) U.S. Cl. ............... 424/9.36; 424/9.361; 424/9.363; 424/9.365; 424/1.65; 424/9.4; 424/1.11
(58) Field of Classification Search ............... 424/1.11, 424/1.65, 9.1, 9.3, 9.36, 9.361, 9.363, 9.364, 424/9.365, 9.4, 9.5
See application file for complete search history.

(56) References Cited

U.S. PATENT DOCUMENTS

| | | | |
|---|---|---|---|
| 4,859,584 A | 8/1989 | Horan et al. | |
| 5,248,498 A | 9/1993 | Neumann et al. | |
| 5,302,370 A | 4/1994 | Neumeier et al. | |
| 5,401,493 A | 3/1995 | Lohrmann et al. | |
| 5,536,491 A | 7/1996 | Asai et al. | |
| 5,672,334 A | 9/1997 | Ranney | |
| 5,690,909 A | 11/1997 | Platzek et al. | |
| 6,019,959 A * | 2/2000 | Platzek et al. | 424/9.36 |
| 6,447,749 B1 * | 9/2002 | Licha et al. | 424/9.1 |
| 6,461,587 B1 * | 10/2002 | Platzek et al. | 424/9.323 |
| 6,468,502 B1 * | 10/2002 | Platzek et al. | 424/1.65 |
| 6,641,797 B2 * | 11/2003 | Platzek et al. | 424/1.65 |
| 6,676,928 B2 * | 1/2004 | Platzek et al. | 424/9.363 |
| 6,818,203 B2 * | 11/2004 | Platzek et al. | 424/9.363 |
| 6,916,461 B2 * | 7/2005 | Platzek et al. | 424/9.36 |

FOREIGN PATENT DOCUMENTS

| | | |
|---|---|---|
| DE | 43 17 588 | 12/1994 |
| EP | 0 266 195 | 10/1987 |
| EP | 0 266 196 | 10/1987 |
| EP | 0 592 306 | 4/1994 |

OTHER PUBLICATIONS

Gong et al., *Magn. Reson Imaging*, vol. 9, No. 1 (1991) pp. 101-106: "Paramater Optimization and Calibration of Fluorine-19 Magnetic Resonance Imaging at 1.5 Tesla".
Lee et al., *J. Magn. Reson Imaging*, vol. 4, No. 4 (1994), pp. 609-613: "In Vivo Fluorine-19 MR Imaging: Relaxation Enhancement with Gd-DTPA".
Ratner et al., *Invest. Radiol.*, vol. 24, No. 3 (1989), pp. 224-227: "Fluorine-19 Relaxation Rate Enhancement and Frequency Shift with Gadolinium-DTPA".
Thomas et al., *J. Magn. Reson Imaging*, vol. 4, No. 4 (1994), pp. 631-635: "Evaluation of the Influence of the Aqueous Phase Bioconstituent Environment on the F-19 T1 of Perfluorocarbon Blood Substitute Emulsions".
International Search Report, Norwegian, Nov. 14, 2001.

* cited by examiner

*Primary Examiner*—Dameron L. Jones
(74) *Attorney, Agent, or Firm*—Millen, White, Zelano & Branigan, P.C.

(57) ABSTRACT

The invention relates to new, monomeric, perfluoroalkyl-substituted metal complexes, processes for their production, and their use in diagnosis and therapy.

The compounds according to the invention are suitable especially as in vivo contrast media in nuclear spin tomography (MRT). They can preferably be used as blood-pool agents and as lymphographic agents.

5 Claims, 2 Drawing Sheets

MR Imaging before and after instititial administratio nof 10 μ of Gd/Kg
Gd-D03A-γ-aminoamide-perfluorooctylether T¹-weighted spin echo sequence (TR 400/TE 15)
Guinea Pigs, Injection Site: Intedigital space of the hind paw (on one side)
Arrow: Popliteally and inguinally profound lymph nodes of the injected side

METAL COMPLEXES THAT CONTAIN PERFLUOROALKYL, PROCESS FOR THEIR PRODUCTION AND THEIR USE IN NMR DIAGNOSIS

This application is a divisional of Ser. No. 10/197,421, filed on Jul. 18, 2002, now U.S. Pat. No. 6,916,461, issued Jul. 12, 2005, which is a divisional of Ser. No. 09/435,918, filed Nov. 8, 1999, now U.S. Pat. No. 6,468,502, issued Oct. 22, 2002, which is a continuation of non-provisional application Ser. No. 08/784,381, filed Jan. 17, 1997, now abandoned, and claims benefit of provisional application No. 60/012,505, filed Feb. 29, 1996.

The invention relates to the objects characterized in the claims, i.e., new, monomeric, perfluoroalkyl-substituted, paramagnetic metal complexes and complex salts, pharmaceutical agents containing these metal complexes, processes for their production, and their use as contrast media in $^1$H-NMR diagnosis and $^1$H-NMR spectroscopy, diagnostic radiology, and radiodiagnosis and as radiotherapeutic agents.

Nuclear magnetic resonance (NMR) is now a very extensively used method of medical diagnosis, used for in vivo imaging, with which vessels of the body and body tissue (including tumors) can be visualized by measuring the magnetic properties of the protons in the body water. To this end, e.g., contrast media are used that produce contrast enhancement in the resulting images or make these images readable by influencing specific NMR parameters of the body protons (e.g., relaxation times $T^1$ and $T^2$). Mainly complexes of paramagnetic ions, such as, e.g., gadolinium-containing complexes (e.g., Magnevist$^{(R)}$) are used owing to the effect of the paramagnetic ions on the shortening of the relaxation times. A measure of the shortening of the relaxation time is relaxivity, which is indicated in $mM^{-1} \cdot sec^{-1}$.

Paramagnetic ions, such as, e.g., $Gd^{3+}$, $Mn^{2+}$, $Cr^{3+}$, $Fe^{3+}$ and $Cu^{2+}$ cannot be administered in free form as solutions since they are too toxic. To make these ions suitable for in vivo use, they are generally complexed, which is described for the first time in EP 0 071 564 A1 (complexing with aminopolycarboxylic acids, e.g., with diethylenetriaminepentaacetic acid [DTPA]). The di-N-methylglucamine salt of the Gd-DTPA complex is known under the name Magnevist$^{(R)}$ and is used, i.a., to diagnose tumors in the human brain and in the kidney.

The meglumine salt of Gd-DOTA (gadolinium(III) complex of 1,4,7,10-tetracarboxymethyl-1,4,7,10-tetraazacyclododecane) that is described in French Patent 25 39 996 is another contrast medium that has demonstrated its value in nuclear spin tomography and was registered under the name Dotarem$^{(R)}$.

These contrast media cannot be used, however, in a satisfactory manner for all applications. Thus, the contrast media used clinically at present for the modern imaging processes of nuclear spin tomography (MRI) and computer tomography (CT), such as, e.g., Magnevist$^{(R)}$, Pro Hance$^{(R)}$, Ultravist$^{(R)}$ and Omniscan$^{(R)}$, are dispersed into the entire extracellular space of the body (in the intravascular space and in the interstice).

Contrast media that also are dispersed exclusively in the latter when administered in the vascular space and thus label it (so-called blood-pool agents) are especially desirable, however, to visualize vessels.

An attempt was made to solve these problems by using complexing agents, which are bound to macromolecules or biomolecules. Up until now, this has had very limited success.

Thus, for example, the number of paramagnetic centers in the complexes that are described in EP 0 088 695 A1 and EP 0 150 844 A1 is inadequate for satisfactory imaging.

If the number of required metal ions is increased by repeatedly introducing complexing units into a macromolecular biomolecule, this is associated with an intolerable impairment of the affinity and/or specificity of this biomolecule [J. Nucl. Med. 24, 1158 (1983)].

Macromolecular contrast media for angiography, such as albumin-Gd-DTPA, are described in Radiology 1987; 162: 205. Twenty-four hours after intravenous injection in rats, however, albumin-Gd-DTPA shows a concentration in the liver tissue that amounts to almost 30% of the dose. In addition, only 20% of the dose is eliminated within 24 hours.

The macromolecule polylysine-Gd-DTPA (EP 0 233 619 A1) can also be used as a blood-pool agent. For production reasons, however, this compound consists of a mixture of molecules of various sizes. In excretion tests in rats, it was shown that this macromolecule is excreted unaltered by glomerular filtration via the kidney. For synthesis reasons, it contains polylysine-Gd-DTPA but also macromolecules that are so large that they cannot pass through the capillaries of the kidney in the case of glomerular filtration and thus remain in the body.

Macromolecular contrast media based on carbohydrates, e.g., dextran, have also been described (EP 0 326 226 A1). The drawback of these compounds lies in the fact that the latter generally have only about 5% of the signal-enhancing paramagnetic cation.

The object of the invention was therefore to make available new $^1$H-NMR contrast media that do not exhibit the above-mentioned drawbacks and especially show a higher proton relaxivity and thus allow a reduction of the dose with increased signal intensity. The contrast media are also to be stable, well compatible and mainly exhibit organ-specific properties, whereby, on the one hand, their retention in the organs to be studied is to be sufficient to obtain the number of images that is necessary for an unambiguous diagnosis at low dosage, but, on the other hand, an excretion of metals from the body that is as fast as possible and very largely complete is then to be ensured.

The object of the invention is achieved with the monomeric, perfluoroalkyl-containing compounds of general formula I which show a surprisingly high proton relaxivity of 20-50 [$M^{-1}$ sec$^{-1}$, 39° C., 0.47 T].

These compounds are of the formula I

in which $R^F$ is a perfluorinated, straight-chain or branched carbon chain with formula $-C_nF_{2n}X$, in which X represents a terminal fluorine, chlorine, bromine, iodine or hydrogen atom, and n is 4-30, L means a direct bond, a methylene group, an —NHCO group, or a group

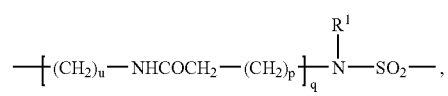

whereby p means numbers 0 to 10, q and u, independently of one another, mean numbers 0 or 1 and $R^1$ is a hydrogen atom, a methyl group, a —$CH_2$—OH group, a —$CH_2$—$CO_2$H group or a $C_2$-$C_{15}$ chain, which optionally is interrupted by 1 to 3 oxygen atoms, 1 to 2 CO groups or an optionally substituted aryl group and/or is substituted with 1 to 4 hydroxyl groups, 1 to 2 $C_1$-$C_4$ alkoxy groups, 1 to 2 carboxy groups, a group —$SO_3H$, or L is a straight-chain, branched, saturated or unsaturated $C_2$-$C_{30}$ carbon chain, which optionally contains 1 to 10 oxygen atoms, 1 to 3 —$NR^1$ groups, 1 to 2 sulfur atoms, , a piperazine, a —$CONR^1$ group, an —$SO_2$ group, an —$NR_1$—$CO_2$ group, 1 to 2 —CO groups, a group —CO—N—T—N($R^1$)—$SO_2$—$R^F$ or 1 to 2 optionally substituted aryls and/or is interrupted by these groups and/or is optionally substituted with 1 to 3 —$OR^1$ groups, 1 to 2 oxo groups, 1 to 2 —NH—$COR^1$ groups, 1 to 2 —CONHR groups, 1 to 2 —$(CH_2)_p$—$CO_2H$ groups, 1 to 2 groups of —$(CH_2)_p$—$(O)_q$—$CH_2CH_2$—$R^F$, whereby $R^1$, $R^F$ and p and q have the above-indicated meanings, and T means a $C_2$-$C_{10}$ chain, which optionally is interrupted by 1 to 2 oxygen atoms or 1 to 2 —NHCO groups, A stands for a complexing agent, metal complex, a salt of said complexing agent or metal complex with an organic and/or inorganic base or amino acid or amino acid amide, said complexing agent or complex having formula II

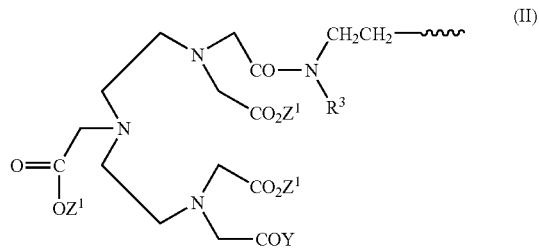

(II)

in which $R^3$, $Z^1$ and Y are independent of one another, and $R^3$ has the meaning of $R^1$ or means —$(CH_2)_m$—L—$R^F$, whereby m is 0, 1 or 2 and L and $R^F$ have the above-mentioned meaning, $Z^1$ independently of one another, mean a hydrogen atom or a metal ion equivalent of atomic numbers 21-29, 39, 42, 44 or 57-83, Y means —$OZ^1$ or

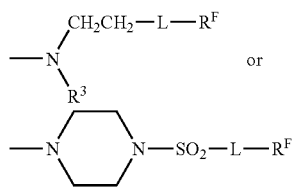

or whereby $Z^1$, L, $R^F$ and $R^3$ have the above-mentioned meanings, or said complexing agent or complex having formula III

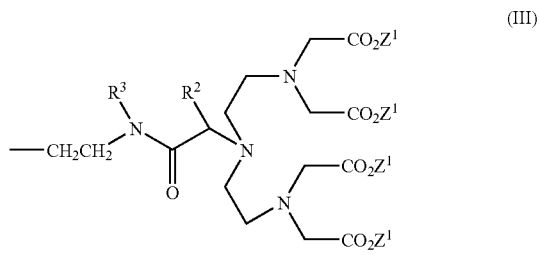

(III)

in which $R^3$ and $Z^1$ have the above-mentioned meanings and $R^2$ has the meaning of $R^1$, or said complexing agent or complex having formula IV

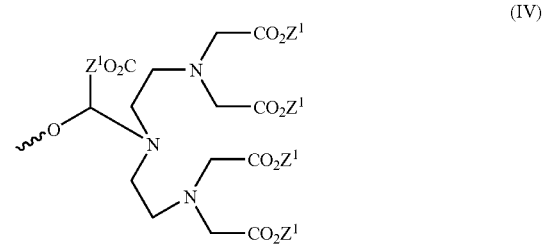

(IV)

in which $Z^1$ has the above-mentioned meaning, or said complexing agent or complex having formula V

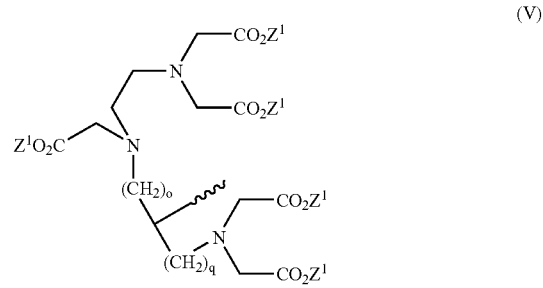

(V)

in which $Z^1$ has the above-mentioned meaning, and o and q stand for numbers 0 or 1 and the sum o+q=1 results, or said complexing agent or complex having formula VI

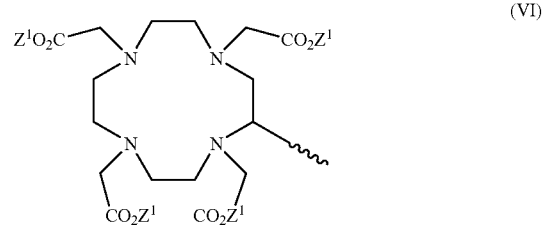

(VI)

in which $Z^1$ has the above-mentioned meaning or said complexing agent or complex having formula VII

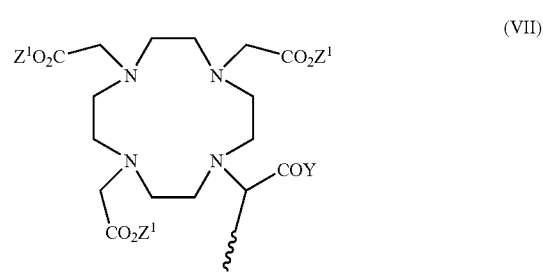

(VII)

in which $Z^1$ and Y have the above-mentioned meanings or
said complexing agent or complex having formula VIII

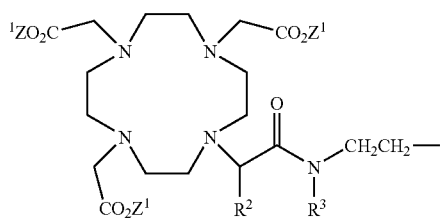
(VIII)

in which $R^3$ and $Z^1$ have the above-mentioned meanings, and $R^2$ has the above-mentioned meaning of $R^1$, or
said complexing agent or complex having formula IX

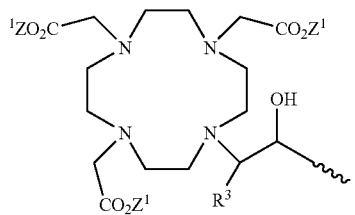
(IX)

in which $R^3$ and $Z^1$ have the above-mentioned meanings, or
said complexing agent or complex having formula X

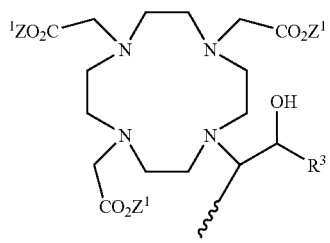
(X)

in which $R^3$ and $Z^1$ have the above-mentioned meanings, or
said for a complexing agent or complex having formula XI

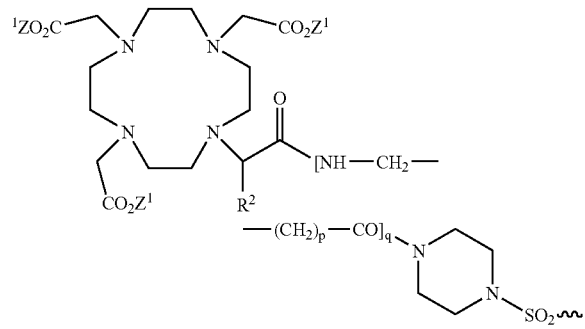
(XI)

in which $Z^1$, p and q have the above-mentioned meaning and $R^2$ has the meaning of $R^1$, or
said complexing agent or complex having formula XII

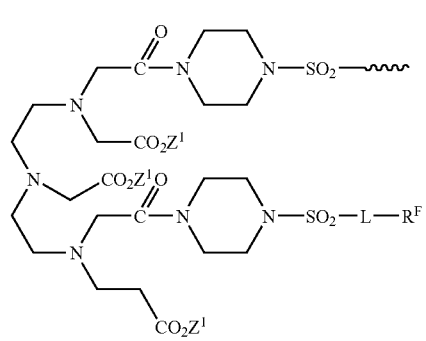
(XII)

in which L, $R^F$ and $Z^1$ have the above-mentioned meanings, or
said complexing agent or complex having formula XIII

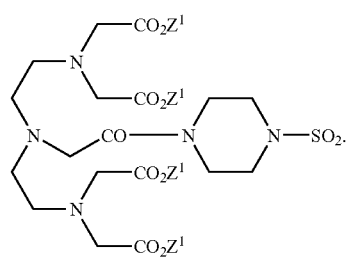
(XIII)

In addition, the compounds according to the invention are extremely well suited for detecting and locating vascular diseases, since they are also exclusively dispersed in the latter when administered in the intravascular space. The compounds according to the invention make it possible to distinguish tissue that is well-supplied with blood from tissue that is poorly supplied with blood with the aid of nuclear spin tomography and thus to diagnose an ischemia. Infarcted tissue can also be delimited from surrounding healthy or ischemic tissue due to its anemia, if the contrast media according to the invention are used. This is of special importance if the point is, e.g., to distinguish a myocardial infarction from an ischemia.

Compared to the macromolecular compounds that were previously used as blood-pool agents, such as, for example, Gd-DTPA polylysine, the compounds according to the invention also show a higher $T^1$ relaxivity (see Tab. 3) and are thus distinguished by a large increase in signal intensity in the case of NMR imaging. Since, in addition, they have an extended retention in the blood space, they can also be administered in relatively small dosages (of, e.g., $\leq 50$ μmol of Gd/kg of body weight). Mainly, however, the compounds according to the invention, none of which are polymeric compounds, are eliminated quickly and almost completely from the body.

It was also shown that the compounds of this invention are suitable not only as blood-pool agents, but are also excellent lymph-specific MRT contrast media (lymphographic agents).

The visualization of the lymph nodes is of vital importance for early detection of metastatic invasions in cancer patients. The contrast media according to the invention allow small metastases in non-enlarged lymph nodes (<2 cm) to be distinguished from lymph node hyperplasias without malignant invasions. In this case, the contrast media can be administered intravascularly or interstitially/intracutaneously. Interstitial/intracutaneous administration has the advantage that the substance is transported directly from the scattering concentrate table (e.g., primary tumor) via the corresponding lymph tracts into the potentially affected regional lymph node stations. Likewise, a high concentration of contrast medium in the lymph nodes can be achieved with a small dose.

The compounds according to the invention meet all requirements that are called for by contrast media in indirect MRT lymphography: good local compatibility, quick elimination of injection site, quick and very largely complete elimination from the entire organism. They also show a high concentration over several lymph node stations and thus make it possible to make relevant diagnostic statements. Thus, in the guinea pig model, it was possible to show a high concentration over several lymph node stations (popliteal, inguinal, iliac) after s.c. administration (2.5-10 μmol/kg of body weight, injection in the interdigital spaces of the hind paw). In especially suitable cases, gadolinium concentrations of respectively $\geq 200$ or $\geq 300$ μmol/l were obtained in the second (inguinal) and third (iliac) stations. Usually, lymph node concentration in the range of 100 to 1000 μmol/l can be obtained with the compounds according to the invention.

It was possible to confirm the special suitability of the compounds according to the invention in MR imaging studies in guinea pigs. Thus, 120 minutes after subcutaneous administration of 10 μmol/kg of body weight of a perfluorine-containing gadolinium complex (guinea pigs, hind paw, interdigital space) in $T^1$-weighted spin-echo images (TR 400 ms, TE 15 ms), a clear enhancement of the popliteal lymph nodes (270%) as well as the inguinal lymph nodes (104%) was observed (cf. Image 1).

In humans, the compounds according to the invention can be injected locally (either subcutaneously or directly percutaneously in the tissue of interest). Several injection sites (weals) with a respective injection volume of 0.2 to 1 ml are grouped around the areas of interest (e.g., tumor). In this case, the injected total volume should not in any case exceed 5 ml. This means that in the formulation, a metal concentration of 75-100 mmol/l must be present, so that a potential clinical dose of 5-10 μmol/kg of body weight can be administered with this volume. The site of administration thereof depends on whether a specific lymph outflow field from the tissue corresponding to it is to be specifically stained (e.g., in the case of gynecological or rectal tumors), or whether the unknown outflow field of a certain lesion (ergo the area for a possible therapeutic intervention, e.g., with melanoma or carcinoma of the breast) is to be visualized.

In normal lymph node tissue, where the concentration of the compound occurs, gadolinium concentrations of at least 50 μmol/l and at most 2500 μmol/l are required for MR imaging. The imaging can be carried out (depending on injection site and tissue) after 30 minutes or up to 4-6 hours after injection of the compounds according to the invention. Since mainly the $T^1$ relaxation times of the protons of the water of the lymph node tissue are influenced with the compounds of gadolinium complexes according to the invention, $T^1$-weighted sequences are best able to identify an MRT enhancement of the lymph node stations. Since lymph nodes very frequently are embedded in fatty tissue, and the latter has a very high signal intensity in such sequences, fat-suppressed measuring methods suggest themselves. Paramagnetic gadolinium complexes in combination with fat-suppressed, $T^1$-weighted measuring sequences have the great advantage, compared to the formulations of superparamagnetic iron oxide particles, that they allow MRT images with greater spatial resolution, with fewer distortion artifacts (based on susceptibility artifacts) and with shorter imaging time.

Since positive labeling of the lymph nodes occurs (i.e., signal rise), MRT images without contrast media for comparison are also no longer absolutely necessary, and the total examination time per patient can be shortened.

The new perfluoroalkyl-containing compounds of general formula I of claim 1 according to the invention comprise both complexing agents and metal complexes. Compounds of general formula I with $Z^1$ as hydrogen atom are referred to as complexing agents and compounds with at least one of possible substituents $Z^1$ as metal ion equivalent are referred to as metal complexes.

The compounds of general formula I according to the invention contain, as preferred radical L, the following:

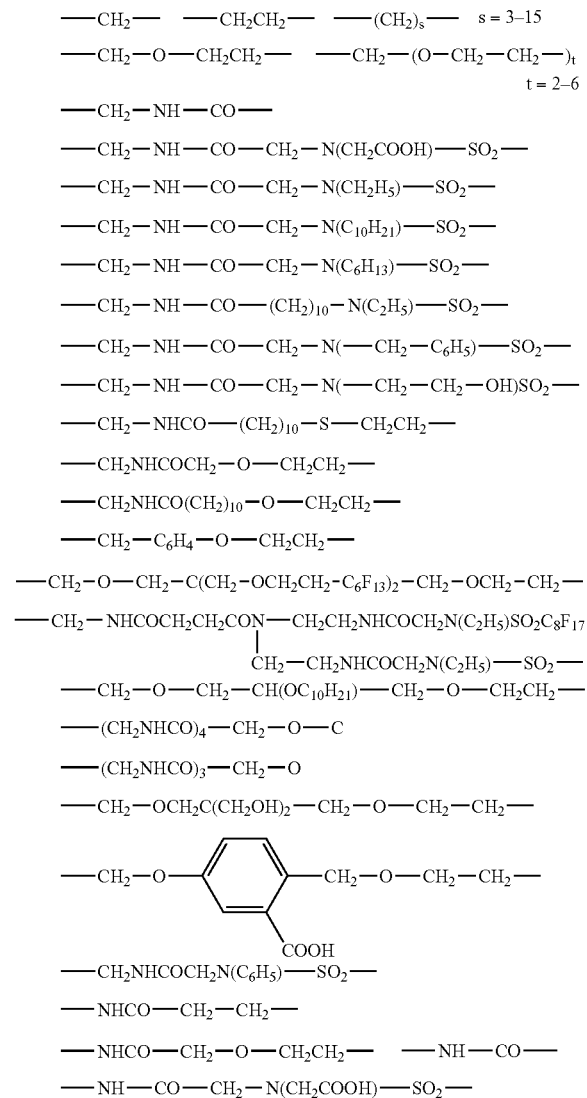

-continued

—NH—CO—CH$_2$—N(C$_2$H$_5$)—SO$_2$—

—NH—CO—CH$_2$—N(C$_{10}$H$_{21}$)—SO$_2$—

—NH—CO—CH$_2$—N(C$_6$H$_{13}$)—SO$_2$—

—NH—CO—(CH$_2$)$_{10}$—N(C$_2$H$_5$)—SO$_2$—

—NH—CO—CH$_2$—N(—CH$_2$—C$_6$H$_5$)—SO$_2$—

—NH—CO—CH$_2$—N(—CH$_2$—CH$_2$—OH)SO$_2$—

—NH—CO—CH$_2$—

—CH$_2$—O—C$_6$H$_4$—O—CH$_2$—CH$_2$—

—CH$_2$—C$_6$H$_4$—O—CH$_2$—CH$_2$—

—N(C$_2$H$_5$)—SO$_2$—  —N(C$_6$H$_5$)—SO$_2$—

—N(C$_{10}$H$_{21}$)—SO$_2$—  —N(C$_6$H$_{13}$)—SO$_2$—

—N(C$_2$H$_4$OH)—SO$_2$—  —N(CH$_2$COOH)—SO$_2$—

—N(CH$_2$—C$_6$H$_5$)—SO$_2$—

—N[CH(CH$_2$OH)$_2$]—SO$_2$—

—N[CH(CH$_2$OH)—CH(CH$_2$OH)]—SO$_2$—

According to the invention, radicals L of the compounds mentioned in the examples of this description of the invention are quite especially preferred.

Other preferred compounds are those in which X of the formula —C$_n$F$_{2n}$X means fluorine, and n stands for the numbers 4 to 15.

Compounds of general formula I with A in the meaning of general formula IX, whereby L contains at least one —NHCO group, can be obtained from compounds of general formula 14

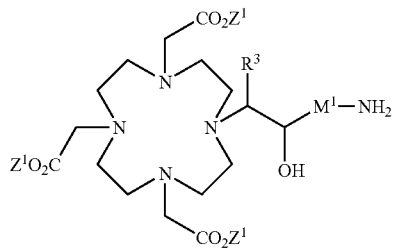

(14)

in which
R$^3$ is in the above-mentioned meaning, Z$^1$ is in the meaning of a metal ion equivalent of atomic numbers 21-29, 39, 42, 44 or 57-83, and
M$^1$ is in the meaning of L, by reaction with compounds of general formula 15

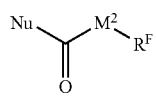

(15)

in which
R$^F$ has the above-mentioned meaning,
M$^2$ is in the meaning of L and
Nu is in the meaning of a nucleofuge.

Advantageously used as nucleofuges are the radicals:
Cl, F, —OTs, —OMs,

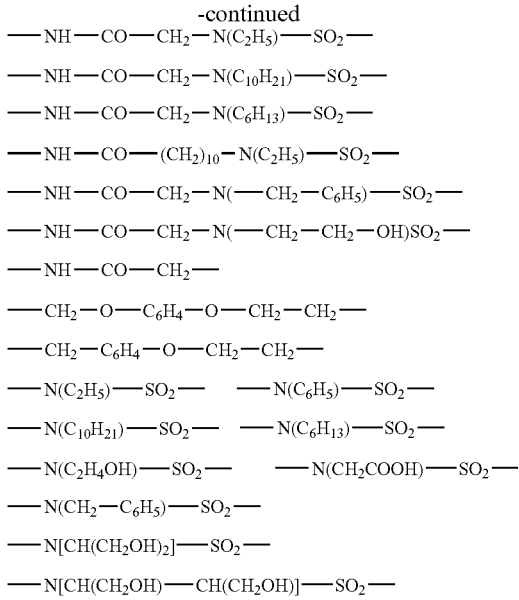

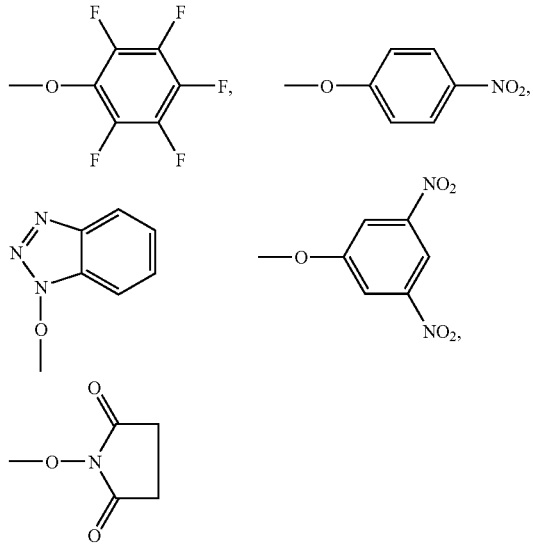

The reaction is carried out in a mixture of water and organic solvents such as: isopropanol, ethanol, methanol, butanol, dioxane, tetrahydrofuran, dimethylformamide, dimethylacetamide, formamide or dichloromethane. Preferred are ternary mixtures consisting of water, isopropanol and dichloromethane.

The reaction is carried out at a temperature interval between −10° C.-100° C., preferably between 0° C.-30° C.

As acid traps, inorganic and organic bases such as triethylamine, pyridine, N-methylmorpholine, diisopropylethylamine, dimethylaminopyridine, alkali and alkaline-earth hydroxides, their carbonates or bicarbonates such as lithium hydroxide, sodium hydroxide, potassium hydroxide, sodium carbonate, sodium bicarbonate, potassium bicarbonate are used.

The compounds of general formula 15 are obtained from compounds of general formula 16

$$HO_2C—M^2—R^F \quad (16)$$

in which
R$^F$, M$^2$ have the above-mentioned meaning, according to the processes of acid activation that are generally known to one skilled in the art, such as by reaction of the acid with dicyclohexylcarbodiimide, N-hydroxysuccinimide/dicyclohexylcarbodiimide, carbonyldiimidazole, 2-ethoxy-1-ethoxycarbonyl-1,2-dihydroquinoline, oxalic acid dichloride or isobutyl chloroformate according to the processes described in the literature:

Aktivierung von Carbonsäuren [Activation of Carboxylic Acids]. Übersicht in Houben-Weyl, Methoden der Organischen Chemie [Survey in Houben-Weyl, Methods of Organic Chemistry], Volume XV/2, Georg Thieme Verlag Stuttgart, 19.

Aktivierung mit Carbodiimiden [Activation with Carbodiimides]. R. Schwyzer and H. Kappeler, Helv. 46: 1550 (1963).

E. Wünsch et al., Volume 100: 173 (1967).

Aktivierung mit Carbodiimiden/Hydroxysuccinimid [Activation with Carbodiimides/Hydroxysuccinimide]: J. Am. Chem. Soc. 86: 1839 (1964) as well as J. Org. Chem. 53: 3583 (1988). Synthesis 453 (1972).

Anhydridmethode, 2-Ethoxy-1-ethoxycarbonyl-1,2-dihydrochinolin [Anhydride Method, 2-Ethoxy-1-ethoxycarbonyl-1,2-dihydroquinoline]: B. Belleau et al., J. Am. Chem. Soc., 90: 1651 (1986), H. Kunz et al., Int. J. Pept. Prot. Res., 26: 493 (1985) and J. R. Voughn, Am. Soc. 73: 3547 (1951).

Imidazolid-Methode [Imidazolide Method]: B. F. Gisin, R. B. Menifield, D. C. Tosteon, Am. Soc. 91: 2691 (1969).

Säurechlorid-Methoden, Thionylchlorid [Acid Chloride Methods, Thionyl Chloride]: Helv., 42: 1653 (1959).

Oxalylchlorid [Oxalyl Chloride]: J. Org. Chem., 29: 843 (1964).

The compounds of general formula 16 are commercially available products (Fluorochem, ABCR) or are obtained from compounds of general formula 17

$$H-Q-M^3-R^F \quad (17)$$

with
  $M^3$ in the meaning of L and
  Q in the meaning of oxygen, sulfur, a >CO group, >N—$R^3$, $R^3$—N—$SO_2$ with a bonding of a nitrogen atom to a hydrogen atom,
by reaction with compounds of general formula 18

$$Hal-CH_2-\underset{\underset{O}{\|}}{C}-OR^4 \quad (18)$$

with
  Hal meaning Cl, Br, I and
  $R^4$ meaning H, methyl, ethyl, t-butyl, benzyl, isopropyl, represented, for example, according to C. F. Ward, Soc. 121, 1161 (1922), according to the methods known to one skilled in the art, such as alkylation of alcohols with alkyl halides [Houben-Weyl, Methoden der Organischen Chemie, Sauerstoffverbindungen [Oxygen Compounds] I, Part 3, Methoden zur Herstellung und Umwandlung von Ethern (Methods for the Production and Conversion of Ethers], Georg Thieme Verlag, Stuttgart 1965, Alkylierung von Alkoholen mit Alkylhalogeniden [Alkylation of Alcohols with Alkyl Halides], p. 24, Alkylierung von Alkoholen mit Alkylsulfaten [Alkylation of Alcohols with Alkyl Sulfates] p. 33or N-Alkylierung eines Sulfonamids mit Alkylsulfonaten [N-Alkylation of a Sulfonamide with Alkylsulfonates] (Houben-Weyl, Methoden der organischen Chemie, XI/2 Stickstoffverbindungen [XI/2 Nitrogen Compounds], Georg Thieme Verlag Stuttgart, 1957, p. 680; J. E. Rickman and T. Atkins, Am. Chem. Soc., 96: 2268, 1974, 96: 2268; F. Chavez and A. D. Sherry, J. Org. Chem. 1989, 54: 2990].

If Q means a >CO group, the reaction is performed with a Wittig reagent of the structure $$(Ar)_3 \overset{+}{P}-\overset{-}{C}H-(CH_2)_r-CO_2R^4,$$

whereby r means numbers 0-16.

The —CH=CH double bond that is produced in this case can remain as a component of the structure or be converted to a —$CH_2$—$CH_2$ group by catalytic hydrogenation (Pd 5%/C).

The compounds of general formula 18 are commercially available products (Fluorochem, ABCR).

As an alternative, compounds of general formula I with A in the meaning of general formula IX can be obtained from compounds of general formula 19

(19)

with
  $R^F$, $R^3$ and $R^4$ in the above-mentioned meaning and
  L' in the meaning of L, optionally with protected hydroxyl or carboxyl functions, by, if necessary, protective groups that are present being cleaved and the thus obtained complexing agents being reacted with metal oxides or metal salts at room temperature or elevated temperature with the methods known according to one skilled in the art (EP 250358, EP 255471), and then—if desired—acid hydrogen atoms that are present being substituted by cations of inorganic and/or organic bases, amino acids or amino acid amides.

The compounds of general formula 19 are obtained from compounds of general formula 20 (D03A or the esters)

(20)

with
  $R^4$ in the above-mentioned meaning by reaction with compounds of general formula 21

(21)

in which
  $R^3$ has the meaning of $R^1$, optionally in protected form, or —$(CH_2)_m$—L"$R^F$, whereby m is 0, 1 or 2, and L' and $R^F$ have the above-mentioned meaning. The reaction is carried out in alcohols such as methanol, ethanol, isopropanol, butanol, ethers such as dioxane, tetrahydrofuran, dimethoxy ethers or in water or in mixtures of water and one of the mentioned organic solvents, as well as also acetonitrile, acetone, dimethylformamide, dimethylacetamide or dimethyl sulfoxide, dichloromethane, dichloroethane, chloroform at temperatures between −10° C. and 180° C., preferably at 20°-100° C. The addition of organic or inorganic bases, such as triethylamine, pyridine, dimethylaminopyridine, N-methylmorpholine, diisopropylamine, alkali or alkaline-earth hydroxides or their carbonates or bicarbonates such as lithium hydroxide, sodium hydroxide, potassium hydroxide, sodium carbonate, potassium carbonate, sodium bicarbonate, potassium bicarbonate has proven advantageous. In the case of low-boiling epoxides, the reaction is carried out in an autoclave.

The compounds of general formula 21 are commercially available products (Fluorochem, ABCR) or can be obtained from compounds of general formula 22

$$R^3-CH=CH-L'-R^F \quad (22)$$

by epoxidation according to the methods known to one skilled in the art, for example, the wolframate-catalyzed oxidation with $H_2O_2$ according to Payne, the cyclization of halohydrins or the alkaline $H_2O_2$ oxidation in the presence of nitrites.

Especially suitable for this reaction is 3-chloroperbenzoic acid in dichloromethane at room temperature. Houben-Weyl, Methoden der Organischen Chemie, Sauerstoffverbindungen I, Part 3, Methoden zur Herstellung und Umwandlung dreigliedriger cyclische Ether (1,2-Epoxide) [Methods for the Production and Conversion of Three-Membered Cyclic Ethers (1,2-Epoxides)], Georg Thieme Verlag, Stuttgart, 1965; G. B. Payne and P. H. Williams, J. Org. Chem., 159, 24: 54; Y. Ogata and Y. Samaki, Tetrahedron 1964, 20: 2065; K. B. Sharpless et al., Pure Appl. Chem. 55, 589 (1983).

Compounds of general formula 22 are preferably obtained by Wittig reaction, or by the variants according to Horner, Schlosser or Bestmann, Houben-Weyl, Methoden der Organischen Chemie XII/1, Organische Phosphorverbindungen Teil 1 [Organic Phosphorus Compounds Part 1], Georg Thieme Verlag, Stuttgart, 1963, Phosphoniumsalze [Phosphonium Salts] p. 79, Phosphoniumylide [Phosphonium Ylides] p. 112, Wittig Reaction p. 121; A. W. Johnson, Ylides and Imines of Phosphorus, John Wiley & Sons, Inc., New York, Chichester, Brisbane, Toronto, Singapore, 1993, Wittig Reaction p. 221; Schlosser-Modifikation der Wittig-Reaktion [Schlosser Modification of the Wittig Reaction] p. 240; Wadsworth-Emmons-Reaktion [Wadsworth-Emmons Reaction] p. 313; Horner Reaktion [Horner Reaction] p. 362, by reaction of a triarylphosphonium ylide

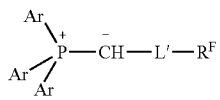

(23)

with L' and $R^F$ in the above-mentioned meaning and Ar meaning aryl, especially phenyl, with commercially available methods (Merck, Fluka) or according to the methods known to one skilled in the art, for example, oxidation of primary alcohols with chromium trioxide/pyridine, Houben-Weyl, Methoden der organischen Chemie, Sauerstoffverbindungen II, Part 1, Aldehyde [Aldehydes], Georg Thieme Verlag, Stuttgart, 1954, aldehydes of general formula 20 that can be produced

$$OHC-R^3 \quad (24)$$

whereby
$R^3$ can also be H.

Triarylphosphonium ylides 23 are produced from the corresponding halides of general formula 25

$$Hal-CH_2-L'-R^F \quad (25)$$

with Hal, L' and $R^F$ in the above-mentioned meaning according to the methods known to one skilled in the art, for example by heating the triarylphosphine with the alkylhalide, Houben-Weyl, Methoden der Organischen Chemie XII/1, Organische Phosphorverbindungen Teil 1, Georg Thieme Verlag, Stuttgart, 1963 or A. W. Johnson, Ylides and Imines of Phosphorus, John Wiley & Sons, Inc., New York, Chichester, Brisbane, Toronto, Singapore, 1993. The compounds of general formula 25 are commercially available products (Fluorochem, ABCR, 3M).

The compounds of general formula 21 with $R^3=H$ are preferably obtained from compounds of general formula 17

$$H-Q'-M^3-R^F \quad (17)$$

in which
Q' is in the meaning of Q, but cannot mean any >CO group,
$M^3$ has the meaning of L with the exception of the direct bond and
$R^F$ has the above-mentioned meaning, by reaction according to the way of etherification or sulfonamidealkylation with epihalohydrins that is known to one skilled in the art: (Houben-Weyl, Methoden der Organischen Chemie, Sauerstoffverbindungen I, Part 3, Methoden zur Herstellung und Umwandlung von Ethern, Georg Thieme Verlag, Stuttgart, 1965, Alkylierung von Alkoholen [Alkylation of Alcohols], p. 24, 33; Houben-Weyl, Methoden der Organischen Chemie, XI/2 Stickstoffverbindungen, Georg Thieme Verlag, Stuttgart, 1957, p. 680; J. E. Rickman and T. J. J. Atkins, Am. Chem. Soc. 1974, 96: 2268; F. Chavez and A. D. Sherry, 1989, 54: 2990) of general formula 26

(26)

with
Hal' in the meaning of Hal, F, —OTs, OMs.

In the case of low-boiling epoxides, the reaction is carried out in an autoclave.

Compounds of general formula I with A in the meaning of general formula VIII are obtained from compounds of general formula 27

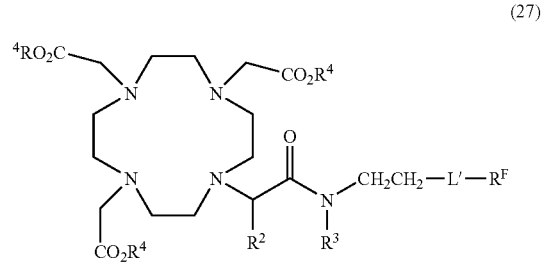

(27)

with $R^2$, $R^3$, $R^4$, L' and $R^F$ in the above-mentioned meaning, by cleavage of optionally present protective groups and complexing in the way known to one skilled in the art.

Compounds of general formula 27 are obtained by alkylation of the compounds of general formula 20 with compounds of general formula 28

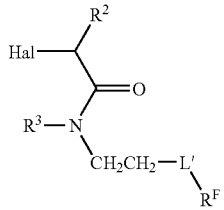

(28)

in which Hal, $R^2$, $R^3$, L' and $R^F$ have the above-mentioned meaning, in a way known in the art, for example as described under EP 0 232 751 B1 (Squibb).

Compounds of general formula 28 are produced from compounds of general formula 29

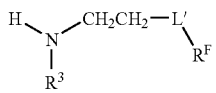

(29)

with L', $R^3$ and $R^F$ in the above-mentioned meaning and an activated halocarboxylic acid of general formula 30

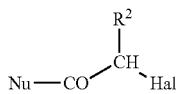

(30)

with Nu, $R^2$ and Hal in the above-mentioned meaning according to the methods of amide formation via activated carboxylic acids that are known to one skilled in the art [cf. Lit. p. 11].

Compounds of general formula 30 can be obtained from the acids according to C. Hell, Vol. 14: 891 (1881); J. Volhard, A 242, 141 (1887); N. Zelinsky, Vol. 20: 2026, (1887) or from the haloacids according to the activation methods as they are described in general formula 15.

The compounds of general formula 29 can be easily produced according to the methods of amine synthesis that are known to one skilled in the art [Houben-Weyl, Methoden der Organischen Chemie, Stickstoffverbindungen II, Amino, 1st Run, Georg Thieme Verlag, Stuttgart, 1957] from the commercially available compounds (Fluorochem, ABCR) of general formula 31

Hal—CH$_2$CH$_2$—L'—R$^F$ (31)

or 32

HO—CH$_2$CH$_2$—L'—R$^F$ (32)

for example, by alkylation of a compound 31 with an amine PhCH$_2$NHR$^3$ and subsequent deprotection of the amino group by catalytic hydrogenation or by Mitsunobu reaction [H. Loibner and E. Zbiral, Helv. 59, 2100 (1976), A. K. Bose and B. Lal, Tetrahedron Lett. 3973 (1973)] of a compound 32 with potassium phthalimide and deprotection with hydrazine hydrate.

Compounds of general formula I with A in the meaning of general formula VII are obtained from compounds of general formula 33

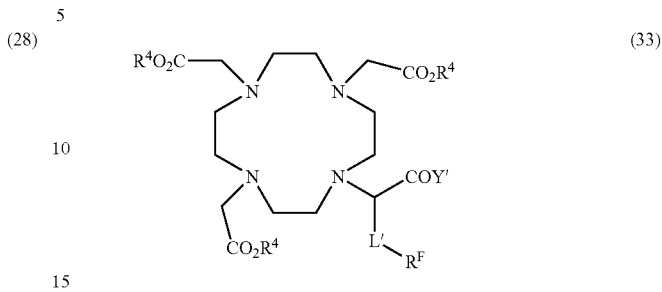

(33)

with

L', $R^F$ and $R^4$ in the above-mentioned meaning and
Y' in the meaning of Y, optionally with protective groups, by cleavage of optionally present protective groups and complexing according to the methods that are known to one skilled in the art (Protective Groups in Organic Synthesis, 2nd Edition, T. W. Greene and P. G. M. Wuts, John Wiley & Sons, Inc., New York, 1991; EP 0 130 934, EP 0 250 358).

Compounds of general formula 33 are obtained from compounds of general formula 20 and compounds of general formula 34

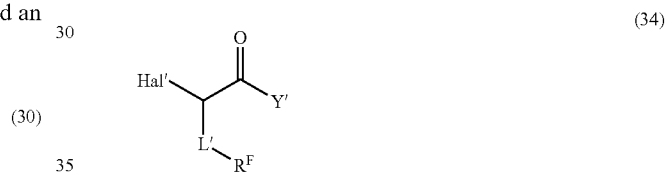

(34)

in which

Hal', L', $R^F$ have the above-mentioned meaning and Y' stands for the radical

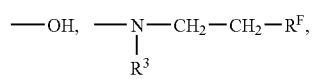

in a way known in the art, for example as described in EP 0 232 751 B1, EP 0 292 689 A2 (both Squibb) or EP 0 255 471 A1 (Schering).

The production of compounds of general formula 34 is carried out according to known methods, for examples according to Hell-Volhard-Zelinsky from commercially available precursors (ABCR).

Compounds of general formula I with A in the meaning of general formula VI are obtained from compounds of general formula 35

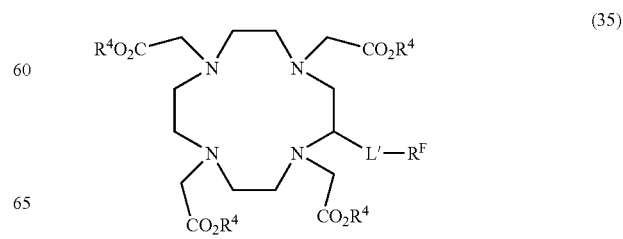

(35)

in which L', R⁴ and R^F have the above-mentioned meaning, by, if appropriate, cleavage of protective groups and complexing in a way known in the art [Protective Groups in Organic Synthesis, 2nd edition, T. W. Greene and P. G. M. Wuts, John Wiley & Sons, Inc., New York, 1991 (EP 0 130 934, EP 0 250 358)].

Compounds of general formula 35 are obtained by reacting α-halocarboxylic acid esters or α-halocarboxylic acids of general formula 18 with compounds of general formula 36

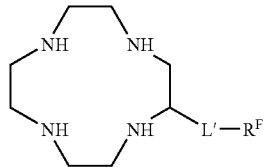
(36)

with L' and R^F in the above-mentioned meaning, according to the methods that are known to one skilled in the art, as described, for example, in EP 0 255 471 or U.S. Pat. No. 4,885,363.

Compounds of general formula 36 can be obtained by cleavage of optionally present protective groups and subsequent reduction with diborane according to the known processes from compounds of general formula 37

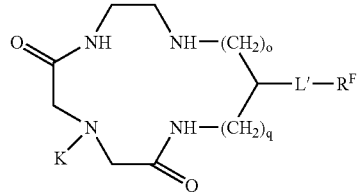
(37)

in which
L', R^F, o, q, have the above-mentioned meaning and
K has the meaning of a protective group.

The compounds of general formula 37 are available by a condensation reaction from an activated, N-protected iminodiacetic acid 38 and amine 39:

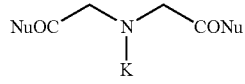
(38)

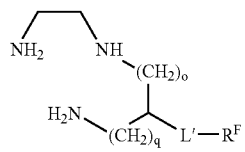
(39)

in which
L', R^F, o, q, Nu and K have the abovementioned meaning. As nucleofuge, preferably the N-hydroxysuccinimide is used; as protective group, the benzyloxycarbonyl, trifluoroacetyl or t-butyloxycarbonyl group is used.

Compounds of general formula 38 can be obtained according to the processes of protecting the amino group and of activating carboxylic acid that are known to one skilled in the art [Protective Groups, Activation of Carboxyl Groups, p. 11] with protected iminodiacetic acid 40

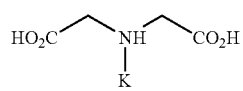
(40)

in which
K has the meaning of a protective group, from iminodiacetic acid 41

As an alternative, compounds of general formula 36 are available by, if appropriate, cleavage of protective groups and reduction with diborane according to the process described in 37

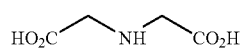
(41)

from compounds of general formula 42

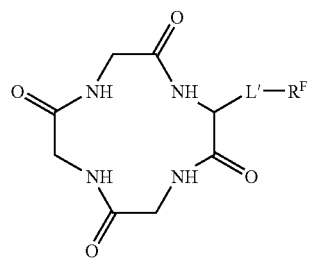
(42)

Compounds of general formula 42 can be obtained by closing the rings of Secco compounds 43

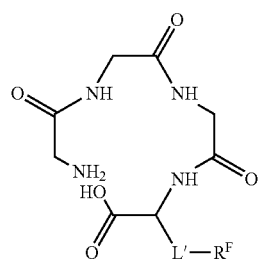
(43)

in which
L' and R^F have the above-mentioned meaning, according to standard processes; for example, by reaction with the Mukaiyama reagent 2-fluoro-1-methylpyridinium-tosylate

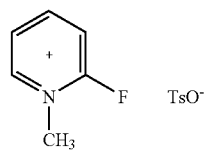

[J. Org. Chem. 1994, 59, 415; Synthetic Communications 1995, 25, 1401] or with the phosphoric acid diphenylesterazide

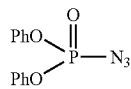

[J. Am. Chem. Soc. 1993, 115, 3420; WO 94/15925].

Compounds of general formula 43 are available according to the described processes by condensation of activated acid 44

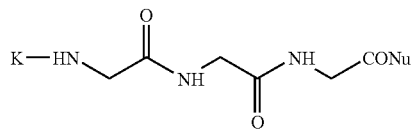
(44)

with Nu and K in the above-mentioned meaning, with a compound of general formula 45

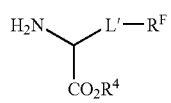
(45)

in which

L', $R^4$ and $R^F$ have the above-mentioned meaning.

Compounds of general formula 44 are available from commercially available triglycine (Bachem, Fluka) 46

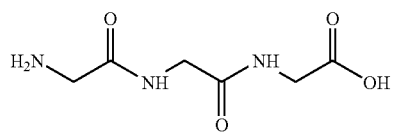
(46)

by protection of the amino group with subsequent activation of the acid function according to the processes for amine protection and carboxylic acid reactivation that are known to one skilled in the art (Lit. p. 12).

The compounds of general formula 45 can be easily obtained from compounds of general formula 62 by introducing protective group $R^4$ according to the methods known to one skilled in the art—for example, re-esterification of a sulfite ester.

Compounds of general formula I with A in the meaning of general formula II are obtained from compounds of general formula 47

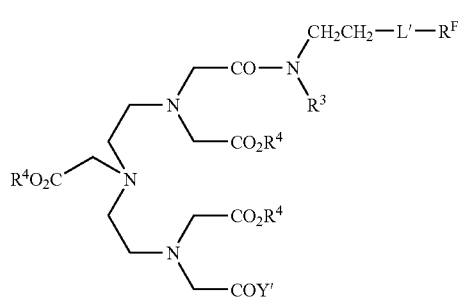
(47)

with L', $R^3$, $R^4$, $R^F$ and Y' in the above-mentioned meaning, by, if appropriate, cleavage of protective groups and complexing in a way that is well-known to one skilled in the art (Protective Groups, EP 0 250 358, EP 0 130 934).

If Y' in general formula 47 means an OH group, the compounds are obtained by reacting a compound 48

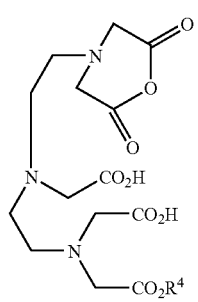
(48)

with $R^4$ in the above-mentioned meaning, produced according to DE 3 633 243, with an amine of general formula 29 under the conditions already described and subsequent cleavage of the protective groups.

If Y' in formula 47, however, is the group

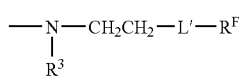

then the reaction is performed under analogous conditions with DTPA-bisanhydride (commercially available product, Merck) 49

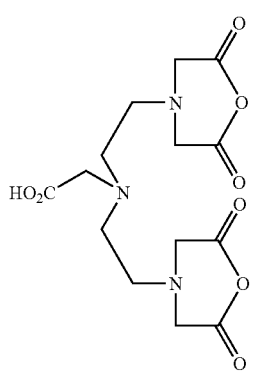
(49)

Compounds of general formula I, with A in the meaning of general formula III, are obtained from compounds of general formula 50

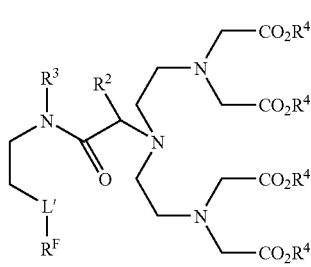
(50)

in which

L', $R^2$, $R^3$, $R^4$ and $R^F$ have the above-mentioned meaning, by, if appropriate, cleavage of protective groups and complexing in a way that is well-known to one skilled in the art [Protective Groups, EP 0 071564, EP 0 130 934, DE-OS 3 401 052].

Compounds of general formula 50 are obtained according to the process described in J. Org. Chem. 1993, 58: 1151 from compounds of general formula 51

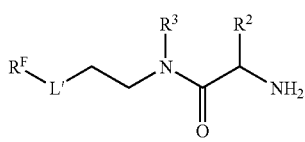

(51)

and halocarboxylic acid derivatives of formula 52

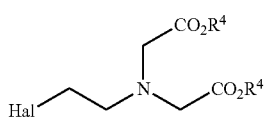

(52)

in which $R^4$ and Hal have the already described meaning. The compounds of general formula 51 are produced by acylation of an amine of general formula 29 with an activated N-protected amino acid of general formula 53

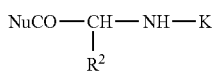

(53)

in which Nu has the above-mentioned meaning and K is in the meaning of a protective group such as Z, —BOC, FMOC, —COCF$_3$, and subsequent cleavage of the protective group.

Compounds of general formula I with A in the meaning of general formula IV are obtained from compounds of general formula 54

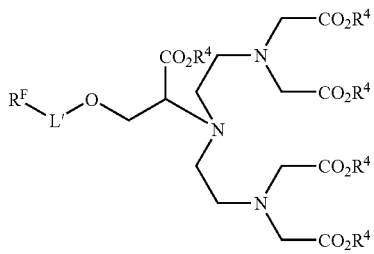

(54)

in which

L', $R^F$ and $R^4$ have the above-mentioned meaning, by, if appropriate, cleavage of the protective groups and completing according to a method that is known to one skilled in the art, as already described [Protective Groups, EP 0 071 564, EP 0 130 934, DE-OS 3 401 052].

Compounds of general formula 54 can be obtained in a known way from the halogen compounds of general formula 55

Hal—L'—$R^F$ (55)

that can be obtained as commercially available products (Fluorochem, ABCR) by reaction with hydroxy acids 56

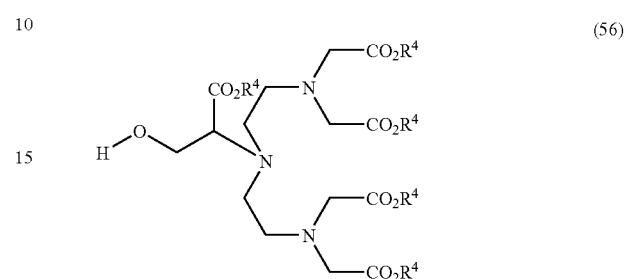

(56)

in which $R^4$ has the above-mentioned meaning. The compounds of formula 56 can be obtained in a way known in the art according to J. Org. Chem. 58, 1151 (1993) from commercially available serine ester 57 (Bachem, Fluka)

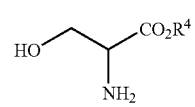

(57)

with $R^4$ in the above-mentioned meaning and halocarboxylic acid esters 58

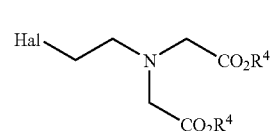

(58)

Compounds of general formula I with A in the meaning of general formula V are obtained from compounds of general formula 59

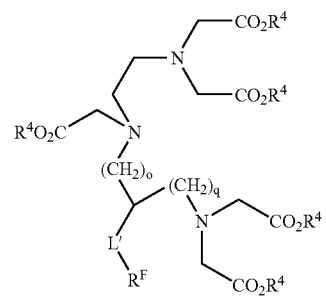

(59)

in which

L', o, q, $R^4$ and $R^F$ have the above-mentioned meaning, by, if appropriate, cleavage of protective groups and complexing according to a method that is known to one skilled in the art. [Protective Groups, EP 0 071 564, EP 0 130 934, DE-OS 3 401 052].

Compounds of general formula 59 can be produced in a known way, for example, according to J. Org. Chem., 58, 1151 (1993), by reaction of halocarboxylic acid esters 18

with Hal and $R^4$ in the above-mentioned meaning, and a compound of general formula 39

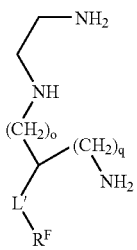

in which

L', o, q, and $R^F$ have the above-mentioned meaning.

The compounds of general formula 39 are obtained for the case q=0 from the compounds of general formula 60

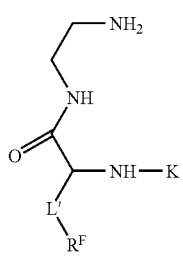

with

L', $R^F$ and K in the above-mentioned meaning, in a way known in the art [Helv. Chim. Acta, 77: 23 (1994)] by reduction with diborane and cleavage of the protective groups. The compounds of general formula 60 are obtained with ethylenediamine by aminolysis of the activated compounds of general formula 61

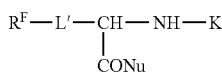

in which

L', Nu, $R^F$ and K have the above-mentioned meaning.

The compounds of general formula 61 are produced according to the known methods of protective group chemistry [Protective Groups] from the unprotected acid of general formula 62

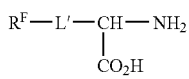

specifically the amino group is protected in a first step, followed by the activation of the acid group in the second step.

The compounds of general formula 62 can be produced according to the methods of amino acid synthesis [Houben-Weyl, Methoden der organischen Chemie, XI/2 Stickstoffverbindungen II and III, II Aminosäuren [II Amino Acids]; Georg Thieme Verlag Stuttgart, 1958, Strecker-Reaktion [Strecker Reaction], p. 305; Erlenmeyer-Reaktion [Erlenmeyer Reaction], p. 306; Aminolyse von α-Halogencarbonsäuren [Aminolysis of α-Halocarboxylic Acids], p. 309] from the commercially available aldehydes of general formula 63

for example, according to Strecker, via the azlactone or via the cyanohydrin.

The compounds of general formula 39 are obtained for the case o=0 from the compounds of general formula 64

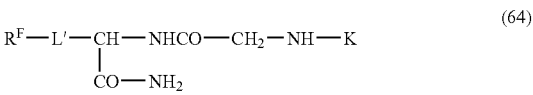

with $R^F$, L' and K in the mentioned meanings, in a way known in the art by cleavage of the protective groups and reduction with diborane.

Compounds of general formula 64 are available by aminolysis of N-protected activated glycines 53 with compounds of general formula 65

in which $R^F$ and L' have the mentioned meanings.

The compounds of general formula 65 can be obtained in a simple way from compounds of general formula 61 by amide formation with ammonia and subsequent cleavage of the protective group.

Compounds of general formula XIII can be produced analogously to the compounds of general formula III, by halocarboxylic acid derivatives of general formula 52 being reacted with a compound of general formula 66

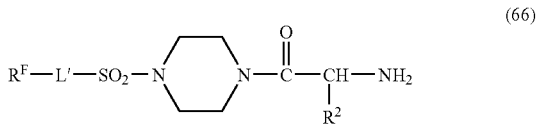

in which $R^F$, L' and $R^2$ have the above-mentioned meanings.

The compounds of general formula 66 are produced by reaction of a compound of general formula 67

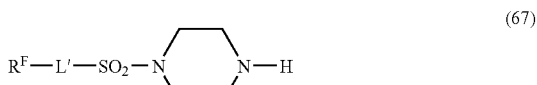

with the activated, N-protected amino acid of general formula 53 analogously to the reaction of amine 29 with compound 53.

The compounds of general formula 67 can be obtained by reaction of piperazine—freely or optionally partially protected—with perfluoroalkylsulfonic acid fluorides or -chlorides. (The sulfonamide formation from amine and sulfofluoride is described in DOS 2 118 190, DOS 2 153 270, both Bayer AG).

Compounds of general formula XI with q meaning the numbers 0 or 1 are produced analogously to compounds of general formula VIII, by compounds of general formula 20 being reacted with compounds of general formula 68

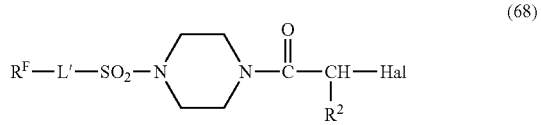

(68)

in which $R^F$, L', $R^2$ and Hal have the above-mentioned meaning or being reacted with compounds of general formula 68a

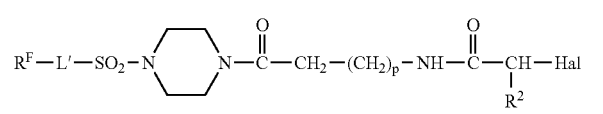

(68a)

in which $R^F$, L', $R^2$, p and Hal have the above-mentioned meanings.

Compounds of general formula 68 can be obtained from compounds of general formula 30 and piperazine derivatives of general formula 67 in a way known in the art.

Compounds of general formula XII are produced analogously to compounds of general formula II, e.g., by reaction of compounds of formula 49 with piperazine derivatives of general formula 67.

Compounds of general formula 68a are produced from compounds of general formula 67 by amide-coupling with compounds of general formula 68b

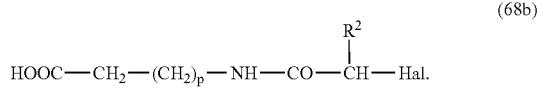

(68b)

Compounds of general formula I with A in the meaning of general formula X are obtained from compounds of general formula 69

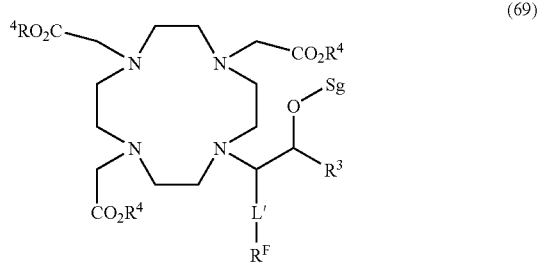

(69)

in which

41a

L', $R^3$, $R^4$ and $R^F$ have the above-described meaning and Sg is in the meaning of a protective group, by, if appropriate, cleavage of protective groups and complexing in a way known in the art [Protective Groups in Organic Synthesis, 2nd Edition, T. W. Greene and P. G. M. Wuts, John Wiley & Sons, Inc., New York, 1991 (EP 0 130 934, EP 0 250 358)].

Compounds of general formula 69 are obtained by reaction of α-halocarboxylic acid esters or α-halocarboxylic acids of general formula 18 with compounds of general formula 70

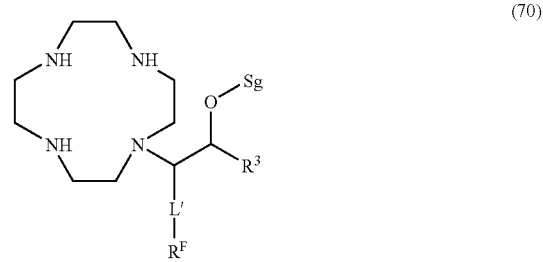

(70)

with L', $R^F$, $R^3$ and Sg in the above-mentioned meaning according to the methods that are known to one skilled in the art, as described, for example, in EP 0 255 471 or U.S. Pat. No. 4,885,363.

Compounds of general formula 70 can be obtained by cleavage of optionally present protective groups and subsequent reduction with diborane according to the known processes from compounds of general formula 71

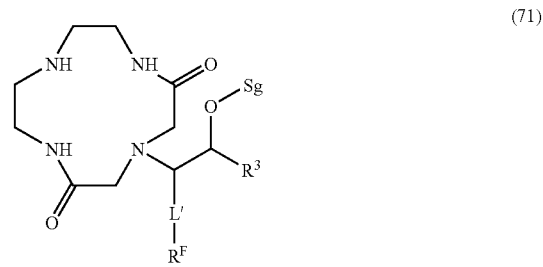

(71)

in which

L', $R^F$, $R^3$ and Sg have the above-mentioned meaning.

The compounds of general formula 71 can be obtained by a condensation reaction from an activated iminodiacetic acid derivative of general formula 72 and the diethylenetriamine of formula 73

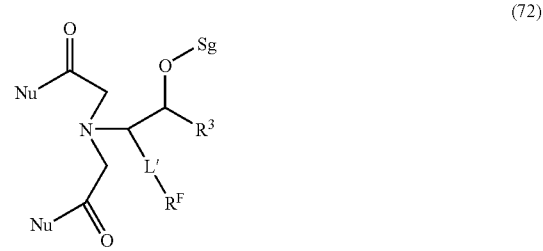

(72)

-continued

(73)
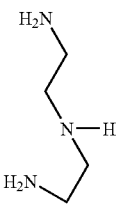

in which
L', $R^F$, $R^3$, Sg and Nu have the above-mentioned meaning.
N-Hydroxysuccinimide is preferably used as nucleofuge Nu.

Compounds of general formula 72 can be obtained from compounds of general formula 74

(74)
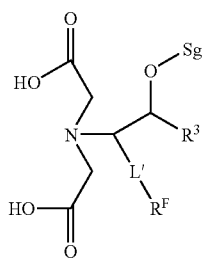

in which
L', $R^F$ and Sg have the above-mentioned meaning, by activation of carboxylic acids, as described oh page 11.

Compounds of general formula 74 are obtained by reaction of α-halocarboxylic acid esters or α-halocarboxylic acids of general formula 18 with compounds of general formula 75

(75)
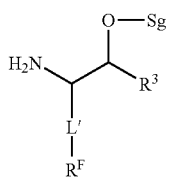

in which
L', $R^F$, $R^3$ and Sg have the above-mentioned meaning, whereby optionally present ester groups are saponified.

Compounds of general formula 75 are obtained from compounds of general formula 76

(76)
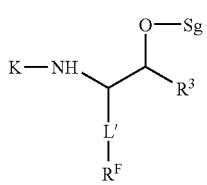

in which
L', $R^F$, $R^3$, Sg and K have the above-mentioned meaning, by cleavage of protective group K according to the known processes.

Compounds of general formula 76 are obtained from compounds of general formula 77

(77)
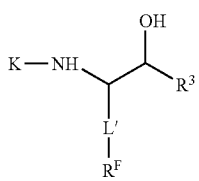

in which
L', $R^F$, $R^3$ and K have the above-mentioned meaning, by introduction of a protective group Sg in the way known to one skilled in the art.

Compounds of general formula 77 are obtained from the compounds of general formula 78

(78)
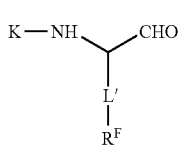

in which
L', $R^F$ and K have the above-mentioned meaning, according to the methods that are well-known to one skilled in the art (Houben-Weyl, Methoden der Organischen Chemie, XIII 2a, Metallorganische Verbindungen [Organometallic Compounds], Georg Thieme Verlag Stuttgart, 1973, p. 285 ff, Umsetzung magnesiumorganischer Verbindungen mit Aldehyden [Reaction of Magnesium-organic Compounds with Aldehydes]; p. 809 ff, Umsetzung von zinkorganischen Verbindungen mit Aldehyden [Reaction of Zinc-organic Compounds with Aldehydes]; Houben-Weyl, Methoden der Organischen Chemie XIII/1, Metallorganische Verbindungen, Georg Thieme Verlag Stuttgart, 1970; p. 175 ff, Umsetzung lithiumorganischer Verbindungen mit Aldehyden [Reaction of Lithium-organic Compounds with Aldehydes] by reaction with the organometallic compounds, such as magnesium, lithium or zinc compounds, that can be obtained from compounds of general formula 79

Hal—$R^3$ (79)

in which
Hal and $R^3$ have the above-mentioned meaning.

Compounds of general formula 79 are commercially available products (ABCR, Fluka).

Compounds of general formula 78 are produced from compounds of general formula 80

(80)
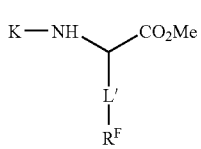

in which
L', $R^F$ and K have the above-mentioned meaning, by reduction with diisobutylaluminum hydride (Tett. Lett., 1962, 619; Tett. Lett., 1969, 1779; Synthesis, 1975, 617).

Compounds of general formula 80 are produced from compounds of general formula 45

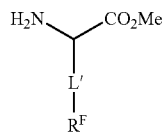

(45)

in which

L' and $R^F$ have the above-mentioned meaning, in a way known to one skilled in the art by introducing protective group K.

The neutralization of optionally still present free carboxy groups is done with the aid of inorganic bases (for example, hydroxides, carbonates or bicarbonates) of, for example, sodium, potassium, lithium, magnesium or calcium and/or organic bases such as, i.a., primary, secondary and tertiary amines, such as, for example, ethanolamine, morpholine, glucamine, N-methylglucamine and N,N-dimethylglucamine, as well as basic amino acids, such as, for example, lysine, arginine and ornithine or of amides of originally neutral or acidic amino acids.

To provide neutral complex compounds, enough of the desired bases can be added, for example, to the acid complex salts in aqueous solution or suspension to ensure that the neutral point is reached. The solution obtained can then be evaporated to dryness in a vacuum. Often, it is advantageous to precipitate the neutral salts formed by adding water-miscible solvents, such as, for example, lower alcohols (methanol, ethanol, isopropanol and others), lower ketones (acetone and others), polar ethers (tetrahydrofuran, dioxane, 1,2-dimethoxyethane and others) and to obtain easily isolated and readily purified crystallizates. It has proven especially advantageous to add the desired base as early as during the complexing of the reaction mixture and thus to save a process step.

Pharmaceutical agents that contain at least one physiologically compatible compound of general formula I, optionally with the additives that are commonly used in galenicals, are also the object of the invention.

The production of the pharmaceutical agents according to the invention is carried out in a way known in the art, by the complex compounds according to the invention—optionally with the addition of the additives that are commonly used in galenicals—being suspended or dissolved in aqueous medium and then the suspension or solution optionally being sterilized. Suitable additives are, for example, physiologically harmless buffers (such as, for example, tromethamine), additives of complexing agents or weak complexes (such as, for example, diethylenetriaminepentaacetic acid or the Ca complexes that correspond to the metal complexes according to the invention) or—if necessary—electrolytes, such as, for example, sodium chloride or—if necessary—antioxidants such as, for example, ascorbic acid.

If suspensions or solutions of the agents according, to the invention in water or physiological salt solution are desired for enteral or parenteral administration or other purposes, they are mixed with one or more adjuvant(s) that are commonly used in galenicals (for example, methylcellulose, lactose, mannitol] and/or surfactant(s) [for example, lecithins, Tween[(R)], Myrj[(R)]] and/or flavoring substance(s) for taste correction [for example, ethereal oils].

In principle, it is also possible to produce the pharmaceutical agents according to the invention without isolating the complexes. In any case, special care must be used to undertake the chelation so that the complexes according to the invention are practically free from noncomplexed metal ions that have a toxic effect.

This can be ensured, for example, with the aid of color indicators such as xylenol orange by control titrations during the production process. The invention therefore also relates to the process for the production of complex compounds and their salts. As a final precaution, there remains purification of the isolated complex.

The pharmaceutical agents according to the invention preferably contain 0.1 µmol-1 mol/l of the complex and are generally dosed in amounts of 0.0001-5 mmol/kg. They are intended for enteral and parenteral administration. The complex compounds according to the invention are used 1. for NMR diagnosis and diagnostic radiology in the form of their complexes with the ions of elements with atomic numbers 21-29, 39, 42, 44 and 57-83;
2. for radiodiagnosis and radiotherapy in the form of their complexes with the radioisotopes of the elements with atomic numbers 27, 29, 31, 32, 37-39, 43, 49, 62, 64, 70, 75 and 77.

The agents according to the invention meet the varied requirements for suitability as contrast media for nuclear spin tomography. Thus, after oral or parenteral administration and by increasing the signal intensity, they are extremely well suited to improve in its informative value the image obtained with the aid of the nuclear spin tomograph. They also show the high effectiveness that is necessary to burden the body with the smallest possible amounts of foreign substances, and the good compatibility that is necessary to maintain the noninvasive nature of the studies.

The good water-solubility and low osmolality of the agents according to the invention make it possible to produce highly-concentrated solutions, thus to keep the volume burden of the circulatory system within justifiable limits and to offset the dilution by the bodily fluid. In addition, the agents according to the invention exhibit not only high stability in vitro, but also surprisingly high stability in vivo, so that a release or an exchange of the ions that are bound to the complexes—and toxic in themselves—is carried out only extremely slowly within the time in which the new contrast media are completely eliminated again.

In general, the agents according to the invention for use as NMR diagnostic agents are dosed in amounts of 0.0001-5 mmol/kg, preferably 0.005-0.5 mmol/kg. Especially low dosages (below 1 mg/kg of body weight) of organ-specific NMR diagnostic agents can be used, for example, for detecting tumors and myocardial infarctions.

The complex compounds according to the invention can also be used advantageously as susceptibility reagents and as shift reagents for in vivo NMR spectroscopy.

The agents according to the invention are also suitable as radiodiagnostic agents owing to their advantageous radioactive properties and the good stability of the complex compounds that are contained in them. Details of such use and dosage are described, e.g., in "Radiotracers for Medical Applications," CRC Press, Boca Raton, Fla.

The compounds and agents according to the invention can also be used in positron emission tomography, which uses positron-emitting isotopes such as, e.g., $^{43}$Sc, $^{44}$Sc, $^{52}$Fe, $^{55}$Co and $^{68}$Ga (Heiss, W. D.; Phelps, M. E.; Positron Emission Tomography of Brain, Springer Verlag Berlin, Heidelberg, New York 1983).

The compounds according to the invention are also suitable, surprisingly enough, for differentiating malignant and benign tumors in areas without blood-brain barriers.

They are also distinguished in that they are eliminated completely from the body and are thus well compatible.

Since the substances according to the invention accumulate in malignant tumors (no diffusion in healthy tissue, but high permeability of tumor vessels), they can also assist the radiation therapy of malignant tumors. The latter are distinguished from the corresponding diagnosis only by the amount and type of isotopes used. In this case, the aim is the destruction of tumor cells by high-energy shortwave radiation with as small a range of action as possible. For this purpose, interactions of the metals that are contained in the complexes (such as, e.g., iron or gadolinium) with ionizing radiations (e.g., x rays) or with neutron rays are employed. The local radiation dose at the site where the metal complex is located (e.g., in tumors), is significantly enhanced by this effect. To produce the same radiation dose in malignant tissue, the radiation exposure for healthy tissue can be considerably reduced and thus burdensome side effects for the patients can be avoided when such metal complexes are used. The metal complex conjugates according to the invention are therefore also suitable as radiosensitizing substances in the case of radiation therapy of malignant tumors (e.g., use of Mössbauer effects or in the case of neutron capture therapy). Suitable β-emitting ions are, for example, $^{46}$Sc, $^{47}$Sc, $^{48}$Sc, $^{72}$Ga, $^{73}$Ga and $^{90}$Y. Suitable α-emitting ions that exhibit short half-lives are, for example, $^{211}$Bi, $^{212}$Bi, $^{213}$Bi and $^{214}$Bi, whereby $^{212}$Bi is preferred. A suitable photon- and electron-emitting ion is $^{158}$Gd, which can be obtained from $^{157}$Gd by neutron capture.

If the agent according to the invention is specified for use in the variant of radiation therapy that is proposed by R. L. Mills et al. (Nature Vol. 336, (1988), p. 787], the central ion must be derived from a Mössbauer isotope, such as, for example, $^{57}$Fe or $^{151}$Eu.

In the case of in vivo administration of the agents according to the invention, the latter can be administered together with a suitable vehicle, such as, for example, serum or physiological common salt solution and together with another protein such as, for example, human serum albumin. In this case, the dosage is dependent on the type of cellular impairment, the metal ion used and the type of imaging method.

The agents according to the invention are usually administered parenterally, preferably i.v. They can also be administered—as already discussed—intravascularly or interstitially/intracutaneously, depending on how the vessels or tissue of the body are to be examined.

The agents according to the invention are extremely well suited as x-ray contrast media, in which case it is especially to be emphasized that with them, no signs of the anaphylaxis-like reactions that are known from the iodine-containing contrast media can be detected in biochemical-pharmacological studies. They are especially valuable because of the advantageous absorption properties in the ranges of higher tube voltages for digital substraction techniques.

In general, the agents according to the invention for use as x-ray contrast media are dosed, for example, analogously to meglumine-diatrizoate, in amounts of 0.1-5 mmol/kg, preferably 0.25-1 mmol/kg.

Taken overall, it has been possible to synthesize new complexing agents, metal complexes and metal complex salts to open up new possibilities in diagnostic and therapeutic medicine.

The following examples are used for a more detailed explanation of the object of the invention:

EXAMPLE 1 a) N-Ethyl-N-(perfluorooctylsulfonyl)-amino-acetic acid-t-butyl ester 20 g (37.94 mmol) of N-ethylperfluorooctylsulfonamide and 15.73 g (113.8 mmol) of potassium carbonate are suspended in 200 ml of acetone, and 14.80 g (75.87 mmol) of bromoacetic acid-tert-butyl ester is added in drops at 60° C. It is stirred for 3 hours at 60° C. The salts are filtered out, and the filtrate is evaporated to dryness in a vacuum. The residue is chromatographed on silica gel (mobile solvent: hexane/dichloromethane/acetone=10/10/1). After the product-containing fractions are concentrated by evaporation, the residue is recrystallized from methanol/ether.

Yield: 21.66 g (89% of theory) of a waxy colorless solid

Elementary analysis:

Cld: C, 29.96; H, 2.51; F, 50.36; N, 2.18; S, 5.00. Fnd: C, 29.81; H, 2.70; F, 50.15; N, 2.30; S, 4.83.

b) N-Ethyl-N-(perfluorooctylsulfonyl)-amino-acetic acid 20 g (31.18 mmol) of the title compound of Example 1a) is dissolved in 200 ml of trifluoroacetic acid and stirred overnight at room temperature. It is evaporated to dryness in a vacuum. The residue is recrystallized from methanol/ether.

Yield: 17.34 g (95% of theory) of a colorless crystalline solid

Elementary analysis:

Cld: C, 24.63; H, 1.38; F, 55.19; N, 2.39; S, 5.48. Fnd: C, 24.48; H, 1.50; F, 55.01; N, 2.17; S, 5.59.

c) Gadolinium Complex of 10-[2-hydroxy-4-aza-5-oxo-7-aza-7-(perfluorooctylsulfonyl)-nonyl]-1,4,7-tris(carboxymethyl)-1,4,7,10-tetraazacyclododecane 10 g (17.09 mmol) of the title compound of Example 1b) and 1.97 g (18.79 mmol) of N-hydroxysuccinimide are dissolved in a mixture of 50 ml of dimethylformamide/50 ml of chloroform. At 0° C., 3.88 g (18.79 mmol) of dicyclohexylcarbodiimide is added and stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of the gadolinium complex of 10-(3-amino-2-hydroxy-propyl)-1,4,7-tris(carboxymethyl)-1,4,7,10-tetraazacyclododecane (WO 95/17451), dissolved in 50 ml of water, is added and stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18/mobile solvent: gradient consisting of water/n-propanol/acetonitrile).

Yield: 16.37 g (78% of theory) of a colorless, vitreous solid

Water content: 7.1%

$T_1$-relaxivity (L/mmol·sec) at 20 MHz, 37° C.:

41 (water)

49 (human plasma)

Elementary analysis (relative to anhydrous substance):

Cld: C, 30.58; H, 3.18; F, 28.31; Gd 13.78; N, 7.37; S, 2.81. Fnd: C, 30.40; H, 3.29; F, 28.14; Gd 13.55; N, 7.28; S, 2.65.

d) 10-[2-Hydroxy-4-aza-5-oxo-7-aza-7-(perfluorooctylsulfonyl)-nonyl]-1,4,7-tris(carboxymethyl)-1,4,7,10-tetraazacyclododecane 10 g (8.76 mmol) of the title compound of Example 1c) is dissolved in a mixture of 100 ml of water/100 ml of ethanol, and 1.73 g (13.71 mmol) of oxalic acid-dihydrate is added. It is heated for 8 hours to 80° C. It is cooled to 0° C., and precipitated gadolinium oxalate is filtered out. The filtrate is evaporated to dryness, and the residue is purified on RP-18 (RP-18/mobile solvent: gradient consisting of water/i-propanol/acetonitrile).

Yield: 8.96 g (94% of theory) of a vitreous solid
Water content: 9.3%
Elementary analysis (relative to anhydrous substance):
Cld: C, 35.30; H, 3.98; F, 32.73; N, 8.52; S, 3.25. Fnd: C, 35.10; H, 4.15; F, 32.51; N, 8.35; S, 3.15.

e) Manganese Complex of 10-[2-hydroxy-4-aza-5-oxo-7-aza-7-(perfluorooctylsulfonyl)-nonyl]-1,4,7-tris(carboxymethyl)-1,4,7,10-tetraazacyclododecane (as sodium salt)

5 g (5.07 mmol) of the title compound of Example 1d) is dissolved in 100 ml of water, and 0.58 g (5.07 mmol) of manganese(II) carbonate is added. It is stirred for 3 hours at 80° C. The solution is filtered, and the filtrate is adjusted to pH, 7.2 with 1N sodium hydroxide solution, then it is freeze-dried.

Yield: 5.87 g (quantitative) of a colorless-amorphous powder
Water content: 8.4%
$T_1$-relaxivity (L/mmol·sec) at 20 MHz, 37° C.:
2.7 (water)
4.2 (human plasma)
Elementary analysis (relative to anhydrous substance):
Cld: C, 32.81; H, 3.42; F, 30.42; Mn 5.17; N, 7.92; Na 2.17; S, 3.02. Fnd: C, 32.62; H, 3.57; F, 30.21; Mn 5.06; N, 7.80; Na 2.01; S, 2.90.

f) Ytterbium Complex of 10-[2-hydroxy-4-aza-5-oxo-7-aza-7-(perfluorooctyl-sulfonyl)-nonyl]-1,4,7,-tris(carboxymethyl)-1,4,7,10-tetraazacyclododecane 1.33 g (2.53 mmol) of ytterbium carbonate is added to 5 g (5.07 mmol) of the title compound of Example 1d) in 100 ml of water/30 ml of ethanol, and it is stirred for 3 hours at 80° C.

The solution is filtered, and the filtrate is evaporated to dryness in a vacuum.

Yield: 6.36 g (quantitative) of a vitreous solid.
Water content: 7.8%.
Elementary analysis (relative to anhydrous substance):
Cld: C, 30.11; H, 3.14; F, 27.92; N, 7.27; S, 2.77; Yb 14.96. Fnd: C, 30.02; H, 3.27; F, 27.80; N, 7.10; S, 2.68; Yb 14.75.

g) Dysprosium Complex of 10-[2-hydroxy-4-aza-5-oxo-7-aza-7-(perfluorooctyl-sulfonyl)-nonyl]-1,4,7-tris(carboxymethyl)-1,4,7,10-tetraazacyclododecane 0.95 g (2.53 mmol) of dysprosium oxide is added to 5 g (5.07 mmol) of the title compound of Example 1d) in 100 ml of water/30 ml of ethanol, and it is stirred for 3 hours at 80° C. The solution is filtered, and the filtrate is evaporated to dryness in a vacuum.

Yield: 6.35 g (quantitative) of a colorless, vitreous solid.
Water content: 8.5%.

Elementary analysis (relative to anhydrous substance):
Cld: C, 30.39; H, 3.17; F, 28.18; N, 7.33; S, 2.80; Dy 14.18. Fnd: C, 30.17; H, 3.25; F, 28.03; N, 7.21; S, 2.65; Dy 14.00.

EXAMPLE 2 a) 13,13,13,12,12,11,11,10,10,9,9,8,8,7,7,6,6-Heptadecafluoro-3-oxatridecanoic acid-t-butyl ester 10.51 g (53.9 mmol) of bromoacetic acid-tert-butyl ester is added in drops to a mixture of 10 g (21.55 mmol) of 1H,1H,2H,2H-perfluorodecan-1-ol and 0.73 g (2.15 mmol) of tetrabutylammonium hydrogen sulfate in 100 ml of 60% potassium hydroxide solution/50 ml of toluene while being stirred vigorously at 0° C. It is stirred for 1 hour at 0° C. 200 ml of toluene is added, the aqueous phase is separated and extracted twice with 50 ml of toluene each. The combined organic phases are dried on magnesium sulfate and concentrated by evaporation in a vacuum. The residue is chromatographed on silica gel (mobile solvent: hexane/dichloromethane/acetone=20/10/1).

Yield: 9.72 g (78% of theory) of a colorless viscous oil
Elementary analysis:
Cld: C, 33.23; H, 2.61; F, 55.85. Fnd: C, 33.09; H, 2.78; F, 55.71.

b) 13,13,13,12,12,11,11,10,10,9,9,8,8,7,7,6,6-Heptadecafluoro-3-oxatridecanoic acid 9.0 g (15.56 mmol) of the title compound of Example 2a) is dissolved in 180 ml of trifluoroacetic acid and stirred overnight at room temperature. It is evaporated to dryness in a vacuum.

The residue is recrystallized from methanol/ether.
Yield: 7.80 g (96% of theory) of a colorless solid
Elementary analysis:
Cld: C, 27.60; H, 1.35; F, 61.85. Fnd: C, 27.48; H, 1.49; F, 61.66.

c) Gadolinium Complex of 10-[2-hydroxy-4-aza-5-oxo-7-oxa-10,10,11,11,12,12,13,13,14,14,15,15,16,16,17,17,17-heptadecafluoroheptadecyl]-1,4,7-tris(carboxymethyl)-1,4,7,10-tetraazacyclododecane 7.0 g (13.41 mmol) of the title compound of Example 2b) and 1.70 g (14.75 mmol) of N-hydroxysuccinimide are dissolved in a mixture of 30 ml of dimethylformamide/20 ml of chloroform. At 0° C., 3.04 g (14.75 mmol) of dicyclohexylcarbodiimide is added and stirred for 1 hour at 0° C., then for 3 hours at room temperature. It is cooled again to 0° C., and 4.48 g (44.25 mmol) of triethylamine/50 ml of 2-propanol is added. Then, 8.46 g (14.75 mmol) of the gadolinium complex of 10-(3-amino-2-hydroxy-propyl)-1,4,7-tris(carboxymethyl)-1,4,7,10-tetraazacyclododecane, dissolved in 40 ml of water, is added and stirred for 3 hours at room temperature. It is evaporated to dryness, the residue is taken up in a mixture of 100 ml of methanol/30 ml of chloroform, and dicyclohexylurea is filtered out. The filtrate is evaporated to dryness and purified by RP-chromatography (RP-18/mobile solvent: gradient consisting of water/n-propanol/acetonitrile).

Yield: 11.8 g (75% of theory) of a colorless, vitreous solid
Water content: 8.2%
$T_1$-relaxivity (L/mmol·sec) at 20 MHz, 37° C.:
19 (water)
33 (human plasma)

Elementary analysis:
Cld: C, 32.32; H, 3.27; F, 29.96; Gd 14.59; N, 6.50. Fnd: C, 32.16; H, 3.42; F, 29.78; Gd 14.39; N, 6.40.

EXAMPLE 3 a) 1,2-Epoxy-4-oxa-1H,1H,2H,3H,3H,5H,5H,6H,6H-perfluorotetradecane 7.97 g (86.18 mmol) of epichlorohydrin is added in drops to a mixture of 20 g (43.09 mmol) of 1H,1H,2H,2H-perfluorodecan-1-ol and 0.79 g (2.32 mmol) of tetrabutylammonium hydrogen sulfate in 200 ml of 60% potassium hydroxide solution/100 ml of toluene while being stirred vigorously at 10° C., and care is taken to ensure that the temperature of the reaction solution is not higher than 20° C. It is allowed to stir for 2 hours at 15° C., and then 3.99 g (43.09 mmol) of epichlorohydrin is added in drops as described above. Then, it is stirred overnight at room temperature. 100 ml of methyl-tert-butyl ether is added, and the aqueous phase is separated. The latter is extracted twice more with 50 ml of toluene each. The organic phases are combined, dried on magnesium sulfate and concentrated by evaporation in a vacuum. The residue is chromatographed on silica gel (mobile solvent: dichloromethane/hexane/acetone=20/10/1).

Yield: 19.05 g (85% of theory) of a colorless oil
Elementary analysis:
Cld: C, 30.02; H, 1.74; F, 62.09. Fnd: C, 29.87; H, 1.95; F, 61.81.

b) 10-[-2Hydroxy-4-oxa-1H,1H,2H,3H,3H,5H,5H,6H,6H-perfluorotetradecyl]-1,4,7-tris(carboxymethyl)-1,4,7,10-tetraazacyclododecane 8.3 g (207.6 mmol) of sodium hydroxide is added to 12.0 g (34.60 mmol) of 1,4,7-tris(carboxymethyl)-1,4,7,10-tetraazacyclododecane in 50 ml of water. A solution of 18.0 g (34.60 mmol) of the title compound of Example 3a), dissolved in 60 ml of n-butanol/60 ml of 2-propanol, is added dropwise to it, and the solution is heated overnight to 70° C. It is evaporated to dryness in a vacuum, the residue is taken up in 300 ml of water and adjusted to pH, 3 with 3N hydrochloric acid. Then, it is extracted twice with 200 ml of n-butanol. The combined butanol phases are evaporated to dryness in a vacuum, and the residue is purified by RP-chromatography (RP-18/mobile solvent: gradient consisting of water/n-butanol/acetonitrile).

Yield: 26.61 g (79% of theory)
Water content: 11.0%
Elementary analysis (relative to anhydrous substance):
Cld: C, 37.42; H, 4.07; F, 37.27; N, 6.47. Fnd: C, 37.25; H, 4.19; F, 37.08; N, 6.30.

c) Gadolinium complex of 10-[-2hydroxy-4-oxa-1H,1H,2H,3H,3H,5H,5H,6H,6H-perfluorotetradecyl]-1,4,7-tris(carboxymethyl)-1,4,7,10-tetraazacyclododecane 10 g (11.54 mmol) of the title compound of Example 3b) is dissolved in a mixture of 100 ml of water/50 ml of 2-propanol, and 2.09 g (5.77 mmol) of gadolinium oxide is added. It is stirred for 3 hours at 80° C. The solution is filtered and evaporated to dryness in a vacuum.

Yield: 12.48 g (quantitative) of a vitreous solid
Water content: 5.6%
$T_1$-relaxivity (L/mmol·sec) at 20 MHz, 37° C.:
15.2 (water)
27.5 (human plasma)

Elementary analysis (relative to anhydrous substance):
Cld: C, 31.77; H, 3.16; F, 31.64; Gd 15.40; N, 5.49. Fnd: C, 31.55; H, 3.30; F, 31.49; Gd 15.28; N, 5.35.

EXAMPLE 4 a) 1,2-Epoxy-4-oxa-1H,1H,2H,3H,3H,5H,5H,6H,6H-perfluorododecane 10.17 g (109.9 mmol) of epichlorohydrin is added in drops to a mixture of 20 g (54.93 mmol) of 1H,1H,2H,2H-perfluorooctan-1-ol and 1.87 g (5.5 mmol) of tetrabutylammonium hydrogen sulfate in 200 ml of 60% aqueous potassium hydroxide solution/100 ml of toluene while being stirred vigorously at 10° C., and care is taken to ensure that the temperature of the reaction solution is not higher than 20° C. It is allowed to stir for 2 hours at 15° C., and then 5.08 g (54.93 mmol) of epichlorohydrin is added in drops as described above. Then, it is stirred overnight at room temperature. 100 ml of toluene and 100 ml of methyl-tert-butyl ether are added, and the aqueous phase is separated. The latter is extracted twice more with 50 ml of toluene each. The organic phases are combined, dried on magnesium sulfate and concentrated by evaporation in a vacuum. The residue is chromatographed on silica gel (mobile solvent: dichloromethane/hexane/acetone=20/10/1).

Yield: 19.15 g (83% of theory) of a colorless oil
Elementary analysis:
Cld: C, 31.44; H, 2.16; F, 58.78. Fnd: C, 31.40; H, 2.29; F, 58.55.

b) 10-[2-Hydroxy-4-oxa-1H,1H,2H,3H,3H,5H,5H,6H,6H-perfluorododecyl]-1,4,7-tris(carboxymethyl)-1,4,7,10-tetraazacyclododecane 10.3 g (257 mmol) of sodium hydroxide is added to 14.84 g (42.84 mmol) of 1,4,7-tris(carboxymethyl)-1,4,7,10-tetraazacyclododecane (D03A) in 70 ml of water. A solution of 18 g (42.84 mmol) of the title compound of Example 4a), dissolved in 80 ml of n-butanol/60 ml of 2-propanol, is added dropwise to it, and the solution is heated overnight to 70° C. It is evaporated to dryness in a vacuum, the residue is taken up in 300 ml of water and adjusted to pH, 3 with 3N hydrochloric acid. Then, it is extracted twice with 200 ml of n-butanol. The combined butanol phases are evaporated to dryness in a vacuum, and the residue is purified by RP-chromatography (RP-18/mobile solvent: gradient consisting of water/n-butanol/acetonitrile).

Yield: 27.4 g (75% of theory) of a vitreous solid
Water content: 10.1%
Elementary analysis (relative to anhydrous substance):
Cld: C, 39.17; H, 4.60; F, 32.22; N, 7.31. Fnd: C, 39.05; H, 4.85; F, 32.05; N, 7.19.

c) Gadolinium complex of 10-[2-hydroxy-4-oxa-1H,1H,2H,3H,3H,5H,5H,6H,6H-perfluorododecyl]-1,4,7-tris(carboxymethyl)-1,4,7,10-tetraazacyclododecane 10 g (13.04 mmol) of the title compound of Example 4b) is dissolved in a mixture of 100 ml of water/50 ml of 2-propanol, and 2.36 g (6.52 mmol) of gadolinium oxide is added. It is stirred for 3 hours at 80° C. The solution is filtered and evaporated to dryness in a vacuum.

Yield: 12.77 g (quantitative) of a vitreous solid
Water content: 6.1%

Elementary analysis (relative to anhydrous substance):
Cld: C, 32.61; H, 3.50; F, 26.82; Gd 17.08; N, 6.08. Fnd: C, 32.43; H, 3.69; F, 26.67; Gd 16.85; N, 5.91.

EXAMPLE 5 a) 9,9,9,8,8,7,7,6,6-Nonafluoro-3-oxa-nonanoic acid-t-butyl ester 29.54 g (151.5 mmol) of bromoacetic acid-tert-butyl ester is added in drops to a mixture of 20 g (75.73 mmol) of 1H,1H,2H,2H-perfluorohexan-1-ol and 2.57 g (7.57 mmol) of tetrabutylammonium hydrogen sulfate in 300 ml of 60% aqueous potassium hydroxide solution/200 ml of toluene while being stirred vigorously at 0° C. It is stirred for 1 hour at 0° C. 100 ml of toluene is added, the aqueous phase is separated and extracted twice with 50 ml of toluene. The combined organic phases are dried on magnesium sulfate and concentrated by evaporation in a vacuum. The residue is chromatographed on silica gel (mobile solvent: hexane/dichloromethane/acetone=20/10/1).

Yield: 21.48 g (75% of theory) of a colorless oil
Elementary analysis:
Cld: C, 38.11; H, 4.00; F, 45.21. Fnd: C, 37.95; H, 4.18; F, 45.03.

b) 9,9,9,8,8,7,7,6,6-Nonanefluoro-3-oxa-nonanoic acid 20 g (52.88 mmol) of the title compound of Example 5a) is dissolved in 300 ml of trifluoroacetic acid and stirred overnight at room temperature. It is evaporated to dryness in a vacuum. The residue is recrystallized from hexane/ether.

Yield: 14.82 g (87% of theory) of a colorless crystalline solid
Elementary analysis:
Cld: C, 29.83; H, 2.19; F, 53.08. Fnd: C, 29.71; H, 2.40; F, 52.90.

c) Gadolinium complex of 10-[2-hydroxy-4-aza-5-oxo-7-oxa-10,10,11,11,12,12,13,13,13-nonafluoro-tridecyl]-1,4,7-tris(carboxymethyl)-1,4,7,10-tetraazacyclododecane 7.41 g (23.01 mmol) of the title compound of Example 5b) and 2.91 g (25.31 mmol) of N-hydroxysuccinimide are dissolved in a mixture of 40 ml of dimethylformamide/20 ml of chloroform. At 0° C., 5.22 g (25.31 mmol) of dicyclohexylcarbodiimide is added and stirred for 1 hour at 0° C., then for 3 hours at room temperature. It is cooled again to 0° C., and 6.98 g (69 mmol) of triethylamine/30 ml of 2-propanol is added. Then, 13.2 g (23.01 mmol) of the gadolinium complex of 10-(3-amino-2-hydroxy-propyl)-1,4,7-tris(carboxymethyl)-1,4,7,10-tetraazacyclododecane, dissolved in 40 ml of water, is added and stirred for 3 hours at room temperature. It is evaporated to dryness, the residue is taken up in a mixture of 200 ml of methanol/50 ml of chloroform, and dicyclohexylurea is filtered out. The filtrate is evaporated to dryness and purified by RP-chromatography (RP-18/mobile solvent: gradient consisting of water/n-propanol/acetonitrile).

Yield: 15.20 g (71 of theory) of a colorless vitreous solid
Water content: 5.7%
Elementary analysis (relative to anhydrous substance):
Cld: C, 34.21; H, 4.02; F, 19.48; Gd 17.91; N, 7.98. Fnd: C, 34.09; H, 4.18; F, 19.31; Gd 17.74; N, 7.87.

EXAMPLE 6 a) N-Ethyl-N-(perfluorooctylsulfonyl)-amino-acetic acid-N-(2-aminoethyl)-amide 15 g (25.63 mmol) of the title compound of Example 1b) and 3.24 g (28.19 mmol) of N-hydroxysuccinimide are dissolved in 80 ml of dimethylformamide, and 5.82 g (28.19 mmol) of dicyclohexylcarbodiimide is added at 0° C. It is stirred for 1 hour at 0° C., then for 2 hours at room temperature. Precipitated dicyclohexylurea is filtered out, and the filtrate is added in drops within 30 minutes in a solution of 46.21 g (768.9 mmol) of ethylenediamine in 300 ml of dichloromethane. It is stirred for 5 hours at room temperature. 1000 ml of $H_2O$ is added, and the organic phase is separated. The latter is washed twice with 500 ml of water each, then dried on magnesium sulfate and evaporated to dryness in a vacuum. The purification is carried out by chromatography on silica gel. (Mobile solvent: dichloromethane/2-propanol=15/1).

Yield: 11.79 g (75% of theory) of a colorless, waxy solid
Elementary analysis:
Cld: C, 27.42; H, 2.30; F, 52.66; N, 4.57; S, 5.23. Fnd: C, 27.20; H, 2.41; F, 52.48; N, 4.38; S, 5.10.

b) N-Ethyl-N-(perfluorooctylsulfonyl)-amino-acetic acid-N-[2-(bromoacetyl)-aminoethyl]-amide 10 g (16.3 mmol) of the title compound of Example 6a) and 2.02 g (20 mmol) of triethylamine are dissolved in 40 ml of dichloromethane. At −10° C., 3.29 g (16.3 mmol) of bromoacetyl bromide is added in drops within 30 minutes and stirred for 2 hours at 0° C. The solution is poured into 300 ml of 1N hydrochloric acid and stirred well. The organic phase is separated, dried on magnesium sulfate and concentrated by evaporation in a vacuum. The residue is chromatographed on silica gel (mobile solvent: dichloromethane/acetone=20/1).

Yield: 11.1 g (91% of theory) of a slightly yellow-colored waxy solid
Elementary analysis:
Cld: C, 25.68; H, 2.02 Br 10.68; F, 43.16; N, 5.62; S, 4.29. Fnd: C, 25.47; H, 2.18 Br 10.45; F, 43.29; N, 5.47; S, 4.10.

c) 10-[2-Oxo-3-aza-6-aza-7-oxo-9-aza-9-(perfluorooctylsulfonyl)-undecyl]-1,4,7-tris(carboxymethyl)-1,4,7,10-tetraazacyclododecane 4.63 g (13.36 mmol) of 1,4,7-tris(carboxymethyl-1,4,7,10-tetraazacyclododecane (D03A) and 18.5 g (133.6 mmol) of potassium carbonate are added to 10 g (13.36 mmol) of the title compound of Example 6b) in 180 ml of methanol. It is refluxed for 12 hours. The inorganic salts are filtered off, and the filtrate is evaporated to dryness. The residue is taken up in 100 ml of water and adjusted to pH, 3 with 5N hydrochloric acid. It is extracted twice with 150 ml of n-butanol. The combined organic phases are evaporated to dryness in a vacuum, and the residue is purified by RP-chromatography (RP-18/mobile solvent=gradient consisting of water/n-butanol/acetonitrile).

Yield: 10.43 g (67% of theory) of a colorless solid
Water content: 13.0%
Elementary analysis (relative to anhydrous substance):
Cld: C, 35.55; H, 3.98; F, 31.86; N, 9.67; S, 3.16. Fnd: C, 35.37; H, 3.75; F, 31.64; N, 9.78; S, 3.25.

d) Gadolinium complex of 10-[2-oxo-3-aza-6-aza-7-oxo-9-aza-9-(perfluorooctylsulfonyl)-undecyl]-1,4,7-tris(carboxymethyl)-1,4,7,10-tetraazacyclododecane 10 g (9.86 mmol) of the title compound of Example 6c) is dissolved in a mixture of 50 ml of water/20 ml of ethanol, and 1.79 g (4.93 mmol) of gadolinium oxide is added. It is stirred for 4 hours at 80° C. The solution is filtered and evaporated to dryness in a vacuum.

Yield: 12.4 g (quantitative)
Water content: 7.1%
Elementary analysis (relative to anhydrous substance):
Cld: C, 30.85; H, 3.19; F, 27.65; Gd 13.46; N, 8.39; S, 2.75. Fnd: C, 30.64; H, 3.35; F, 27.58; Gd 13.29; N, 8.28; S, 2.65.

EXAMPLE 7 a) 1H,1H,2H,2H-Perfluorodecan-1-ol-p-toluenesulfonic acid ester 12.57 g (65.93 mmol) of p-toluenesulfonic acid chloride is added to 30 g (64.64 mmol) of 1H,1H,2H,2H-perfluorodecan-1-ol in 300 ml of dichloromethane and 10.12 g (100 mmol) of triethylamine at 0° C. It is stirred for 2 hours at 0° C., then for 2 hours at room temperature. The solution is poured into 500 ml of cold 2N hydrochloric acid and stirred vigorously. The organic phase is separated, dried on magnesium sulfate and evaporated to dryness. The residue is recrystallized from a little methanol.

Yield: 39.97 (95% of theory) of a colorless crystalline powder
Elementary analysis:
Cld: C, 33.02; H, 1.79; F, 52.23; S, 5.19. Fnd: C, 32.81; H, 1.93; F, 52.04; S, 5.05.

b) 10-[(1-Hydroxymethyl-1-carboxy)-methyl]-1,4,7-tris(carboxymethyl)-1,4,7,10-tetraazacyclododecane 37.2 g (173.4 mmol) of 2-chloro-3-benzyloxy-propanoic acid is added to a solution of 20 g (57.78 mmol) of 1,4,7-tris(carboxymethyl)-1,4,7,10-tetraazacyclododecane (D03A), 31.21 g (780 mmol) of sodium hydroxide and 2 g (12 mmol) of potassium iodide in 100 ml of dimethylformamide, and it is stirred for 3 days at 60° C. It is evaporated to dryness, and the residue is dissolved in 300 ml of water. Then, it is adjusted to pH, 3 with 3N hydrochloric acid and extracted twice with 250 ml of dichloromethane each. 4 g of palladium catalyst (10% Pd/C) is added to the aqueous phase and hydrogenated for 5 hours at 60° C. The catalyst is filtered off, and the filtrate is evaporated to dryness. The residue is purified by RP-chromatography (RP-18/mobile solvent=gradient consisting of water/2-propanol/acetonitrile).

Yield: 5.92 g (21% of theory relative to D03A) of a colorless, vitreous solid
Water content: 11.1%
Elementary analysis (relative to anhydrous substance):
Cld: C, 47.00; H, 6.96; N, 12.90. Fnd: C, 46.81; H, 6.78; N, 12.99.

c) 10-[1-Hydroxymethyl-1-(methoxycarbonyl)-methyl]-1,4,7-tris(methoxycarbonylmethyl)-1,4,7,10-tetraazacyclododecane 9.53 g (80 mmol) of thionyl chloride is added in drops to 200 ml of methanol at 0° C. Then, 5.8 g (13.35 mmol) of the title compound of Example 7b) is added and stirred for 1 hour at 0° C. Then, it is heated for 6 hours to 60° C. It is evaporated to dryness, the residue is taken up in 150 ml of methylene chloride and extracted 3 times with 200 ml of 8% aqueous soda solution each. The organic phase is dried on magnesium sulfate and evaporated to dryness. 6.09 g (93% of theory) of the title compound is obtained as slightly yellowish-colored oil.

Elementary analysis:
Cld: C, 51.42; H, 7.81; N, 11.42. Fnd: C, 51.20; H, 7.95; N, 11.28.

d) 10-[1-(Methoxycarbonyl)-3-oxa-1H,2H,2H,4H,4H,5H,5H-perfluorotridecyl]-1,4,7-tris(methoxycarbonylmethyl)-1,4,7,10-tetraazacyclododecane 0.44 g (14.68 mmol) of sodium hydride (80% suspension in mineral oil) is added to 6 g (12.23 mmol) of the title compound of Example 7c) in 40 ml of dimethylformamide and stirred for 30 minutes at −10° C. Then, 8.32 g (13.45 mmol) of the title compound of Example 7a) is added and stirred for 8 hours at room temperature. 400 ml of ice water is carefully added and extracted twice with 300 ml of ethyl acetate each. The combined ethyl acetate phases are washed with saturated aqueous common salt solution and dried on magnesium sulfate. It is evaporated to dryness in a vacuum, and the residue is chromatographed on silica gel (mobile solvent: dichloromethane/methanol=20/1).

Yield: 7.68 g (67% of theory) of a viscous yellow oil
Elementary analysis:
Cld: C, 39.75; H, 4.41; F, 34.48; N, 5.98. Fnd: C, 39.58; H, 4.60; F, 34.27; N, 5.75.

e) 10-[1-Carboxy-3-oxa-1H,2H,2H,4H,4H,5H,5H-perfluorotridecyl]-1,4,7-tris(carboxymethyl)-1,4,7,10-tetraazacyclododecane 7.5 g (8.01 mmol) of the title compound of Example 7d) is suspended in a mixture of 50 ml of water/30 ml of ethanol, and then 3.84 g (96 mmol) of sodium hydroxide is added. It is refluxed overnight. It is cooled to room temperature and adjusted to pH, 3 with 3N hydrochloric acid. It is evaporated to dryness in a vacuum, and the residue is purified by RP-chromatography (RP-18/mobile-solvent=gradient consisting of water/n-butanol/acetonitrile).

Yield: 6.84 g (87% of theory) of a vitreous solid
Water content: 10.3%
Elementary analysis (relative to anhydrous substance):
Cld: C, 36.83; H, 3.78; F, 36.68; N, 6.36. Fnd: C, 36.67; H, 3.90; F, 36.49; N, 6.25.

f) Gadolinium complex of 10-[1-carboxy-3-oxa-1H,2H,2H,4H,4H,5H,5H-perfluorotridecyl]1,4,7-tris(carboxymethyl)-1,4,7,10-tetraazacyclododecane (as sodium salt)

6 g (6.81 mmol) of the title compound of Example 7e) is suspended in 80 ml of water, and 1.23 g (3.4 mmol) of gadolinium oxide is added. It is heated for 3 hours to 90° C. It is allowed to cool to room temperature and adjusted to pH, 7.2 with 2N sodium hydroxide solution. The solution is filtered and then freeze-dried.

Yield: 7.83 g (quantitative) of a colorless, flocculent powder
Water content: 8.1%

Elementary analysis (relative to anhydrous substance):
Cld: C, 30.69; H, 2.77; F, 30.56; Gd 14.88; N, 5.30; Na 2.18. Fnd: C, 30.48; H, 2.85; F, 30.37; Gd 14.69; N, 5.17; Na 1.95.

EXAMPLE 8 a) 2H,2H-Perfluorooctanal 30 g (82.4 mmol) of 1H,1H,2H,2H-perfluorooctan-1-ol is dissolved in 500 ml of dichloromethane, and 17.76 g (82.4 mmol) of pyridinium chlorochromate is added. It is stirred overnight at room temperature. The solution is filtered with a short column, filled with aluminum oxide (neutral), the filtrate is evaporated to dryness and the residue is chromatographed on silica gel (mobile solvent: dichloromethane/hexane/acetone=10/10/1).

Yield: 26.55 g (89% of theory) of a waxy solid
Elementary analysis:
Cld: C, 26.54; H, 0.84; F, 68.21. Fnd: C, 26.47; H, 1.05; F, 68.10.

b) 2-Amino-2H,3H,3H-perfluorononanoic acid (as hydrochloride)

7.04 g (143.6 mmol) of sodium cyanide and 8.45 g (158 mmol) of ammonium chloride are dissolved in 30 ml of water. 40 ml of ethanol and 26 g (71.8 mmol) of the title compound of Example 8a) are added to this solution. It is heated for 2 hours to 45° C. 300 ml of water is added, and it is extracted 3 times with 200 ml of benzene each. The combined benzene phases are washed 3 times with 200 ml of water each, and the organic phase is evaporated to dryness in a vacuum. The residue is taken up in 100 ml of 6N aqueous hydrochloric acid/50 ml of methanol and refluxed for 2 hours. It is evaporated to dryness in a vacuum. The residue is recrystallized from a little 2-propanol/methyl-tert-butyl ether.

Yield: 11.15 g (35% of theory) of a crystalline solid
Elementary analysis:
Cld: C, 24.37; H, 1.59 Cl 7.99; F, 55.68; N, 3.16. Fnd: C, 24.15; H, 1.72 Cl 7.65; F, 55.51; N, 3.05.

c) 2-[(N-Benzyloxycarbonyl)-triglycidyl]-amino-2H, 3H,3H-perfluorononanoic acid 8.37 g (24.8 mmol) of N-benzyloxycarbonyl-triglycine and 3.14 g (27.28 mmol) of N-hydroxysuccinimide are dissolved in 80 ml of dimethylformamide, and 5.63 g (27.28 mmol) of dicyclohexylcarbodiimide is added at 0° C. It is stirred for 1 hour at 0° C., then for 2 hours at room temperature. It is cooled to 0° C., 7.53 g (74.4 mmol) of triethylamine and 11 g (24.8 mmol) of the title compound of Example 8b are added and then stirred overnight at room temperature. It is evaporated to dryness in a vacuum, the residue is taken up in 300 ml of 5% aqueous citric acid and extracted 3 times with 200 ml of ethyl acetate each. The combined organic phases are dried on magnesium sulfate and evaporated to dryness in a vacuum. The residue is chromatographed on silica gel (mobile solvent: dichloromethane/n-propanol=20/1).

Yield: 11.83 g (67% of theory) of a colorless, sheetlike solid
Elementary analysis:
Cld: C, 38.78; H, 2.97; F, 34.67; N, 7.86. Fnd: C, 38.59; H, 2.85; F, 34.48; N, 7.91.

d) 2-[Triglycidyl]-amino-2H,3H,3H-perfluorononanoic acid 11.5 g (16.14 mmol) of the title compound of Example 8c) is dissolved in 200 ml of 2-propanol, and 3 g of palladium catalyst (10% Pd/C) is added. It is hydrogenated overnight at room temperature. Catalyst is filtered out, and the filtrate is evaporated to dryness.

Yield: 9.33 g (quantitative) of a colorless solid
Elementary analysis:
Cld: C, 31.15; H, 2.61; F, 42.71; N, 9.69. Fnd: C, 31.29; H, 2.80; F, 42.53; N, 9.48.

e) 2-(1H,1H-Perfluoroheptyl)-1,4,7,10-tetraaza-3,6, 9,12-tetraoxo-cyclododecane 9.2 g (15.91 mmol) of the title compound of Example 8d) is dissolved in 1000 ml of dimethylformamide, and 3.93 g (15.91 mmol) of 2-ethoxy-1-ethoxycarbonyl-1,2-dihydroquinoline is added. It is stirred for 3 days at room temperature. It is evaporated to dryness, and the residue is chromatographed on silica gel (mobile solvent: dichloromethane/2-propanol=20/1).

Yield: 4.54 g (51% of theory) of a waxy solid
Elementary analysis:
Cld: C, 32.16; H, 2.34; F, 44.08; N, 10.00. Fnd: C, 32.05; H, 2.47; F, 43.87; N, 9.89.

f) 2-(1H,1H-Perfluoroheptyl)-1,4,7,10-tetraazacyclododecane (as tetrahydrochloride)

200 ml of 1M borane-tetrahydrofuran complex solution is added to 4.4 g (7.85 mmol) of the title compound of Example 8e) and refluxed for 2 days. It is evaporated to dryness in a vacuum, and the residue is taken up in 50 ml of concentrated hydrochloric acid. 100 ml of ethanol is added, and it is refluxed for 8 hours. It is evaporated to dryness in a vacuum, and the residue is recrystallized from ethanol.

Yield: 4.75 g (93% of theory) of a colorless, crystalline powder
Elementary analysis:
Cld: C, 27.71; H, 3.88; Cl, 21.81; F, 37.99; N, 8.62. Fnd: C, 27.65; H, 3.95; Cl, 21.40; F, 37.69; N, 8.41.

g) 2-(1H,1H-Perfluoroheptyl)-1,4,7,10-tetra(carboxymethyl)-1,4,7,10-tetraazacyclododecane 4.6 g (7.07 mmol) of the title compound of Example 8f) and 4.0 g (42.4 mmol) of chloroacetic acid are dissolved in 40 ml of water, and the pH is adjusted to 10 by adding 30% aqueous potassium hydroxide solution. It is heated for 8 hours to 70° C. and in this case, the pH is kept between 8 and 10 (by adding 30% aqueous potassium hydroxide solution). The solution is cooled to room temperature, adjusted to pH 2 with concentrated hydrochloric acid and evaporated to dryness. The residue is taken up in 150 ml of methanol, the salts are filtered off and the filtrate is evaporated to dryness in a vacuum. The residue is purified by RP-18 chromatography (RP-18/mobile solvent: gradient consisting of water/2-propanol/acetonitrile).

Yield: 5.03 g (87% of theory) of a vitreous solid
Water content: 10.1%
Elementary analysis (relative to anhydrous substance):
Cld: C, 37.51; H, 3.97; F, 33.53; N 7.61. Fnd: C, 37.35; H, 4.12; F, 33.40; N 7.45.

h) Gadolinium complex of 2-(1H,1H-perfluoroheptyl)-1,4,7,10-tetra(carboxymethyl)-1,4,7,10-tetraazacyclododecane (as sodium salt)

4.5 g (6.11 mmol) of the title compound of Example 8g) is suspended in 100 ml of water, and 1.107 g (3.05 mmol) of gadolinium oxide is added. It is heated for 3 hours to 90° C. It is allowed to cool to room temperature and adjusted to pH 7.2 with 2N sodium hydroxide solution. The solution is filtered and then freeze-dried.

Yield: 6.03 g (quantitative) of a colorless powder
Water content: 7.5%
Elementary analysis (relative to anhydrous substance):
Cld: C, 30.23; H, 2.87; F, 27.03; Gd, 17.21; N, 6.13; Na, 2.52. Fnd: C, 30.10; H, 3.05; F, 26.81; Gd, 17.15; N, 5.95; Na, 2.30.

EXAMPLE 9 a) 10-[2-Hydroxy-1H,1H,2H,3H,3H-perfluorononyl]-1,4,7-tris(carboxymethyl)-1,4,7,10-tetraazacyclododecane 13.85 g (346.4 mmol) of sodium hydroxide is added to 15 g (43.3 mmol) of 1,4,7-tris(carboxymethyl)-1,4,7,10-tetraazacyclododecane in 50 ml of water. A solution of 27.68 g (64.95 mmol) of 1,2-epoxy-1H,1H,2H,3H,3H-perfluorononane, dissolved in 50 ml of n-butanol/50 ml of 2-propanol, is added dropwise to it, and the solution is heated overnight to 80° C. It is evaporated to dryness in a vacuum, the residue is taken up in 200 ml of water and adjusted to pH 3 with 3N hydrochloric acid. Then, it is extracted twice with 200 ml of n-butanol. The combined butanol phases are evaporated to dryness in a vacuum, and the residue is purified by RP-chromatography (RP-18/mobile solvent: gradient consisting of water/n-butanol/acetonitrile).

Yield: 30.34 g (78% of theory) of a vitreous solid
Water content: 13.7%
Elementary analysis (relative to anhydrous substance):
Cld: C, 37.32; H, 4.04; F, 36.89; N, 7.25. Fnd: C, 37.15; H, 4.21; F, 36.70; N, 7.19.

b) Gadolinium complex of 10-[2-hydroxy-1H,1H,2H,3H,3H-perfluorononyl]-1,4,7-tris(carboxymethyl)-1,4,7,10-tetraazacyclododecane 10 g (12.94 mmol) of the title compound of Example 9a) is dissolved in 100 ml of water/50 ml of ethanol, and 2.34 g (6.47 mmol) of gadolinium oxide is added. It is stirred for 3 hours at 80° C. The solution is filtered and evaporated to dryness in a vacuum.

Yield: 13.16 g (quantitative) of a colorless, vitreous solid
Water content: 9.1%
Elementary analysis (relative to anhydrous substance):
Cld: C, 31.11; H, 3.05; F, 30.75; Gd, 16.97; N, 6.05. Fnd: C, 31.01; H, 3.19; F, 30.55; Gd, 16.71; N, 5.88.

EXAMPLE 10 a) 9H,9H,10H,11H,12H,12H-Perfluoroeicos-10-ene 24.77 g (52.26 mmol) of 1H,1H,2H,2H-perfluorodecyl-1-iodide and 13.71 g (52.26 mmol) of triphenylphosphine are heated to 70° C. in 500 ml of acetone while being stirred. The initially clear solution quickly turns milky, and the colorless phosphonium salt is precipitated. The phosphonium salt is filtered off and dried in a vacuum at 40° C.

Yield: 38.9 g (89% of theory)

This phosphonium salt is used directly in the following reaction without purification: 5.22 g (46.5 mmol) of potassium-tert-butylate, 0.20 g (0.75 mmol) of 18-crown 6 and 19.54 g (42.28 mmol) of 2H,2H-perfluorodecanol are added to the above-produced phosphonium salt, 38.9 g (46.5 mmol) in 250 ml of dichloromethane, and it is stirred for 10 hours at room temperature. It is evaporated to dryness, and the residue is chromatographed on silica gel (mobile solvent: dichloromethane/n-hexane/diethyl ether=10/20/1).

Yield: 30.3 g (65% of theory relative to the iodide used) of a colorless waxy solid
Elementary analysis:
Cld: C, 26.92; H, 0.68; F, 72.40. Fnd: C, 26.81; H, 0.79; F, 72.20.

b) 10,11-Epoxy-9H,9H,10H,11H,12H,12H-perfluoroeicosane 10.47 g (36.42 mmol) of 3-chloroperoxybenzoic acid (about 60%) is added to 25 g (28.02 mmol) of the title compound of Example 10a), dissolved in 250 ml of dichloromethane, at 0° C., and it is stirred overnight at room temperature. 300 ml of 5% aqueous sodium carbonate solution is added and stirred well. The organic phase is separated, dried on magnesium sulfate and evaporated to dryness in a vacuum. The residue is chromatographed on silica gel (mobile solvent: n-hexane/dichloromethane/diethyl ether=10/10/1).

Yield: 24.17 g (95% of theory) of a colorless solid
Elementary analysis:
Cld: C, 26.45; H, 0.67; F, 71.12. Fnd: C, 26.25; H, 0.88; F, 71.35.

c) 10-[1-(1H,1H-Perfluorononyl)-2-hydroxy-1H,2H,3H,3H-perfluoroundecyl]-1,4,7-tris(carboxymethyl)-1,4,7,10-tetraazacyclododecane 7.04 g (0.176 mmol) of sodium hydroxide is added to 7.63 g (22.02 mmol) of 1,4,7-tris(carboxymethyl)-1,4,7,10-tetraazacyclododecane in 35 ml of water. A solution of 20 g (22.02 mmol) of the title compound of Example 10b), dissolved in 50 ml of n-butanol/40 ml of 2-propanol, is added dropwise to it, and the solution is heated overnight to 120° C. in an autoclave. It is evaporated to dryness in a vacuum, the residue is taken up in 200 ml of water and adjusted to pH 3 with 3N hydrochloric acid. Then, it is extracted twice with 300 ml of n-butanol. The combined butanol phases are evaporated to dryness in a vacuum, and the residue is purified by RP-chromatography (RP-18/mobile solvent: gradient consisting of water/n-butanol/acetonitrile).

Yield: 9.79 g (31% of theory) of a colorless, vitreous solid
Water content: 12.5%
Elementary analysis (relative to anhydrous substance):
Cld: C, 32.55; H, 2.57; F, 51.49; N, 4.47. Fnd: C, 32.38; H, 2.75; F, 51.29; N, 4.28.

d) Gadolinium complex of 10-[1-(1H,1H-perfluorononyl)-2-hydroxy-1H,2H,3H,3H-perfluoroundecyl]-1,4,7-tris(carboxymethyl)-1,4,7,10-tetraazacyclododecane 8 g (6.38 mmol) of the title compound of Example 10c) is dissolved in 50 ml of water/40 ml of ethanol/20 ml of chloroform, and 1.16 g (3.19 mmol) of gadolinium oxide is added. It is stirred for 4 hours at 90° C. in an autoclave. The solution is filtered and evaporated to dryness in a vacuum.

Yield: 9.47 g (quantitative) of a vitreous solid
Water content: 5.2%
Elementary analysis (relative to anhydrous substance):
Cld: C, 28.99; H, 2.07; F, 45.85; Gd, 11.16; N, 3.98. Fnd: C, 28.81; H, 2.19; F, 45.71; Gd, 11.03; N, 4.12.

EXAMPLE 11 a) 7H,7H,8H,9H,10H,10H-Perfluorohexadec-8-ene 18.7 g (50 mmol) of 1H,1H,2H,2H-perfluorooctyl-1-iodide and 13.11 g (50 mmol) of triphenylphosphine are heated to 70° C. in 400 ml of acetone while being stirred. The initially clear solution quickly turns milky, and the colorless phosphonium salt is precipitated. The phosphonium salt is filtered off and dried in a vacuum at 40° C.

Yield: 28.95 g (91% of theory)

This phosphonium salt is used directly in the following reaction without purification: 5.05 g (45.5 mmol) of potassium-tert-butylate, 0.20 g (0.75 mmol) of 18-crown 6 and 14.98 g (41.36 mmol) of the title compound of Example 8a) are added to the above-produced phosphonium salt, 28.95 g (45.5 mmol) in 200 ml of dichloromethane, and it is stirred for 10 hours at room temperature. It is evaporated to dryness, and the residue is chromatographed on silica gel (mobile solvent: dichloromethane/n-hexane/diethyl ether=10/20/1).

Yield: 19.65 g (61% of theory) of a colorless, waxy solid
Elementary analysis:
Cld: C, 22.38; H, 0.94; F, 76.69. Fnd: C, 22.20; H, 0.99; F, 76.51.

b) 8,9-Epoxy-7H,7H,8H,9H, 10H,10H-perfluorohexadecane 11.03 g (38.35 mmol) of 3-chloroperoxybenzoic acid (about 60%) is added to 19 g (29.5 mmol) of the title compound of Example 11a), dissolved in 200 ml of dichloromethane, at 0° C., and it is stirred overnight at room temperature. 300 ml of 5% aqueous sodium carbonate solution is added and stirred well. The organic phase is separated, dried on magnesium sulfate and evaporated to dryness in a vacuum. The residue is chromatographed on silica gel (mobile solvent: n-hexane/dichloromethane/diethyl ether=10/10/1).

Yield: 19.43 g (93% of theory) of a colorless solid
Elementary analysis:
Cld: C, 27.14; H, 0.85; F, 69.75. Fnd: C, 27.01; H, 0.97; F, 69.60.

c) 10-[1-(1H,1H-Perfluoroheptyl)-2-hydroxy-1H, 2H,3H,3H-perfluorononyl]-1,4,7-tris(carboxymethyl)-1,4,7,10-tetraazacyclododecane 8.59 g (214.6 mmol) of sodium hydroxide is added to 9.3 g (26.83 mmol) of 1,4,7-tris(carboxymethyl)-1,4,7,10-tetraazacyclododecane in 50 ml of water. A solution of 19 g (26.83 mmol) of the title compound of Example 11b), dissolved in 70 ml of n-butanol/60 ml of 2-propanol, is added dropwise to it, and the solution is heated overnight to 120° C. in an autoclave. It is evaporated to dryness in a vacuum, the residue is taken up in 200 ml of water and adjusted to pH 3 with 3N hydrochloric acid. Then, it is extracted twice with 300 ml of n-butanol. The combined butanol phases are evaporated to dryness in a vacuum, and the residue is purified by RP-chromatography (RP-18/mobile solvent: gradient consisting of water/n-butanol/acetonitrile).

Yield: 9.4 g (29% of theory) of a vitreous solid
Water content: 12.7%
Elementary analysis (relative to anhydrous substance):
Cld: C, 34.17; H, 3.06; F, 46.84; N, 5.31. Fnd: C, 33.98; H, 3.18; F, 46.65; N, 5.20.

d) Gadolinium complex of 10-[1-(1H,1H-perfluoroheptyl)-2-hydroxy-1H,2H,3H,3H-perfluorononyl]-1, 4,7-tris(carboxymethyl)-1,4,7,10-tetraazacyclododecane 9 g (8.53 mmol) of the title compound of Example 11c) is dissolved in 60 ml of water/40 ml of ethanol/30 ml of chloroform, and 1.54 g (4.27 mmol) of gadolinium oxide is added. It is stirred for 4 hours at 90° C. in an autoclave. The solution is filtered and evaporated to dryness in a vacuum.

Yield: 11.45 g (quantitative) of a colorless, vitreous solid
Water content: 10.2%
Elementary analysis (relative to anhydrous substance):
Cld: C, 29.81; H, 2.42; F, 40.86; Gd, 13.01; N, 4.63. Fnd: C, 29.60; H, 2.60; F, 40.63; Gd, 12.84; N, 4.51.

EXAMPLE 12 a) 7,12-Dioxa-5H,5H,6H,6H,8H,8H,9H,10H,11H, 11H,13H,13H,14H,14H-perfluorooctadec-9-ene 30 g (91.74 mmol) of 1H,1H,2H,2H-perfluorohexyl-1-bromide is dissolved in 100 ml of toluene, then 3.23 g (36.7 mmol) of cis-1,4-butene-diol and 1 g (2.95 mmol) of tetrabutylammonium hydrogen sulfate are added. It is cooled to 0° C., and 16 g (400 mmol) of finely powdered sodium hydroxide is added. Then, it is stirred for 1 hour at 0° C. and overnight at room temperature. Solid is filtered out, the filtrate is washed twice with 200 ml of water each, the organic phase is dried on magnesium sulfate and then evaporated to dryness in a vacuum. The residue is chromatographed on silica gel (mobile solvent: dichloromethane/n-hexane/acetone=15/15/1).

Yield: 11.71 g (55% of theory relative to diol) of a waxy solid
Elementary analysis:
Cld: C, 33.12; H, 2.43; F, 58.93. Fnd: C, 33.05; H, 2.61; F, 58.73.

b) 9,10-Epoxy-7,12-dioxa-5H,5H,6H,6H,8H,8H,9H, 10H,11H,11H,13H,13H,14H,14H-perfluorooctadecane 7.08 g (24.64 mmol) of 3-chloroperoxybenzoic acid (about 60%) is added to 11 g (18.96 mmol) of the title compound of Example 12a), dissolved in 100 ml of dichloromethane, at 0° C., and it is stirred overnight at room temperature. 150 ml of 5% aqueous sodium carbonate solution is added and stirred well. The organic phase is separated, dried on magnesium sulfate and evaporated to dryness in a vacuum. The residue is chromatographed on silica gel (mobile solvent: n-hexane/dichloromethane/diethyl ether=10/10/1).

Yield: 10.74 g (95% of theory) of a colorless solid
Elementary analysis:
Cld: C, 32.23; H, 2.37; F, 57.35. Fnd: C, 32.13; H, 2.51; F, 57.20.

c) 10-[1-(2-Oxa-1H,1H,3H,3H,4H,4H-perfluorooc-tyl)-2-hydroxy-4-oxa-1H,2H,3H,3H,5H,5H,6H,6H-perfluorodecyl]-1,4,7-tris(carboxymethyl)-1,4,7,10-tetraazacyclododecane 5.63 g (141 mmol) of sodium hydroxide is added to 6.1 g (17.61 mmol) of 1,4,7-tris(carboxymethyl)-1,4,7,10-tetraazacyclododecane in 40 ml of water. A solution of 10.5 g (17.61 mmol) of the title compound of Example 12b), dissolved in 50 ml of n-butanol/40 ml of 2-propanol, is added dropwise to it, and the solution is heated overnight to 120° C. in an autoclave. It is evaporated to dryness in a vacuum, the residue is taken up in 200 ml of water and adjusted to pH 3 with 3N hydrochloric acid. Then, it is extracted twice with 300 ml of n-butanol. The combined butanol phases are evaporated to dryness in a vacuum, and the residue is purified by RP-chromatography (RP-18/mobile solvent: gradient consisting of water/n-butanol/acetonitrile).

Yield: 4.96 g (27% of theory) of a colorless, vitreous solid
Water content: 9.7%
Elementary analysis (relative to anhydrous substance):
Cld: C, 38.27; H, 4.17; F, 36.63; N, 5.95. Fnd: C, 38.12; H, 4.20; F, 36.20; N, 5.81.

d) Gadolinium complex of 10-[1-(2-oxa-1H,1H,3H,3H,4H,4H-perfluorooctyl)-2-hydroxy-4-oxa-1H,2H,3H,3H,5H,5H,6H,6H-perfluorodecyl]-1,4,7-tris(carboxymethyl)-1,4,7,10-tetraazacyclododecane 4.7 g (5 mmol) of the title compound of Example 12c) is dissolved in 30 ml of water/30 ml of ethanol/20 ml of chloroform, and 0.90 g (2.5 mmol) of gadolinium oxide is added. It is stirred for 3.5 hours at 90° C. in an autoclave. The solution is filtered and evaporated to dryness in a vacuum.

Yield: 5.89 g (quantitative) of a colorless, vitreous solid
Water content: 7.1%
Elementary analysis (relative to anhydrous substance):
Cld: C, 32.88; H, 3.31; F, 31.21; Gd, 14.35; N, 5.11. Fnd: C, 32.67; H, 3.45; F, 31.04; Gd, 14.18; N, 5.02.

EXAMPLE 13 a) 1-Phenyl-2,6-dioxa-1H,1H,3H,3H,4H,5H,5H,7H,7H,8H,8H-perfluorohexa-decan-4-ol 1 g (2.94 mmol) of tetrabutylammonium hydrogen sulfate and 15.6 g (390 mmol) of finely powdered sodium hydroxide are added to 7.14 g (39.2 mmol) of glycerol-1-monobenzylether and 25 g (43.55 mmol) of 1H,1H,2H,2H-perfluorodecyl-1-iodide in 100 ml of toluene. It is stirred for 24 hours at room temperature. The organic phase is separated from the solid and washed twice with 5% aqueous hydrochloric acid each. The organic phase is dried on magnesium sulfate and evaporated to dryness in a vacuum. The residue is chromatographed on silica gel (mobile solvent: n-hexane/acetone=15/1).

Yield: 19.95 g (81% of theory) of a colorless oil
Elementary analysis:
Cld: C, 38.23; H, 2.73; F, 51.40. Fnd: C, 38.10; H, 2.89; F, 51.25.

b) 1-Phenyl-4-(decyloxy)-2,6-dioxa-1H,1H,3H,3H,4H,5H,5H,7H,7H,8H,8H-perfluorohexadecane 1.12 g (37.24 mmol) of sodium hydride (80% suspension in mineral oil) is added in portions to 19.5 g (31.03 mmol) of the title compound of Example 13a), dissolved in 100 ml of dimethylformamide, and it is stirred for 2 hours at room temperature. Then, 8.24 g (37.24 mmol) of n-decyl bromide is added and stirred overnight at 50° C. 150 ml of ice water is added and extracted twice with 150 ml of ethyl acetate each. The combined organic phases are washed twice with 150 ml of water each, dried on magnesium sulfate and evaporated to dryness. The residue is chromatographed on silica gel (mobile solvent: n-hexane/acetone=20:1);

Yield: 22.66 g (95% of theory) of a waxy solid
Elementary analysis:
Cld: C, 46.88; H, 4.85; F, 42.02.
Fnd: C, 46.64; H, 4.97; F, 41.87.

c) 2-(Decyloxy)-4-oxa-1H,1H,2H,3H,3H,5H,5H,6H,6H-perfluorotetradecan-1-ol 20 g (26.02 mmol) of the title compound of Example 13b) is dissolved in 200 ml of isopropanol, and 3 g of palladium catalyst (10% Pd/C) is added. It is hydrogenated overnight at room temperature. The catalyst is filtered off, and the filtrate is evaporated to dryness in a vacuum.

Yield: 17.65 g (quantitative) of a colorless solid
Elementary analysis:
Cld: C, 40.72; H, 4.61; F, 47.60. Fnd: C, 40.55; H, 4.76; F, 47.43.

d) 1,2-Epoxy-4-oxa-6-(decyloxy)-8-oxa-1H,1H,2H,3H,3H,5H,5H,6H,7H,7H,9H,9H,10H,10H-perfluorooctadecane 9.25 g (100 mmol) of epichlorohydrin is added in drops to a mixture of 17 g (25.06 mmol) of the title compound of Example 13c) and 2 g (5.89 mmol) of tetrabutylammonium hydrogen sulfate in 300 ml of 60% aqueous potassium hydroxide solution/100 ml of toluene while being stirred vigorously at 10° C., and care is taken to ensure that the temperature of the reaction solution does not exceed 20° C. It is allowed to stir for 2 hours at 15° C., and then 4.63 g (50 mmol) of epichlorohydrin is added in drops as described above. Then, it is stirred overnight at room temperature. 100 ml of toluene and methyl-tert-butyl ether are added, and the aqueous phase is separated. The latter is extracted twice more with 100 ml of toluene each. The organic phases are combined, dried on magnesium sulfate and concentrated by evaporation in a vacuum. The residue is chromatographed on silica gel (mobile solvent: dichloromethane/hexane/acetone=20/10/1).

Yield: 14.91 g (81% of theory) of a colorless solid
Elementary analysis:
Cld: C, 42.51; H, 4.80; F, 43.97. Fnd: C, 42.37; H, 4.96; F, 43.68.

e) 10-[2-Hydroxy-4,8-dioxa-6-(decyloxy)-1H,1H,2H,3H,3H,5H,5H,6H,7H,7H,9H,9H,10H,10H-perfluorooctadecyl]-1,4,7-tris(carboxymethyl)-1,4,7,10-tetraazacyclododecane 6.11 g (152.8 mmol) of sodium hydroxide is added to 6.6 g (19.06 mmol) of 1,4,7-tris(carboxymethyl)-1,4,7,10-tetraazacyclododecane in 60 ml of water. A solution of 14 g (19.06 mmol) of the title compound of Example 13d), dissolved in 80 ml of n-butanol/40 ml of 2-propanol, is added dropwise to it, and the solution is heated overnight to 80° C. in an autoclave. It is evaporated to dryness in a vacuum, the residue is taken up in 200 ml of water, and it is adjusted to pH 3 with 3N hydrochloric acid. Then, it is extracted twice with 300 ml of n-butanol. The combined butanol phases are evaporated to dryness in a vacuum, and the residue is purified by RP-chromatography (RP-18/mobile solvent: gradient consisting of water/n-butanol/acetonitrile).

Yield: 17.88 g (76% of theory) of a vitreous solid
Water content: 12.5%
Elementary analysis (relative to anhydrous substance):
Cld: C, 44.49; H, 5.60; F, 29.91; N, 5.19. Fnd: C, 44.31; H, 5.75; F, 29.70; N, 5.03.

f) Gadolinium complex of 10-[2-hydroxy-4,8-dioxa-6-(decyloxy)-1H,1H,2H,3H,3H,5H,5H,6H,7H,7H,9H,9H,10H,10H-perfluorooctadecyl]-1,4,7-tris(carboxymethyl)-1,4,7,10-tetraazacyclododecane 10 g (9.26 mmol) of the title compound of Example 13e) is dissolved in 30 ml of water/100 ml of ethanol/30 ml of chloroform, and 1.68 g (4.63 mmol) of gadolinium oxide is added. It is stirred for 3.5 hours at 90° C. in an autoclave. The solution is filtered and evaporated to dryness in a vacuum.

Yield: 12.39 g (quantitative) of a colorless, vitreous solid
Water content: 7.8%
Elementary analysis (relative to anhydrous substance):
Cld: C, 38.93; H, 4.66; F, 26.17; Gd, 12.74; N, 4.54. Fnd: C, 38.71; H, 4.82; F, 26.01; Gd, 12.55; N, 4.38.

EXAMPLE 14 a) 1-Phenyl-2-oxa-4,4,4-tris(2-oxa-1H,1H,3H,3H,4H,4H-perfluorodecyl)-butane 2 g (5.89 mmol) of tetrabutylammonium hydrogen sulfate and 22.48 g (562 mmol) of finely powdered sodium hydroxide are added to 4.24 g (18.74 mmol) of pentaerythritol monobenzyl ether and 40 g (93.7 mmol) of 1H,1H,2H,2H-perfluorooctyl-1-bromide in 150 ml of toluene. It is stirred for 24 hours at room temperature. The organic phase is separated from the solid and washed twice with 5% aqueous hydrochloric acid each. The organic phase is dried on magnesium sulfate and evaporated to dryness in a vacuum. The residue is chromatographed on silica gel (mobile solvent: n-hexane/acetone=25/1).

Yield: 14.45 g (61% of theory relative to the benzyl ether) of a colorless, waxy solid
Elementary analysis:
Cld: C, 34.19; H, 2.15; F, 58.59. Fnd: C, 34.02; H, 2.31; F, 58.41.

b) 2,2,2-Tris(2-oxa-1H,1H,3H,3H,4H,4H-perfluorodecyl)-ethan-1-ol 14 g (11.07 mmol) of the title compound of Example 14a) is dissolved in 100 ml of isopropanol/100 ml of tetrahydrofuran, and 3 g of palladium catalyst (10% Pd/C) is added. It is hydrogenated overnight at room temperature. The catalyst is filtered off, and the filtrate is evaporated to dryness in a vacuum.

Yield: 13 g (quantitative) of a colorless solid
Elementary analysis:
Cld: C, 29.66; H, 1.80; F, 63.09. Fnd: C, 29.45; H, 1.97; F, 62.91.

c) 1,2-Epoxy-4-oxa-6,6,6-tris(2-oxa-1H,1H,3H,3H,4H,4H-perfluorodecyl)-hexane 3.94 g (42.57 mmol) of epichlorohydrin is added in drops to a mixture of 12.5 g (10.64 mmol) of the title compound of Example 14b) and 1 g (2.95 mmol) of tetrabutylammonium hydrogen sulfate in 150 ml of 60% aqueous potassium hydroxide solution/50 ml of toluene while being stirred vigorously at 10° C., and care is taken to ensure that the temperature of the reaction solution does not exceed 20° C. It is allowed to stir for 2 hours at 15° C., and then 1.97 g (21.29 mmol) of epichlorohydrin is added in drops as described above. Then, it is stirred overnight at room temperature. 100 ml of toluene and 100 ml of methyl-tert-butyl ether are added, and the aqueous phase is separated. The latter is extracted twice more with 50 ml of toluene each. The organic phases are combined, dried on magnesium sulfate and concentrated by evaporation in a vacuum. The residue is chromatographed on silica gel (mobile solvent: dichloromethane/hexane/acetone=20/10/1).

Yield: 8.12 g (62% of theory) of a colorless solid
Elementary analysis:
Cld: C, 31.24; H, 2.05; F, 60.22. Fnd: C, 31.09; H, 2.19; F, 60.10.

d) 10-[2-Hydroxy-4-oxa-6,6,6-tris(2-oxa-1H,1H,3H,3H,4H,4H-perfluorodecyl)-hexyl]-1,4,7-tris(carboxymethyl)-1,4,7,10-tetraazacyclododecane 2.08 g (52 mmol) of sodium hydroxide is added to 2.25 g (6.50 mmol) of 1,4,7-tris(carboxymethyl)-1,4,7,10-tetraazacyclododecane in 30 ml of water. A solution of 8.0 g (6.50 mmol) of the title compound of Example 14c), dissolved in 50 ml of n-butanol/30 ml of 2-propanol, is added dropwise to it, and the solution is heated overnight to 100° C. in an autoclave. It is evaporated to dryness in a vacuum, the residue is taken up in 200 ml of water and adjusted to pH 3 with 3N hydrochloric acid. Then, it is extracted twice with 100 ml of n-butanol. The combined butanol phases are evaporated to dryness in a vacuum, and the residue is purified by RP-chromatography (RP-18/mobile solvent: gradient consisting of water/n-butanol/acetonitrile).

Yield: 7.79 g (67% of theory) of a colorless, vitreous solid
Water content: 11.9%
Elementary analysis (relative to anhydrous substance):
Cld: C, 35.06; H, 3.20; F, 47.02; N, 3.56. Fnd: C, 34.90; H, 3.38; F, 46.86; N, 3.47.

e) Gadolinium complex of 10-[2-hydroxy-4-oxa-6,6,6-tris(2-oxa-1H,1H,3H,3H,4H,4H-perfluorodecyl)-hexyl]-1,4,7-tris(carboxymethyl)-1,4,7,10-tetraazacyclododecane 7 g (4.44 mmol) of the title compound of Example 14d) is dissolved in 30 ml of water/50 ml of ethanol/50 ml of chloroform, and 0.80 g (2.22 mmol) of gadolinium oxide is added. It is stirred for 5 hours at 90° C. in an autoclave. The solution is filtered and evaporated to dryness in a vacuum.

Yield: 8.34 g (quantitative) of a colorless, vitreous solid
Water content: 8.1%
Elementary analysis (relative to anhydrous substance):
Cld: C, 31.94; H, 2.74; F, 42.83; Gd, 9.09; N, 3.24. Fnd: C, 31.74; H, 2.91; F, 42.67; Gd, 8.85; N, 3.15.

EXAMPLE 15 a) 1,7-Bis[acetyl-(2-(N-ethyl-N-perfluorooctylsulfonylamino)]-1,4,7-triazaheptane 20 g (34.17 mmol) of the title compound of Example 1b) and 4.33 g (37.59 mmol) of N-hydroxysuccinimide are dissolved in 150 ml of dimethylformamide. 7.76 g (37.59 mmol) of dicyclohexylcarbodiimide is added at 0° C. and stirred for 3 hours at room temperature. Dicyclohexylurea is filtered out, and the filtrate is added in drops to a solution of 1.76 g (17.09 mmol) of diethylenetriamine and 13.83 g (136.7 mmol) of triethylamine in 200 ml of dimethylformamide at room temperature. It is stirred overnight at room temperature. It is evaporated to dryness in a vacuum, and the residue is taken up in 200 ml of 5% aqueous soda solution. It is extracted twice with 150 ml of dichloromethane each, the combined organic phases are dried on magnesium sulfate and evaporated to dryness in a vacuum. The residue is chromatographed on silica gel (mobile solvent: dichloromethane/2-propanol=20/1).

Yield: 16.5 g (78% of theory) of a waxy solid

Elementary analysis:

Cld: C, 27.17; H, 2.04; F, 52.19; N, 5.66; S, 5.18. Fnd: C, 27.03; H, 2.17; F, 52.04; N, 5.49; S, 5.07.

b) 4-(3-Carboxy-propanoyl)-1,7-bis-{acetyl-[2-(N-ethyl-N-perfluorooctylsulfonylamino)]}-1,4,7-triaza-heptane 3.92 g (38.78 mmol) of triethylamine is added to 16 g (12.93 mmol) of the title compound of Example 15a) in 100 ml of methylene chloride, and the solution is cooled to 0° C. Then, 2.59 g (25.86 mmol) of succinic anhydride is added and stirred for 3 hours at 0° C., overnight at room temperature. 200 ml of 5% aqueous hydrochloric acid is added and shaken well. The organic phase is separated and dried on magnesium sulfate. It is evaporated to dryness in a vacuum, and the residue is chromatographed on silica gel (mobile solvent: dichloromethane/2-propanol=15/1).

Yield: 15.74 g (91% of theory) of a colorless solid

Elementary analysis:

Cld: C, 28.73; H, 2.19; F, 48.29; N, 5.24; S, 4.79. Fnd: C, 28.58; H, 2.40; F, 48.17; N, 5.17; S, 4.65.

c) 10-(7-Hydroxy-5-aza-4-oxo-octanoic acid-N,N-bis(3-aza-4-oxo-6-aza-6-(perfluorooctylsulfonyl)-octyl)-amide]-1,4,7-tris(carboxymethyl)-1,4,7,10-tetraazacyclododecane 15 g (11.21 mmol) of the title compound of Example 15b) and 1.42 g (12.33 mmol) of N-hydroxysuccinimide are dissolved in a mixture of 80 ml of dimethylformamide/30 ml of chloroform. 2.54 g (12.33 mmol) of dicyclohexylcarbodiimide is added at 0° C. and stirred for 1 hour at 0° C., then for 3 hours at room temperature. It is cooled again to 0° C., and 4.05 g (40 mol) of triethylamine/50 ml of 2-propanol is added. Then, 7.07 g (12.33 mmol) of the gadolinium complex of 10-[2-hydroxy-3-amino-propyl]-1,4,7-tris(carboxymethyl)-1,4,7,10-tetraazacyclododecane, dissolved in 30 ml of water, is added and stirred for 3 hours at room temperature. It is evaporated to dryness, the residue is taken up in a mixture of 100 ml of methanol/50 ml of chloroform, and dicyclohexylurea is filtered out. The filtrate is evaporated to dryness and purified by RP-chromatography (RP-18/mobile solvent: gradient consisting of water/n-propanol/acetonitrile).

Yield: 17.76 g (78% of theory) of a colorless, vitreous solid

Water content: 6.8%

Elementary analysis (relative to anhydrous substance):

Cld: C, 31.08; H, 3.03; F, 34.12; Gd, 8.31; N, 7.40; S, 3.39. Fnd: C, 30.89; H, 3.15; F, 34.01; Gd, 8.14; N, 7.25; S, 3.24.

EXAMPLE 16

Gadolinium complex of 1,4,7-tris(carboxylatomethyl)-10-(2-hydroxy-19,19,20,20,21,21,22,22,23,23,24,24,25,25,26,26,26-heptadecafluoro-4,7,10,13,16-penta-oxa-hexacosane)-1,4,7,10-tetraazacyclododecane a) 16,16,17,17,18,18,19,19,20,20,21,21,22,22,22-Heptadecafluoro-3,6,9,12-tetra-oxa-docosan-1-ol A mixture of 20 g (32.35 mmol) of 1-p-toluenesulfonyloxy-1H,1H,2H,2H-perfluorodecane [see Example 7a], 1 g of tetrabutylammonium hydrogen sulfate, 62.83 g (323.5 mmol) of tetraethylene glycol, 300 ml of dichloromethane and 100 ml of 50% sodium hydroxide solution is stirred intensively at about 5° C. for 24 hours. It is then diluted with 200 ml of dichloromethane, the phases are separated, and the dichloromethane phase is washed with water. The organic phase is dried on magnesium sulfate and concentrated by evaporation in a vacuum. 18.5 g of the desired title compound is obtained as light yellow oil.

b) 1,2-Epoxy-19,19,20,20,21,21,22,22,23,23,24,24,25,25,26,26,26-heptadecafluoro-4,7,10,13,16-penta-oxa-hexacosane A mixture of 17 g (26.5 mmol) of 16,16,17,17,18,18,19,19,20,20,21,21,22,22,22-heptadecafluoro-3,6,9,12-tetra-oxa-docosan-1-ol, 0.5 g of tetrabutylammonium hydrogen sulfate, 2.94 g of epichlorohydrin, 200 ml of dichloromethane and 50 ml of 50% sodium hydroxide solution is stirred intensively at room temperature for 8 hours. The phases are separated, the aqueous phase is shaken with 100 ml of dichloromethane, the organic phases are combined, shaken with 50 ml of water, dried on magnesium sulfate and concentrated by evaporation in a vacuum. The residue is chromatographed on silica gel with hexane/5-50% ethyl acetate, and 12.92 g of the title compound is obtained as oil.

Elementary analysis:

Cld: C, 36.22; H, 3.62; F, 46.38. Fnd: C, 36.00; H, 3.78; F, 46.20.

c) 1,4,7-Tris(carboxylatomethyl)-10-(2-hydroxy-19,19,20,20,21,21,22,22,23,23,24,24,25,25,26,26,26-heptadecafluoro-4,7,10,13,16-penta-oxa-hexacosane)-1,4,7,10-tetraazacyclododecane A solution of 12.05 g (17.3 mmol) of 1,2-epoxy-19,19,20,20,21,21,22,22,23,23,24,24,25,25,26,26,26-heptadecafluoro-4,7,10,13,16-penta-oxa-hexacosane in 50 ml of tetrahydrofuran is added to a solution of 6 g (17.3 mmol) of 1,4,7-(triscarboxylatomethyl)-1,4,7,10-tetraazacyclododecane and 4 g of sodium hydroxide in 30 ml of water. It is stirred overnight at 70° C., then largely concentrated by evaporation in a vacuum, the residue is taken up in 150 ml of water and adjusted to pH 3 with 6N hydrochloric acid and extracted several times with n-butanol. The combined extracts are concentrated by evaporation in a vacuum, and the residue is purified by chromatography on RP-18 with a gradient consisting of water/n-butanol/acetonitrile. 13.71 g of the title compound is obtained as yellow viscous oil.

Elementary analysis:

Cld: C, 40.31; H, 4.93; F, 30.97; N, 5.37. Fnd: C, 40.08; H, 5.21; F, 30.77; N, 5.29.

d) Gadolinium complex of 1,4,7-tris(carboxylatomethyl)-10-(2-hydroxy-19,19,20,20,21,21,22,22,23,23,24,24,25,25,26,26,26-heptadecafluoro-4,7,10,13,16-penta-oxa-hexacosane)-1,4,7,10-tetraazacyclododecane A mixture of 5 g (4.79 mmol) of 1,4,7-tris(carboxylatomethyl)-10-(2-hydroxy-19,19,20,20,21,21,22,22,23,23,24,24,25,25,26,26,26-heptadecafluoro-4,7,10,13,16-penta-oxa-hexacosane)-1,4,7,10-tetraazacyclododecane, 50 ml of water and 30 ml of ethanol is mixed with 869 mg (2.397 mmol) of gadolinium oxide, and it is refluxed for 5 hours. The hot solution is filtered and concentrated by evaporation in a vacuum. 5.60 g of the title compound is obtained as a vitreous, solid substance with a water content of 4.1%.

Elementary analysis (relative to anhydrous substance):
Cld: C, 35.12; H, 4.04; F, 26.98; Gd, 13.14; N, 4.68. Fnd: C, 34.90; H, 4.38; F, 26.70; Gd, 13.10; N, 4.62.

EXAMPLE 17

Gadolinium complex of 1,4,7-tris(carboxylatomethyl)-10-(4-aza-2-hydroxy-26,26,26,25,25,24,24,23,23,22,22,21,21,20,20,19,19-heptadecafluoro-5-oxo-16-thia-hexacosyl)-1,4,7,10-tetraazacyclododecane a) 22,22,22,21,21,20,20,19,19,18,18,17,17,16,16,15,15-Heptadecafluoro-12-thia-docosanoic acid A solution of 10 g (37.71 mmol) of 11-bromoundecanoic acid in 150 ml of dichloromethane is mixed with 11.43 g of triethylamine and 18.11 g (37.71 mmol) of 1H,1H,2H,2H-perfluorodecylmercaptan, and it is stirred overnight at room temperature. The solution is extracted several times with 2N hydrochloric acid, washed with common salt solution, dried on magnesium sulfate and concentrated by evaporation in a vacuum. 21.5 g of the title compound is obtained as yellow oil.

Elementary analysis:
Cld: C, 37.96; H, 3.79; F, 48.61; S, 4.83. Fnd: C, 38.30; H, 4.01; F, 48.40; S, 5.20.

b) Gadolinium complex of 1,4,7-tris(carboxylatomethyl)-10-(4-aza-2-hydroxy-26,26,26,25,25,24,24,23,23,22,22,21,21,20,20,19,19-heptadecafluoro-5-oxo-16-thia-hexacosyl)-1,4,7,10-tetraazacyclododecane 5 g (7.52 mmol) of the title compound of Example 17a) and 0.95 g of N-hydroxysuccinimide are dissolved in a mixture of 25 ml of dimethylformamide and 15 ml of chloroform. 1.71 g of dicyclohexylcarbodiimide is added at 0° C. and stirred for 1 hour at 0° C., then for 3 hours at room temperature. It is then cooled again to 0° C. and mixed with 3 ml of triethylamine and 20 ml of n-propanol. Then, 4.75 g (8.27 mmol) of the gadolinium complex of 10-(3-amino-2-hydroxy-propyl)-1,4,7-tris(carboxylatomethyl)-1,4,7,10-tetraazacyclododecane, dissolved in 25 ml of water, is added and stirred for 3 hours at 20° C. It is evaporated to dryness, the residue is taken up in a mixture of 55 ml of methanol and 20 ml of chloroform, and dicyclohexylurea is filtered out. The filtrate is evaporated to dryness and purified by chromatography on RP-18 with a gradient consisting of water/n-propanol/acetonitrile. 6.15 g of the title compound is obtained as a vitreous solid, with a water content of 2.3%.

Elementary analysis (relative to anhydrous substance):
Cld: C, 37.41; H, 4.38; F, 26.47; Gd, 12.89; N, 5.74; S, 2.63. Fnd: C, 37.08; H, 4.60; F, 26.30; Gd, 12.68; N, 5.91; S, 2.49.

EXAMPLE 18

Gadolinium complex of 1,4,7-tris(carboxylatomethyl)-10-[1-(1,2-dihydroxyethyl)3-oxa-6,6,7,7,8,8,9,9,10,10,11,11,11-tridecafluoro]undecane-1,4,7,10-tetraazacyclododecane a) 1-p-Toluenesulfonyloxy-1H,1H,2H,2H-perfluorooctane 20 ml of pyridine is added to a solution of 25 g (68.7 mmol) of 1H,1H,2H,2H-perfluorooctan-1-ol in 300 ml of dichloromethane at 0° C., and 13.49 g (70.76 mmol) of p-toluenesulfonic acid chloride is added in portions while being stirred. It is stirred for 3 more hours at 0° C., and the dichloromethane is drawn off at room temperature in a vacuum. The remaining pyridine solution is mixed with ice water, whereby the desired product precipitates. The residue is decanted and dissolved in dichloromethane, the solution is washed with water, dried on magnesium sulfate and concentrated by evaporation in a vacuum. The residue is purified by chromatography on silica gel with hexane/5-40% ethyl acetate. 29.2 g of the title compound is obtained as viscous foam.

Elementary analysis:
Cld: C, 34.76; H, 2.14; F, 47.65; S, 6.19. Fnd: C, 34.98; H, 2.38; F, 47.39; S, 6.42.

b) 1,4,7-Tris(benzyloxycarbonyl)-10-[1-(2,2-dimethyl-1,3-dioxolan-4-yl)-6,6,7,7,8,8,9,9,10,10,11,11,11-tridecafluoro-3-oxa]-undecane-1,4,7,10-tetraazacyclododecane 20 ml of 50% sodium hydroxide solution, 0.5 g of tetrabutylammonium hydrogen sulfate and 5.18 g (10 mmol) of 1-p-toluenesulfonyloxy-1H,1H,2H,2H-perfluorooctane [see Example 18a)] are added in succession to 7.33 g (10 mmol) of 1,4,7-tris(benzyloxycarbonyl)-10-[2-hydroxy-1-(2,2-dimethyl-1,3-dioxolan-4-yl)-ethyl-1,4,7,10-tetraazacyclododecane [J. Mag. Res. Imag. 5, 7-10, (1955)], dissolved in 100 ml of dichloromethane, and the mixture is stirred intensively overnight at room temperature. The phases are separated, the organic phase is washed several times with water, dried on magnesium sulfate and concentrated by evaporation in a vacuum. The residue is purified by chromatography on silica gel with dichloromethane/1-10% ethanol. 8.02 g of the title compound is obtained as viscous oil.

Elementary analysis:
Cld: C, 53.01; H, 5.02; F, 23.19; N, 5.26. Fnd: C, 53.30; H, 5.39; F, 23.01; N, 5.40.

c) 1-[1-(2,2-Dimethyl-1,3-dioxolan-4-yl)-6,6,7,7,8,8,9,9,10,10,11,11,11-tridecafluoro-3-oxa]-undecane-1,4,7,10-tetraazacyclododecane A solution of 7 g (6.57 mmol) of 1,4,7-tris(benzyloxycarbonyl)-10-[1-(2,2-dimethyl-1,3-dioxolan-4-yl)-6,6,7,7,8,8,9,9,10,10,11,11,11-tridecafluoro-3-oxa]-undecane-1,4,7,10-tetraazacyclododecane in 100 ml of isopropyl alcohol is mixed with 0.7 g of palladium on carbon (10%), and it is shaken for 3 hours under hydrogen atmosphere. Catalyst is filtered out, and the solution is concentrated by evaporation in a vacuum. 4.20 g of the title compound is obtained as vitreous foam.

Elementary analysis:
Cld: C, 41.70; H, 5.32; F, 37.28; N, 8.46. Fnd: C, 41.61; H, 5.57; F, 37.10; N, 8.59.

d) 1,4,7-Tris(carboxylatomethyl)-10-[1-(1,2-dihydroxy-ethyl)-3-oxa-6,6,7,7,8,8,9,9,10,10,11,11,11-tridecafluoro]undecane-1,4,7,10-tetraazacyclododecane 3.36 g (24.15 mmol) of bromoacetic acid in 50 ml of water is dissolved and mixed with 6N sodium hydroxide solution until pH 7 is reached. A solution of 4 g (6.04 mmol) of 1-[1-(2,2-dimethyl-1,3-dioxolan-4-yl)-6,6,7,7,8,8,9,9,10,10,11,11,11-tridecafluoro-3-oxa]-undecane-1,4,7,10-tetraazacyclododecane, dissolved in 20 ml of isopropyl alcohol, and enough 6N sodium hydroxide solution are added in drops at 40° C. while simultaneously being stirred so that the pH is kept at 9-10. Then, it is mixed with semiconcentrated hydrochloric acid up to pH 1 and stirred for another 3 hours at 60° C. It is cooled to room temperature, and the solution is extracted several times with n-butanol. The organic extract is concentrated by evaporation, and the residue is purified by chromatography on RP-18 with a gradient consisting of water/n-butanol/acetonitrile. 3.85 g of the title compound is obtained as yellow oil with a water content of 3.9%.

Elementary analysis (relative to anhydrous substance):
Cld: C, 39.20; H, 4.68; F, 31.00; N, 7.03. Fnd: C, 39.08; H, 4.98; F, 30.72; N, 7.29.

e) Gadolinium complex of 1,4,7-tris(carboxylatomethyl)-10-[1-(1,2-dihydroxy-ethyl)-3-oxa-6,6,7,7,8,8,9,9,10,10,11,11,11-tridecafluoro]undecane-1,4,7,10-tetraazacyclododecane A mixture of 1.59 g (2 mmol) of 1,4,7-tris(carboxylatomethyl)-10-[1-(1,2-dihydroxy-ethyl)-3-oxa-6,6,7,7,8,8,9,9,10,10,11,11,11-tridecafluoro]undecane-1,4,7,10-tetraazacyclododecane, 25 ml of water and 15 ml of ethanol is mixed with 363 mg (1 mmol) of gadolinium oxide, and it is refluxed for 5 hours. The hot solution is filtered, concentrated by evaporation in a vacuum, and 1.85 g of the title compound is obtained as a vitreous, solid substance with a water content of 4.2%.

Elementary analysis (relative to anhydrous substance):
Cld: C, 32.84; H, 3.60; F, 25.98; Gd, 16.54; N, 5.89. Fnd: C, 32.53; H, 3.71; F, 25.72; Gd, 16.39; N, 5.93.

EXAMPLE 19

Gadolinium complex of 1,4,7-tris(carboxylatomethyl)-10-{2-hydroxy-4-oxa-4-[4-(2H,2H,3H,3H-1-oxa-perfluoroundec-1-yl)]-phenyl}-but-1-yl-1,4,7,10-tetraazacyclododecane a) 1-Hydroxy-4-(2H,2H,3H,3H-1-oxa-perfluoroundec-1-yl)-benzene 5 g (45.41 mmol) of hydroquinone is mixed with 100 ml of acetone and mixed while being stirred in succession with 13.8 g of potassium carbonate and 14.04 g (22.7 mmol) of 1-p-toluenesulfonyloxy-1H,1H,2H,2H-perfluorodecane [see Example 7a)]. It is refluxed for 6 hours, then largely concentrated by evaporation in a vacuum, diluted with 200 ml of water, adjusted to pH 3 with citric acid and extracted several times with dichloromethane. The organic extract is dried on magnesium sulfate and concentrated by evaporation in a vacuum. The residue is purified by chromatography on silica gel with hexane/5-30% ethyl acetate. 8.20 g of the desired title compound is obtained as viscous oil.

Elementary analysis:
Cld: C, 34.55; H, 1.63; F, 58.07. Fnd: C, 34.31; H, 1.79; F, 58.01.

b) 1-(3,4-Epoxy-1-oxa-but-1-yl)-4-(2H,2H,3H,3H-1-oxa-perfluoroundec-1-yl)-benzene A mixture of 8 g (14.38 mmol) of 1-hydroxy-4-(2H,2H,3H,3H-1-oxa-perfluoroundec-1-yl)-benzene, 0.4 g of tetrabutylammonium hydrogen sulfate, 1.60 g (17.26 mmol) of epichlorohydrin, 150 ml of dichloromethane and 30 ml of 50% sodium hydroxide solution is stirred intensively for 30 minutes in an ice bath, then for 5 hours at room temperature. The phases are separated, the organic phase is washed with water, dried on magnesium sulfate and concentrated by evaporation in a vacuum. The residue is purified by chromatography on silica gel with hexane/5-30% ethyl acetate, and 6.60 g of the title compound is obtained as viscous oil.

Elementary analysis:
Cld: C, 37.27; H, 2.41; F, 52.75. Fnd: C, 37.10; H, 2.66; F, 52.80.

c) 1,4,7-Tris(carboxylatomethyl)-10-{2-hydroxy-4-oxa-4-(4-(2H,2H,3H,3H-1-oxa-perfluoroundec-1-yl)]-phenyl}-but-1-yl-1,4,7,10-tetraazacyclododecane A solution of 6.12 g (10 mmol) of 1-(3,4-epoxy-1-oxa-but-1-yl)-4-(2H,2H,3H,3H-1-oxa-perfluoroundec-1-yl)-benzene in 25 ml of tetrahydrofuran is added to a solution of 3.46 g (10 mmol) of 1,4,7-tris(carboxylatomethyl)-1,4,7,10-tetraazacyclododecane and 2.5 g of sodium hydroxide in 25 ml of water, and it is refluxed for 24 hours, then largely concentrated by evaporation in a vacuum, the residue is dissolved in 100 ml of water, adjusted to pH 3 with 6N hydrochloric acid and extracted several times with n-butanol. The combined extracts are concentrated by evaporation in a vacuum. The residue is purified by chromatography on RP-18 with a gradient consisting of water/n-butanol/acetonitrile. 6.71 g of the title compound is obtained as viscous oil.

Elementary analysis:
Cld: C, 41.35; H, 4.10; F, 33.69; N, 5.84. Fnd: C, 41.58; H, 4.38; F, 33.50; N, 5.91.

d) Gadolinium complex of 1,4,7-tris(carboxylatomethyl)-10-{2-hydroxy-4-oxa-4-[4-(2H,2H,3H,3H-1-oxa-perfluoroundec-1-yl)]-phenyl}-but-1-yl-1,4,7,10-tetraazacyclododecane A mixture of 4.79 g (5 mmol) of 1,4,7-tris(carboxylatomethyl)-10-{2-hydroxy-4-oxa-4-[4-(2H,2H,3H,3H-1-oxa-perfluoroundec-1-yl)]-phenyl}-but-1-yl-1,4,7,10-tetraazacyclododecane, 50 ml of water and 30 ml of ethanol is mixed with 906 mg (2.5 mmol) of gadolinium oxide and refluxed for 5 hours. The hot solution is filtered and concentrated by evaporation in a vacuum. 5.50 g of the title compound is obtained as a vitreous solid substance with a water content of 4.9%.

Elementary analysis (relative to anhydrous substance):
Cld: C, 35.62; H, 3.26; F, 29.02; Gd, 14.13; N, 5.03. Fnd: C, 35.40; H, 3.50; F, 28.81; Gd, 14.01; N, 5.18.

EXAMPLE 20

Gadolinium complex, disodium salt of 3,9-bis(carboxymethyl)-6-[(1-carboxy)-1H,2H,2H,4H,4H,5H,5H-3-oxa-perfluorotridecyl]-3,6,9-triazaundecanedioic acid a) N-t-Butoxycarbonyl-serine-(1H,1H,2H,2H-perfluorodecyl)-ether-benzyl ester 300 mg (10 mmol) of sodium hydride (80% in oil) is added in portions to a solution of 2.953 g (10 mmol) of N-t-butyloxycarbonyl-serine-benzyl ester (Bachem commercially available products) in 30 ml of dry dimethylformamide. After dissolving is completed, it is mixed with 6.072 g (10 mmol) of the tosylate produced under 7a). It is stirred for 12 hours at room temperature. Then, it is poured into 500 ml of ice water, the product is taken up in dichloromethane, the organic solution is washed with water, dried on sodium sulfate and evaporated to dryness. The residue is purified by chromatography on silica gel. A mixture of dichloromethane with increasing addition of methanol is used as eluant.

The title compound is obtained as syrup.
Yield: 5.902 g (79.6% of theory)
Elementary analysis:
Cld: C, 40.50; H, 3.26; F, 43.56; N, 1.89. Fnd: C, 40.64; H, 3.37; F, 43.49; N, 1.83.

b) Serine-(1H,1H,2H,2H-perfluorodecyl)-ether-benzyl ester (as salt of trifluoroacetic acid 7.414 g (10 mmol) of the N-protected compound that is produced under 20a) is dissolved in 50 ml of a mixture of trifluoroacetic acid and dichloromethane at a 2:1 ratio, and it is stirred overnight at room temperature. It is evaporated to dryness, and the remainder of the trifluoroacetic acid is removed by codistillation with ethanol. The title compound is isolated as a salt of trifluoroacetic acid.

Yield: 7.418 g (98.2% of theory)
Elementary analysis:
Cld: C, 34.98; H, 2.27; F, 50.30; N, 1.85. Fnd: C, 34.89; H, 2.31; F, 50.39; N, 1.80.

c) 3,9-Bis(t-butoxycarbonylmethyl)-6-[(1-benzyloxycarbonyl)-1H,2H,2H,4H,4H,5H,5H-3-oxa-perfluorotridecyl)-3,6,9-triazaundecanedioic acid-di(t-butyl)-ester 3.777 g (5 mmol) of the amine-trifluoroacetate that is produced under 20b) and 3.523 g (10 mmol) of N,N-bis(t-butyloxycarbonylmethyl)-2-(bromoethyl)-amine are added to a mixture of 10 ml of acetonitrile and 20 ml of phosphate buffer of pH 8.0, and it is stirred intensively at room temperature for 2 hours. Then, the buffer phase is separated, extracted with 10 ml of acetonitrile, and the latter is added to the organic phase. After 20 ml of fresh buffer is added, it is stirred for 20 more hours at room temperature. The organic phase is separated, concentrated by evaporation, and the residue is dispersed between 100 ml of phosphate buffer (pH 8.0) and 100 ml of ethyl acetate. The organic phase is washed with saturated common salt solution, dried on sodium sulfate and concentrated by evaporation. The title compound is purified by chromatography on silica gel. Dichloromethane is used as eluant with increasing addition of methanol. The title compound is obtained as a glass-like solid.

Yield: 3.162 g (53.4% of theory)
Elementary analysis:
Cld: C, 48.69; H, 5.62; F, 27.28; N, 3.55. Fnd: C, 48.82; H, 5.72; F, 27.37; N, 3.50.

d) 3,9-Bis(carboxymethyl)-6-[(1-carboxy)-1H,2H,2H,4H,4H,5H,5H-3-oxa-perfluorotridecyl]-3,6,9-triazaundecanedioic acid 5.920 g (5 mmol) of the compound that is produced under 20c) is added to a mixture of 25 ml of trifluoroacetic acid/dichloromethane at a 2:1 ratio. It is allowed to stir overnight at room temperature, then evaporated to dryness, the residue is taken up in 100 ml of 3N hydrochloric acid, refluxed for 3 hours, then evaporated to dryness in a vacuum and taken up in 160 ml of a mixture of water, ethanol and chloroform (10:5:1). The solution is set at a constant pH (about 3) by adding ion exchanger IRA 67 (OH$^-$ form). It is quickly suctioned off, and the title compound is obtained as a vitreous solid.

Yield: 3.080 g (71.3% of theory)
Water content: 11.3%
Elementary analysis (relative to anhydrous substance):
Cld: C, 34.53; H, 3.25; F, 37.15; N, 4.83. Fnd: C, 34.41; H, 3.32; F, 37.29; N, 4.90.

e) Gadolinium complex, disodium salt of 3,9-bis(carboxymethyl)-6-[(1-carboxy)-1H,2H,2H,4H,4H,5H,5H-3-oxa-perfluorotridecyl]-3,6,9-triazaundecanedioic acid 2.941 g (3.0 mmol, relative to 11.3% water content) of the acid that is produced under 20d) is added to a mixture of 60 ml of distilled water and 30 ml of ethanol. 543.8 mg (1.5 mmol) of gadolinium oxide is added in portions while being stirred and heated to 50° C. After addition is completed, it is stirred until dissolved. The pH of the solution is then adjusted to 7.2 by adding sodium hydroxide solution. The solution is then concentrated by evaporation, whereby strong foaming can be observed. The residue is codistilled with distilled water. The title compound is obtained as a vitreous solid.

Yield: 3.489 g (quantitative)
Water content: 8.2%
Elementary analysis (relative to anhydrous substance):
Cld: C, 28.12; H, 2.17; F, 30.25; Gd, 14.73; N, 3.94; Na, 4.31. Fnd: C, 28.25; H, 2.26; F, 30.40; Gd, 14.85; N, 3.99; Na, 4.38.

EXAMPLE 21

Gadolinium complex, monosodium salt of 3,6,9-tris(carboxymethyl)-3,6,9-triazaundecanedioic acid-mono-N-{ethyl-2-amino-[carbonylmethyl-amino-(N-ethyl-N-perfluorooctylsulfonyl)]}-amide a) 3,6,9-Tris(carboxylatomethyl)-3,6,9-triazaundecanedioic acid-mono-N-{ethyl-2-amino-[carbonylmethyl-amino-(N-ethyl-N-perfluorooctylsulfonyl)]}-amide 17.87 g (50 mmol) of diethylenetriaminepentaacetic acid-bis-anhydride is suspended in 200 ml of a mixture of dimethylformamide and dichloromethane at a 4:1 ratio and mixed in portions with the mixture of 3.137 g (5 mmol) of [N-(2-aminoethyl)-N-perfluorooctylsulfonyl]-aminoacetic acid-N-(2-aminoethyl)-amide and 6.50 g (64.2 mmol) of triethylamine while being stirred vigorously. It is allowed to stir for 5 more hours, evaporated to dryness, mixed with 300 ml of ice water, and the pH of the batch is adjusted to about 3 with 3N hydrochloric acid. It is extracted twice with 200 ml of n-butanol each, the organic solutions are combined and concentrated by evaporation. The product is purified by chromatography on silica gel RP-18. Water and tetrahydrofuran are used as eluants. The title compound is obtained as a vitreous solid.

Yield: 2.722 g (54.3% of theory)

Water content: 9.7%

Elementary analysis (relative to anhydrous substance):

Cld: C, 33.54; H, 3.52; F, 32.21; N, 8.38; S, 3.20. Fnd: C, 33.65; H, 3.60; F, 32.14; N, 8.51; S, 3.29.

b) Gadolinium complex, monosodium salt of 3,6,9-tris(carboxymethyl)-3,6,9-triazaundecanedioic acid-mono-N-{ethyl-2-amino-[carbonylmethyl-amino-(N-ethyl-N-perfluorooctylsulfonyl)]}-amide 3.259 g (3 mmol, relative to 9.7% water) of the compound that is produced under 21a) is added to 90 ml of a mixture of distilled water and ethanol (2:1). While being stirred, 543.8 mg (1.5 mmol) of gadolinium oxide is added in portions. It is stirred until dissolved, then the pH of the solution is adjusted to 7.2 by adding sodium hydroxide solution, and it is concentrated by evaporation, whereby strong foaming occurs. The residue is codistilled with distilled water. The title compound is obtained as a glass-like solid.

Yield: 3.861 g (quantitative)

Water content: 8.4%

The elementary analysis is relative to anhydrous substance:

Cld: C, 28.53; H, 2.65; F, 27.40; Gd, 13.34; N, 7.13; Na, 1.95; S, 2.72. Fnd: C, 28.61; H, 2.68; F, 27.48; Gd, 13.40; N, 7.08; Na, 1.99; S, 2.76.

EXAMPLE 22

Gadolinium complex, monosodium salt of 3,9-bis (carboxymethyl)-6-1H,1H,4H,4H,5H,5H,8H,8H, 10H,10H,11H,11H-2,7-dioxo-3,6-diaza-9-oxa-perfluoromonodecyl)-3,6,9-triazaundecanedioic acid a) Glycolic acid-(1H,1H,2H,2H-perfluorodecyl)-ether-N-(2-aminoethyl)-amide 10.44 g (20 mmol) of compound 2b) is dissolved in 80 ml of dichloromethane and mixed with 2.30 g (20 mmol) of N-hydroxysuccinimide as well as 4.13 g (20 mmol) of dicyclohexylcarbodiimide. It is allowed to stir overnight, dicyclohexylurea is filtered out, and the filtrate is stirred in a solution of 60.1 g (1000 mmol) of ethylenediamine in 100 ml of dichloromethane. It is allowed to stir overnight, mixed with 1.5 l of water, and the organic phase is separated. The dichloromethane solution is washed with water, dried on sodium sulfate, evaporated to dryness and the residue is purified by chromatography on silica gel. A mixture of dichloromethane with increasing addition of isopropanol is used as eluant.

Yield: 9.615 g (85.2% of theory)

Elementary analysis:

Cld: C, 29.80; H, 2.32; F, 57.24; N, 4.96. Fnd: C, 29.96; H, 2.37; F, 57.12; N, 5.01.

b) Glycolic acid-(1H,1H,2H,2H-perfluorodecyl)-ether-N-[ethyl-2-(benzyloxycarbonyl-aminomethyl-carbonylamino)]-amide 2.092 g (10 mmol) of benzyloxycarbonylglycine is dissolved in 15 ml of dichloromethane and mixed with 1.151 g (10 mmol) of N-hydroxysuccinimide as well as 2.063 g (10 mmol) of dicyclohexylcarbodiimide. It is allowed to stir overnight, dicyclohexylurea is filtered out and evaporated to dryness. The residue is purified on silica gel by column chromatography. A mixture of dichloromethane and ethanol is used as eluant. The title compound is obtained as a vitreous solid.

Yield: 6.905 g (91.40% of theory)

Elementary analysis:

Cld: C, 38.16; H, 2.94; F, 42.75; N, 5.56. Fnd: C, 38.28; H, 2.98; F, 42.82; N, 5.50.

c) Glycolic acid-(1H,1H,2H,2H-perfluorodecyl)-ether-N-[ethyl-(2-aminomethyl-carboxylamino)-amide 3.777 g (5 mmol) of the compound that is produced under 22b) is hydrogenated in 100 ml of a mixture of tetrahydrofuran and ethanol at a 2:1 ratio in the presence of 0.2 g of Pearlman's catalyst (Pd 20%/C) until 112 ml of hydrogen is taken up. Catalyst is suctioned off, rewashed well with ethanol and evaporated to dryness. The title compound is obtained as a glass-like solid.

Yield: 3.097 g (99.7% of theory)

Elementary analysis:

Cld: C, 30.93; H, 2.60; F, 51.98; N, 6.76. Fnd: C, 30.87; H, 2.64; F, 52.11; N, 6.82.

d) 3,9-Bis(t-butyloxycarbonylmethyl)-6-(1H,1H,4H, 4H,5H,5H,8H,8H,10H,10H,11H,11H,-2,7-dioxo-3,6-diaza-9-oxa-perfluorononadecyl)3,6,9-triazaundecanedioic acid-bis(t-butylester)

3.107 g (5 mmol) of the amine that is produced under 22c) and 3.523 g (10 mmol) of N,N-bis(t-butyloxycarbonylmethyl)-2-(bromoethyl)-amine are added to a mixture of 10 ml of acetonitrile and 20 ml of phosphate buffer of pH 8 and stirred intensively for 2 hours at room temperature. Then, the buffer phase is separated, it is extracted with 10 ml of acetonitrile, and the latter is added to the organic phase. After 20 ml of fresh buffer is added, it is stirred for 20 more hours at room temperature. The organic phase is separated, it is concentrated by evaporation, and the residue is dispersed between 100 ml of phosphate buffer (pH 8.0) and 100 ml of ethyl acetate. The organic phase is washed with saturated common salt solution, dried on sodium sulfate and concentrated by evaporation. The compound is purified on silica gel by chromatography. Dichloromethane with increasing addition of methanol is used as eluant. The title compound is obtained as a glass-like solid.

Yield: 3.044 g (52.3% of theory)

Elementary analysis:

Cld: C, 45.40; H, 5.71; F, 27.75; N, 6.02. Fnd: C, 45.47; H, 5.78; F, 27.68; N, 6.10.

e) 3,9-Bis(carboxymethyl)-6-(1H,1H,4H,4H,5H,5H, 8H,8H,10H,10H,11H,11H-2,7-dioxo-3,6-diaza-9-oxa-perfluoromonodecyl)-3,6,9-triazaundecanedioic acid 5.820 g (5 mmol) of the compound that is produced under 22d) is added to a mixture of 120 ml of trifluoroacetic acid/dichloromethane at a 2:1 ratio. It is allowed to stir overnight at room temperature, evaporated to dryness, the remainder of trifluoroacetic acid is removed by codistillation with ethanol and taken up in 240 ml of a mixture of water, ethanol and chloroform. The solution is set at a constant pH (about 3) by adding ion exchanger IRA-67 (OH⁻ form). It is quickly suctioned off, concentrated by evaporation, and the title compound is obtained as a vitreous solid.

Yield: 3.214 g (68.4% of theory)
Water content: 10.3%
Elementary analysis (relative to anhydrous substance):
Cld: C, 35.79; H, 3.65; F, 34.37; N, 7.45. Fnd: C, 35.90; H, 3.72; F, 34.31; N, 7.51.

f) Gadolinium complex, monosodium salt of 3,9-bis(carboxymethyl)-6-(1H,1H,4H,4H,5H,5H,8H,8H, 10H,10H,11H,11H-2,7-dioxo-3,6-diaza-9-oxa-perfluorononadecyl)-3,6,9-triaza-undecanedioic acid 3.143 g (3.0 mmol, relative to 10.3% water content) of the acid that is produced under 22e) is added to a mixture of 60 ml of distilled water and 30 ml of ethanol. 543.8 mg (1.5 mmol) of gadolinium oxide is added in portions while being stirred and heated to 50° C. After addition is completed, it is stirred until dissolved. Then, the pH of the solution is adjusted to 7.2 by adding sodium hydroxide solution, the solution is concentrated by evaporation, whereby strong foaming can be observed. The residue is codistilled with distilled water. The title compound is obtained as a vitreous solid.

Yield: 3.635 g (quantitative)
Water content: 7.9%
Elementary analysis (relative to anhydrous substance):
Cld: C, 30.14; H, 2.71; F, 28.95; Gd, 14.09; N, 6.28; Na, 2.06. Fnd: C, 30.21; H, 2.78; F, 29.03; Gd, 14.16; N, 6.22; Na, 2.11.

EXAMPLE 23

Gadolinium complex of 3,6,9-tris(carboxymethyl)-3,6,9-triazaundecanedioic acid-bis{N-[2-aminoethyl-(N-ethyl-N-perfluorooctylsulfonyl]-amide} a) N-Ethyl-(2-benzyloxycarbonylamino-ethyl)-perfluorooctylsulfonic acid amide 5.272 g (10 mmol) of perfluorooctylsulfonic acid-N-ethylamide is dissolved in 30 ml of dimethylformamide. With exclusion of moisture, it is mixed with 330 mg (11 mmol) of sodium hydride (80% in oil). After gas generation is completed, the solution of 2.093 g (10 mmol) of N-benzyloxycarbonyl-aziridine is added dropwise to it. It is poured into 300 ml of ice water, extracted with dichloromethane, the organic solution is washed with water, it is dried on sodium sulfate and evaporated to dryness. The residue is chromatographed on silica gel with dichloromethane/methanol. The title compound is a glass-like solid.

Yield: 6.149 g (87.3% of theory)
Elementary analysis:
Cld: C, 34.10; H, 2.43; F, 45.85; N, 3.98; S, 4.55. Fnd: C, 34.00; H, 2.49; F, 45.97; N, 4.06; S, 4.49.

b) N-Ethyl-N-2-(aminoethyl)-perfluorooctylsulfonamide 3.522 g (5 mmol) of the compound that is produced under 23a) is hydrogenated in 100 ml of a mixture of tetrahydrofuran and ethanol at a 2:1 ratio in the presence of 0.2 g of Pearlman's catalyst (Pd 20%/C) until 112 ml of hydrogen is taken up. Catalyst is suctioned off, it is rewashed well with ethanol and evaporated to dryness. The title compound is obtained as an amorphous solid.

Yield: 2.814 g (98.7% of theory)
Elementary analysis:
Cld: C, 25.27; H, 1.94; F, 56.64; N, 4.91; S, 5.62. Fnd: C, 25.39; H, 1.99; F, 56.57; N, 4.96; S, 5.53.

c) 3,6,9-Tris(carboxymethyl)-3,6,9-triazaundecanedioic acid-bis{N-[2-aminoethyl-(N-ethyl-N-perfluorooctylsulfonyl)]-amide}

5.703 g (10 mmol) of the compound that is produced under 23b) as well as 1.518 g (15 mmol) of triethylamine are dissolved in 30 ml of dry dimethylformamide and mixed in portions with 1.787 g (5 mmol) of diethylenetriaminepentaacetic acid-bisanhydride while being stirred and with exclusion of moisture. It is allowed to stir overnight, then concentrated by evaporation, mixed with water, the pH is adjusted to about 3 with 3N hydrochloric acid, and it is extracted twice with 100 ml of n-butanol each. The organic solutions are combined, concentrated by evaporation and subjected to a chromatography on silica gel RP-18. Water and tetrahydrofuran are used as eluant. The title compound is obtained as a glass-like solid.

Yield: 6.172 g (82.4% of theory)
Water content: 9.8%
Elementary analysis (relative to anhydrous substance):
Cld: C, 30.47; H, 2.76; F, 43.12; N, 6.55; S, 4.28. Fnd: C, 30.59; H, 2.81; F, 43.00; N, 6.61; S, 4.33.

d) Gadolinium complex of 3,6,9-tris(carboxymethyl)-3,6,9-triazaundecanedioic acid-bis{N-[2-aminoethyl-(N-ethyl-N-perfluorooctylsulfonyl)]-amide}

6.570 g (4 mmol, relative to 9.8% water content) of the compound that is produced under 23c) is added to a mixture of 120 ml of distilled water, 60 ml of ethanol and 20 ml of chloroform. 725 mg (82.0 mmol) of gadolinium oxide is added in portions while being stirred and heated to 50° C. It is stirred until dissolved, then concentrated by evaporation, whereby strong foaming occurs, and the residue is subjected to codistillation with distilled water. The codistillation is repeated twice. The title compound is obtained as a glass-like solid.

Yield: 7.191 g (quantitative)
Water content: 8.1%
Elementary analysis (relative to anhydrous substance):
Cld: C, 27.63; H, 2.32; F, 39.10; Gd, 9.52; N, 5.93; S, 3.88. Fnd: C, 27.50; H, 2.37; F, 39.22; Gd, 9.61; N, 5.85; S, 3.95.

EXAMPLE 24

Gadolinium complex of 3,6,9-tris(carboxymethyl)-3,6,9-triazaundecanedioic acid-bis{N-<2-aminoethyl-[glycolic acid-(1H,1H,2H,2H-perfluorodecyl-ether)-amide]>-amide} a) 3,6,9-Tris(carboxymethyl)-3,6,9-triazaundecanedioic acid-bis{N-<2-aminoethyl-glycolic acid-(1H,1H,2H,2H-perfluorodecyl-ether)-amide]>-amide}

6.771 g (12 mmol) of the compound that is produced under Example 22a) as well as 1.821 g (18 mmol) of triethylamine are dissolved in 40 ml of dry dimethylformamide and mixed in portions with 2.144 g (6 mmol) of diethylenetriaminepentaacetic acid-bisanhydride while being stirred and with exclusion of moisture. It is allowed to stir overnight, then concentrated by evaporation, mixed with 20 ml of water, the pH is adjusted to about 3, and it is extracted with 3N hydrochloric acid twice with 150 ml of butanol each. The organic solutions are combined, concentrated by evaporation, and the residue is subjected to a chromatography on silica gel RP-18. Water and tetrahydrofuran are used as eluant. The title compound is obtained as a glass-like solid.
Yield: 6.989 g (78.4% of theory)
Water content: 7.1%
Elementary analysis (relative to anhydrous substance):
Cld: C, 33.95; H, 3.05; F, 43.47; N, 6.60. Fnd: C, 34.06; H, 3.11; F, 43.40; N, 6.67.

b) Gadolinium complex of 3,6,9-tris(carboxymethyl)-3,6,9-triazaundecanedioic acid-bis{N-<2-aminoethyl-[glycolic acid-(1H,1H,2H,2H-perfluorodecyl-ether) -amide]>-amide}

4.798 g (3 mmol, relative to 7.1% water) of the compound that is produced under 24a) is added to a mixture of 100 ml of distilled water, 50 ml of ethanol and 20 ml of chloroform. 543.8 mg (1.5 mmol) of gadolinium oxide is added in portions while being stirred and heated to 50° C. It is stirred until dissolved, then concentrated by evaporation, whereby strong foaming occurs. The residue is codistilled several times with distilled water. The title compound is obtained as a glass-like solid.
Yield: 5.285 g (quantitative)
Water content: 6.9%
The elementary analysis is relative to anhydrous substance.
Cld: C, 30.76; H, 2.58; F, 39.39; Gd, 9.59; N, 5.98. Fnd: C, 30.87; H, 2.65; F, 39.51; Gd, 9.69; N, 6.11.

EXAMPLE 25

Gadolinium complex, sodium salt of 3,9-bis(carboxymethyl)-6-[N-(1H,1H,2H,2H-perfluorodecyl)-aminocarbonylmethyl-3,6,9-triazaundecanedioic acid a) N-Benzyloxycarbonylglycine-N-(1H,1H,2H,2H-perfluorodecyl)-amide 7.877 g (15 mmol) of 1H,1H,2H,2H-perfluorodecylamine (J. Fluor. Chem. 55, 85 (1991)) is dissolved in 70 ml of dichloromethane and mixed with 1.726 g (15 mmol) of N-hydroxysuccinimide, 3.095 g (15 mmol) of dicyclohexylcarbodiimide and 3.138 g (15 mmol) of N-benzyloxycarbonylglycine (commercially available products, Bachem). It is allowed to stir overnight, the dicyclohexylurea is filtered off, concentrated by evaporation, and the residue is subjected to column chromatography on silica gel. Mixtures of dichloromethane and ethanol are used as eluant. The title compound is obtained as a solid.
Yield: 8.951 g (91.2% of theory)
Elementary analysis:
Cld: C, 36.71; H, 2.31; F, 49.36; N, 4.28. Fnd: C, 36.87; H, 2.39; F, 49.51; N, 4.37.

b) Glycine-N-(1H,1H,2H,2H-perfluorodecyl)-amide 7.594 g (10 mmol) of the compound that is produced under 28a) is dissolved in 150 ml of a mixture of tetrahydrofuran and ethanol at a 2:1 ratio and hydrogenated in the presence of 0.25 g of Pearlman's catalyst (Pd 20%/C) until 224 ml of hydrogen is taken up. Catalyst is suctioned out, rewashed well with ethanol and evaporated to dryness. The title compound is obtained as an amorphous solid.
Yield: 6.21 g (99.3% of theory)
Elementary analysis:
Cld: C, 25.37; H, 1.60; F, 56.84; N, 4.93. Fnd: C, 25.28; H, 1.65; F, 56.92; N, 4.99.

c) 3,9-Bis(t-butyloxycarbonylmethyl)-6-N-[1H,1H,2H,2H-perfluorodecyl)-aminocarbonylmethyl-3,6,9-triazaundecanedioic acid-di(t-butylester)

2.841 g (5 mmol) of the amine that is produced under 25b) and 3.875 g (11 mmol) of N,N-bis(t-butyloxycarbonylmethyl)-2-(bromoethyl)-amine are added to a mixture of 10 ml of acetonitrile and 20 ml of phosphate buffer of pH 8.0, and it is stirred intensively at room temperature for 2 hours. Then, the buffer phase is separated, it is extracted with 10 ml of acetonitrile, and the latter is added to the organic phase. After 20 ml of fresh buffer is added, it is stirred for 20 more hours at room temperature. The organic phase is separated, concentrated by evaporation, and the residue is dispersed between 100 ml of phosphate buffer (pH 8.0) and 100 ml of ethyl acetate. The organic phase is washed with saturated common salt solution, dried on sodium sulfate and concentrated by evaporation. The title compound is purified by chromatography on silica gel. Dichloromethane with increasing addition of methanol is used as eluant. The title compound is obtained as a glass-like solid.
Yield: 4.161 g (78.3% of theory)
Elementary analysis:
Cld: C, 45.20; H, 5.59; F, 30.39; N, 5.27. Fnd: C, 45.35; H, 5.67; F, 30.47; N, 5.34.

d) 3,9-Bis(carboxymethyl)-6-N-(1H,1H,2H,2H-perfluorodecyl)-aminocarbonylmethyl-3,6,9-triazaundecanedioic acid 4.783 g (4.5 mmol) of the compound that is produced under 25c) is added to a mixture of 100 ml of trifluoroacetic acid/dichloromethane at a 2:1 ratio. It is allowed to stir overnight at room temperature, then evaporated to dryness, the remainder of trifluoroacetic acid is removed by codistillation with ethanol and taken up in 160 ml of a mixture of water, ethanol and chloroform (10:5:1). A pH of about 3 (pH constant) is set by adding ion exchanger IRA-67 (OH⁻ form). It is suctioned off quickly, concentrated by evaporation, and the title compound is obtained as a vitreous solid.

Yield: 3.007 g (79.7% of theory)
Water content: 10.9%
Elementary analysis (relative to anhydrous substance):
Cld: C, 34.38; H, 3.25; F, 38.52; N, 6.68. Fnd: C, 34.29; H, 3.33; F, 38.65; N, 6.77.

e) Gadolinium complex, monosodium salt of 3,9-bis(carboxymethyl)-6-N-(1H,1H,2H,2H-perfluorodecyl)-aminocarbonylmethyl)-3,6,9-triazaundecanedioic acid 2.823 g (3.0 mmol, relative to 10.9% water content) of the acid that is produced under Example 25d) is added to a mixture of 60 ml of distilled water and 30 ml of ethanol. 543.8 mg (1.5 mmol) of gadolinium oxide is added in portions while being stirred and heated to 50° C. After addition is completed, it is stirred until dissolved. Then, the pH of the solution is adjusted to 7.2 by adding sodium hydroxide solution. The solution is concentrated by evaporation. In this case, strong foaming occurs. The residue is codistilled twice with distilled water. The title compound is obtained as a vitreous solid.
Yield: 3.353 g (quant)
Water content: 9.2%
The elementary analysis is relative to anhydrous substance.
Cld: C, 28.41; H, 2.28; F, 31.83; Gd, 15.50; N, 5.52; Na, 2.27. Fnd: C, 28.51; H, 2.33; F, 31.76; Gd, 15.57; N, 5.46; Na, 2.35.

EXAMPLE 26

Gadolinium complex, disodium salt of 3,6,9-tris(carboxymethyl)-4-[N-1H,1H,2H,2H-perfluorodecyloxy)-benzyl]-3,6,9-triazaundecanedioic acid a) 3,6,9-Tris-(t-butyloxycarbonylmethyl)-4-[4-(1H,1H,2H,2H-perfluorodecyloxy)-benzyl]-3,6,9-triazaundecanedioic acid-di(t-butylester)

6.131 g (5 mmol) of 3,6,9-tris(t-butyloxycarbonylmethyl)-4-(4-hydroxybenzyl)-3,6,9-triazaundecanedioic acid-di(t-butylester), produced according to PCT WO 88/07521, is added to 50 ml of dry dimethylformamide, and it is mixed in portions with 150 g (5 mmol) of sodium hydride (80% in oil) while being stirred and with exclusion of moisture. After dissolving is completed, it is mixed with 3.092 g (5 mmol) of the tosylate that is produced under Example 7a). It is stirred for 12 hours at 40° C. Then, it is poured into 500 ml of ice water, the product is taken up in dichloromethane, the organic solution is washed with water, dried on sodium sulfate and evaporated to dryness. The residue is purified by chromatography on silica gel. A mixture of dichloromethane, isopropanol, hexane at a 20:1:5 ratio is used as eluant.
The title compound is obtained as an amorphous solid.
Yield: 5.015 g (81.8% of theory)
Elementary analysis:
Cld: C, 49.96; H, 5.92; F, 26.34; N, 3.43. Fnd: C, 50.11; H, 6.00; F, 26.43; N, 3.38.

b) 3,6,9-Tris(carboxymethyl)-4-[4-(1H,1H,2H,2H-perfluorodecyloxy)-benzyl]-3,6,9-triazaundecanedioic acid 3.678 g (3 mmol) of the compound that is produced under Example 26a) is dissolved in 100 ml of a mixture of trifluoroacetic acid and dichloromethane at a 2:1 ratio, and it is stirred overnight at room temperature. It is evaporated to dryness, and the remainder of trifluoroacetic acid is removed by codistillation with ethanol. The residue is taken up in 160 ml of a mixture of water, ethanol and chloroform (10:5:1). By adding ion exchanger IRA-67 (OH⁻ form), a pH of about 3 (constant pH) is set. It is quickly suctioned off, concentrated by evaporation, and the title compound is obtained as a vitreous solid.
Yield: 2.357 g (83.1% of theory)
Water content: 11.3%
The elementary analysis is relative to anhydrous substance.
Cld: C, 39.38; H, 3.41; F, 34.16; N, 4.44. Fnd: C, 39.52; H, 3.47; F, 34.32; N, 4.36.

c) Gadolinium complex, disodium salt of 3,6,9-tris(carboxymethyl)-4-[N-(1H,1H,2H,2H-perfluorodecyloxy)-benzyl]-3,6,9-triazaundecanedioic acid 3.145 g (3.0 mmol, relative to 11.3% water content) of the acid that is produced under Example 26b) is added to a mixture of 60 ml of distilled water and 30 ml of ethanol. 543.8 mg (1.5 mmol) of gadolinium oxide is added in portions while being stirred and heated to 50° C. After addition is completed, it is stirred until dissolved. Then, the pH of the solution is adjusted to 7.2 by adding sodium hydroxide solution, and it is concentrated by evaporation. In this case, strong foaming occurs. The residue is codistilled twice with distilled water. The title compound is obtained as a vitreous solid.
Yield: 3.804 g (quantitative)
Water content: 9.8%
Elementary analysis (relative to anhydrous substance):
Cld: C, 32.55; H, 2.38; F, 28.24; Gd, 13.75; N, 3.67; Na, 4.02. Fnd: C, 32.44; H, 2.43; F, 28.30; Gd, 13.66; N, 3.71; Na, 4.10.

EXAMPLE 27

Gadolinium complex of 10-[(-perfluorooctyl-sulfonyl)-piperazin-1-yl-carbonylmethyl]-1,4,7-tris(carboxymethyl)-1,4,7,10-tetraazacyclododecane a) 1-Perfluorooctylsulfonyl-piperazine 34.39 g (398.3 mmol) of piperazine, 50 g (99.6 mmol) of perfluorooctylsulfonyl fluoride and 10.12 g (100 mmol) of triethylamine are heated for 24 hours to 85° C. 500 ml of water is added, and it is extracted twice with 200 ml of dichloromethane each. The organic phase is dried on magnesium sulfate and evaporated to dryness in a vacuum. The residue is chromatographed on silica gel (mobile solvent: dichloromethane/2-propanol=25:1).
Yield: 17.55 g (31% of theory) of a colorless, amorphous solid
Elementary analysis:
Cld: C, 25.36; H, 1.60; F, 56.84; N, 4.93; S, 5.64. Fnd: C, 25.15; H, 1.80; F, 56.65; N, 4.81; S, 5.70.

b) 1-(2-Bromoacetyl)-4-perfluorooctylsulfonyl-piperazine 17 g (29.9 mmol) of the title compound of Example 27a) and 5.1 g (50 mmol) of triethylamine are dissolved in 100 ml of dichloromethane. 9.1 g (44.9 mmol) of bromoacetyl bromide is added in drops at −10° C. within 30 minutes, and it is stirred for 2 hours at 0° C. The solution is poured into 200 ml of 2N hydrochloric acid and stirred well. The organic phase is separated, dried on magnesium sulfate and concentrated by evaporation in a vacuum. The residue is chromatographed on silica gel (mobile solvent: dichloromethane/acetone=20/1).

Yield: 18.55 g (90% of theory) of a slightly yellow-colored waxy solid

Elementary analysis:

Cld: C, 24.40; H, 1.46; F, 46.86; N, 4.06; S, 4.65; Br, 11.59. Fnd: C, 24.22; H, 1.60; F, 46.75; N, 3.97; S, 4.48; Br, 11.41.

c) 10-[(-Perfluorooctyl-sulfonyl)-piperazin-1-yl-carbonylmethyl]-1,4,7-tris(carboxymethyl)-1,4,7,10-tetraazacyclododecane 4.63 g (13.36 mmol) of 1,4,7-tris(carboxymethyl)-1,4,7,10-tetraazacyclododecane (≙D03A) and 18.5 g (133.6 mmol) of potassium carbonate are added to 17.78 g (20 mmol) of the title compound of Example 27b) in 180 ml of methanol. It is refluxed for 12 hours. The inorganic salts are filtered off, and the filtrate is evaporated to dryness. The residue is taken up in, 100 ml of water and adjusted to pH 3 with 5N hydrochloric acid. It is extracted twice with 150 ml of n-butanol. The combined organic phases are evaporated to dryness in a vacuum, and the residue is purified by RP-chromatography (RP-18/mobile solvent=gradient consisting of water/n-butanol/acetonitrile).

Yield: 12.79 g (67% of theory) of a colorless solid
Water content: 8.5%
Elementary analysis (relative to anhydrous substance):
Cld: C, 35.23; H, 3.70; F, 33.83; N, 8.80; S, 3.36. Fnd: C, 35.17; H, 3.81; F, 33.67; N, 8.65; S, 3.18.

d) Gadolinium complex of 10-[(-perfluorooctyl-sulfonyl)-piperazin-1-yl-carbonylmethyl]-1,4,7-tris(carboxymethyl)-1,4,7,10-tetraazacyclododecane 10 g (10.47 mmol) of the title compound of Example 27c) is dissolved in a mixture of 50 ml of water/20 ml of ethanol, and 1.90 g (5.23 mmol) of gadolinium oxide is added. It is stirred for 4 hours at 80° C. The solution is filtered and evaporated to dryness in a vacuum.

Yield: 12.2 g (quantitative)
Water content: 5.1%
Elementary analysis (relative to anhydrous substance):
Cld: C, 30.33; H, 2.91; F, 29.13; Gd, 14.18; S, 2.89. Fnd: C, 30.39; H, 2.81; F, 29.02; Gd, 14.01; S, 2.78.

EXAMPLE 28

Gadolinium complex, monosodium salt of 3,9-bis(carboxymethyl)-6-[(4-perfluorooctylsulfonyl)-piperazine-1-carbonylmethyl]-3,6,9-triazaundecanedioic acid a) 1-(2-Benzyloxycarbonylamino)-methyl-carboyl-4-(perfluorooctylsulfonyl)-piperazine 8.524 g (15 mmol) of the piperazine derivative that is produced under 27a) is dissolved in 80 ml of dichloromethane and mixed with 1.726 g (15 mmol) of N-hydroxysuccinimide, 3.095 g (15 mmol) of dicyclohexylcarbodiimide and 3.138 g (15 mmol) of N-benzyloxycarbonylglycine (commercially available products, Bachem). It is allowed to stir overnight, the dicyclohexylurea is filtered off, concentrated by evaporation, and the residue is subjected to column chromatography on silica gel. Mixtures of dichloromethane and ethanol are used as eluant. The title compound is obtained as a solid.

Yield: 10.16 g (89.2% of theory)
Elementary analysis:
Cld: C, 34.79; H, 2.39; F, 42.53; N, 5.53; S, 4.22. Fnd: C, 34.60; H, 2.43; F, 42.65; N, 5 b) 1-(2-Amino)-acetyl-4-(perfluorooctyl)-sulfonyl-piperazine 7.594 g (10 mmol) of the compound that is produced under 28a) is dissolved in 150 ml of a mixture of tetrahydrofuran and ethanol at a 2:1 ratio, and it is hydrogenated in the presence of 0.25 g of Pearlman's catalyst (Pd 20%/C) until 224 ml of hydrogen is taken up. Catalyst is suctioned out, rewashed well with ethanol and evaporated to dryness. The title compound is obtained as an amorphous solid.

Yield: 6.21 g (99.3% of theory)
Elementary analysis:
Cld: C, 26.89; H, 1.93; F, 51.65; N, 6.72; S, 5.13. Fnd: C, 27.03; H, 1.97; F, 51.77; N, 6.58; S, 5.20.

c) 3,9-Bis(t-butyloxycarbonylmethyl)-6-[(4-perfluorooctylsulfonyl)-piperazine-1-carbonylmethyl]-3,6,9-triazaundecanedicarboxylic acid-di(t-butylester)

3.127 g (5 mmol) of the amine that is produced under 28b) and 3.875 g (11 mmol) of N,N-bis(t-butyloxycarbonylmethyl)-2-(bromoethyl)-amine are added to a mixture of 10 ml of acetonitrile and 20 ml of phosphate buffer of pH 8.0, and it is stirred intensively at room temperature for 2 hours. Then, the buffer is separated, extracted with 10 ml of acetonitrile, and the latter is added to the organic phase. After 20 ml of fresh buffer is added, it is stirred for 20 more hours at room temperature. The organic phase is separated, concentrated by evaporation, and the residue is dispersed between 100 ml of phosphate buffer (pH 8.0) and 100 ml of ethyl acetate. The organic phase is washed with saturated common salt solution, dried on sodium sulfate and concentrated by evaporation. The title compound is purified by chromatography on silica gel. Dichloromethane with increasing addition of methanol is used as eluant. The title compound is obtained as a glass-like solid.

Yield: 4.481 g (76.3% of theory)
Elementary analysis:
Cld: C, 43.71; H, 5.42; F, 27.99; N, 4.85; S, 2.78. Fnd: C, 43.84; H, 5.47; F, 28.10; N, 5.00; S, 2.69.

d) 3,9-Bis(carboxymethyl)-6-[(4-perfluorooctylsulfonyl)-piperazin-1-yl-carbonylmethyl]-3,6,9-triazaundecanedioic acid 5.193 g (4.5 mmol) of the compound that is produced under 28c) is added to a mixture of 100 ml of trifluoroacetic acid/dichloromethane at a 2:1 ratio. It is allowed to stir overnight at room temperature, then evaporated to dryness, the remainder of the trifluoroacetic acid is removed by codistillation with ethanol and taken up in 160 ml of a mixture of water, ethanol and chloroform (10:5:1). A pH of about 3 (constant pH) is set by adding ion exchanger IRA-67 (OH⁻ form). It is quickly suctioned off, concentrated by evaporation, and the title compound is obtained as a vitreous solid.

Yield: 3.718 g (79.2% of theory)
Water content: 10.9%

Elementary analysis (relative to anhydrous substance):
Cld: C, 33.59; H, 3.25; F, 34.74; N, 6.03; S, 3.45. Fnd: C, 33.69; H, 3.36; F, 34.82; N, 6.10; S, 3.38.

e) Gadolinium complex, monosodium salt of 3,9-bis(carboxymethyl)-6-[(4-perfluorooctylsulfonyl)-piperazine-1-carbonylmethyl]-3,6,9-triazaundecanedioic acid 3.13 g (3.0 mmol, relative to 10.9% water content) of the acid that is produced under Example 28d) is added to a mixture of 60 ml of distilled water and 30 ml of ethanol. 543.8 mg (1.5 mmol) of gadolinium oxide is added in portions while being stirred and heated to 50° C. After addition is completed, it is stirred until dissolved. Then, the pH of the solution is adjusted to 7.2 by adding sodium hydroxide solution, and it is concentrated by evaporation. In this case, strong foaming occurs. The residue is codistilled twice with distilled water. The title compound is obtained as a vitreous solid.

Yield: 3.678 g (quantitative)
Water content: 9.2%
Elementary analysis (relative to anhydrous substance):
Cld: C, 28.24; H, 2.37; F, 29.21; Gd, 14.22; N, 5.07; Na, 2.08; S, 2.90. Fnd: C, 28.36; H, 2.41; F, 29.14; Gd, 14.30; N, 5.15; Na, 2.12; S, 2.83.

EXAMPLE 29

Gadolinium complex of 3,6,9-tris(carboxymethyl)-3,6,9-triazaundecanedioic acid-bis[(4-perfluorooctylsulfonyl)-piperazine]-amide a) 3,6,9-Tris(carboxymethyl)-3,6,9-triazaundecanedioic acid-bis[(4-perfluorooctylsulfonyl)-piperazine]-amide 5.683 g (10 mmol) of the compound that is produced under 27a) as well as 1.518 g (15 mmol) of triethylamine are dissolved in 30 ml of dry dimethylformamide and mixed in portions with 1.787 g (5 mmol) of diethylenetriaminepentaacetic acid-bisanhydride while being stirred and with exclusion of moisture. It is allowed to stir overnight, then concentrated by evaporation, mixed with water, the pH is adjusted to about 3 with 3N hydrochloric acid, and it is extracted twice with 100 ml of n-butanol each. The organic solutions are combined, concentrated by evaporation and subjected to a chromatography on silica gel RP-18. Water and tetrahydrofuran are used as eluant. The title compound is obtained as a glass-like solid.

Yield: 6.741 g (81.4% of theory)
Water content: 9.8%
Elementary analysis (relative to anhydrous substance):
Cld: C, 30.55; H, 2.50; F, 43.24; N, 6.56; S, 4.29. Fnd: C, 30.67; H, 2.55; F, 43.33; N, 6.49; S, 4.21.

b) Gadolinium complex of 3,6,9-tris(carboxymethyl)-3,6,9-triazaundecanedioic acid-bis[(4-perfluorooctylsulfonyl)-piperazine]-amide 6.570 g (4 mmol, relative to 9.8% water content) of the compound that is produced under 23c) is added to a mixture of 120 ml of distilled water, 60 ml of ethanol and 20 ml of chloroform. While being stirred and heated to 50° C., 725 mg (82.0 mmol) of gadolinium oxide is added in portions. It is stirred until dissolved, then concentrated by evaporation, whereby strong foaming occurs, and the residue is subjected to codistillation with distilled water. Codistillation is repeated twice. The title compound is obtained as a glass-like solid.

Yield: 7.191 g (quantitative)
Water content: 8.1%
Elementary analysis (relative to anhydrous substance):
Cld: C, 27.69; H, 2.08; F, 39.19; Gd, 9.54; N, 5.95; S, 3.89. Fnd: C, 27.83; H, 2.15; F, 39.10; Gd, 6.91; N, 6.03; S, 3.88.

EXAMPLE 30 a) 11-[N-Ethyl-N-(perfluorooctylsulfonyl)-amino]undecanoic acid benzyl ester 20 g (37.94 mmol) of N-ethyl-N-perfluorooctylsulfonamide and 15.73 g (113.8 mmol) of potassium carbonate are suspended in 200 ml of acetone, and 26.96 g (75.87 mmol) of 11-bromoundecanoic acid benzyl ester is added in drops at 60° C. It is stirred for 3 hours at 60° C. The salts are filtered out, and the filtrate is evaporated to dryness in a vacuum. The residue is chromatographed on silica gel (mobile solvent: hexane/dichloromethane/acetone=10/10/1). After the product-containing fractions are concentrated by evaporation, the residue is recrystallized from methanol/ether.

Yield: 26.46 g (87% of theory) of a colorless, crystalline powder
Elementary analysis:
Cld: C, 41.95; H, 4.02; N, 1.75; F, 40.29; S, 4.00. Fnd: C, 41.78; H, 4.17; N, 1.68; F, 40.12; S, 3.88.

b) 11-[N-Ethyl-N-(perfluorooctylsulfonyl)-aminoundecanoic acid 20 g (24.95 mmol) of the title compound of Example 30a) is dissolved in 300 ml of isopropanol/200 ml of dichloromethane, and 3 g of palladium catalyst (10% Pd/C) is added. It is hydrogenated overnight at room temperature. Catalyst is filtered out, and the filtrate is evaporated to dryness in a vacuum. The residue is recrystallized from ether/hexane.

Yield: 16.69 g (94% of theory) of a colorless, crystalline solid.
Elementary analysis:
Cld: C, 35.45; H, 3.68; N, 1.97; F, 45.39; S, 4.51. Fnd: C, 35.31; H, 3.81; N, 1.85; F, 45.25; S, 4.42.

c) Gadolinium complex of 10-[2-hydroxy-4-aza-5-oxo-16-aza-16-(perfluorooctylsulfonyl-octadecyl]-1,4,7-tris(carboxymethyl)-1,4,7,10-tetraazacyclododecane 12.16 g (17.09 mmol) of the title compound of Example 30b) and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C. and stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of gadolinium complex of 10-(3-amino-2-hydroxypropyl)-1,4,7-tris(carboxymethyl)-1,4,7,10-tetraazacyclododecane (WO 95/17451), dissolved in 50 ml of water, is added, and it is stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18/mobile solvent: gradient of water/N-propanol/acetonitrile).

Yield: 16.82 g (71% of theory) of a colorless, vitreous solid.

Water content: 8.6%

Elementary analysis (relative to anhydrous substance):

Cld: C, 36.02; H, 4.30; F, 25.49; Gd, 12.41; N, 6.63; S, 2.53. Fnd: C, 35.87; H, 4.45; F, 25.28; Gd, 12.29; N, 6.50; S, 2.41.

d) 10-[2-Hydroxy-4-aza-5-oxo-16-aza-16-(perfluorooctylsulfonyl-octadecyl]-1,4,7-tris(carboxymethyl)-1,4,7,10-tetraazacyclododecane 11.1 g (8.76 mmol) of the title compound of Example 30c) is dissolved in a mixture of 100 ml of water/100 ml of ethanol, and 1.73 g (13.71 mmol) of oxalic acid-dihydrate is added. It is heated for 8 hours to 80° C. It is cooled to 0° C., and precipitated gadolinium oxalate is filtered out. The filtrate is evaporated to dryness, and the residue is purified on RP-18 (RP-18/mobile solvent: gradient consisting of water/i-propanol/acetonitrile).

Yield: 9.80 g (92% of theory) of a vitreous solid.

Water content: 8.5%

Elementary analysis (relative to anhydrous substance):

Cld: C, 41.01; H, 5.16; F, 29.02; N, 7.55; S, 2.88. Fnd: C, 40.87; H, 5.31; F, 28.85; N, 7.40; S, 2.73.

e) Ytterbium complex of 10-[2-hydroxy-4-aza-5-oxo-16-aza-16-(perfluorooctylsulfonyl-octadecyl]-1,4,7-tris(carboxymethyl)-1,4,7,10-tetraazacyclododecane 1.33 g (2.53 mmol) of ytterbium carbonate is added to 5.64 g (5.07 mmol) of the title compound of Example 30d) in 100 ml of water/50 ml of ethanol, and it is stirred for 3 hours at 80° C. The solution is filtered, and the filtrate is evaporated to dryness in a vacuum.

Yield: 7.08 g (quantitative) of a vitreous solid.

Water content: 8.1%

Elementary analysis (relative to anhydrous substance):

Cld: C, 35.58; H, 4.24; F, 25.17; N, 6.55; S, 2.50; Yb, 13.49. Fnd: C, 35.43; H, 4.37; F, 25.05; N, 6.48; S, 2.39; Yb, 13.35.

f) Dysprosium complex of 10-[2-hydroxy-4-aza-5-oxo-16-aza-16-(perfluorooctylsulfonyl-octadecyl]-1,4,7-tris(carboxymethyl)-1,4,7,10-tetraazacyclododecane 0.95 g (2.53 mmol) of dysprosium oxide is added to 5.64 g (5.07 mmol) of the title compound of Example 30d) in 100 ml of water/50 ml of ethanol, and it is stirred for 3 hours at 80° C. The solution is filtered, and the filtrate is evaporated to dryness in a vacuum.

Yield: 7.10 g (quantitative) of a colorless, vitreous solid.

Water content: 9.1%

Elementary analysis (relative to anhydrous substance):

Cld: C, 35.87; H, 4.28; F, 25.38; N, 6.60; S, 2.52; Dy, 12.77. Fnd: C, 35.69; H, 4.39; F, 25.18; N, 6.49; S, 2.43; Dy, 12.70.

EXAMPLE 31 a) 11,11,11,10,10,9,9,8,8,7,7-Tridecafluoro-3-oxaundecanoic acid-tert-butyl ester 19.51 g (100.0 mmol) of bromoacetic acid-tert-butyl ester is added in drops to a mixture of 27.57 g (75.73 mmol) of 1H,1H,2H,2H-perfluorooctan-1-ol and 2.57 g (7.57 mmol) of tetrabutylammonium hydrogen sulfate in 300 ml of 60% aqueous potassium hydroxide solution/200 ml of toluene while being stirred vigorously at 0° C. It is stirred for one hour at 0° C., the organic phase is separated, and the aqueous phase is extracted twice with 50 ml of toluene. The combined organic extracts are dried on sodium sulfate and concentrated by evaporation in a vacuum. The residue is chromatographed on silica gel (mobile solvent: dichloromethane).

Yield: 28.97 g (80% of theory) of a colorless oil.

Elementary analysis:

Cld: C, 35.16; H, 3.16; F, 51.64. Fnd: C, 35.08; H, 3.20; F, 51.70.

b) 11,11,11,10,10,9,9,8,8,7,7-Tridecafluoro-3-oxaundecanoic acid 25.29 g (52.88 mmol) of the title compound of Example 1a) is dissolved in 300 ml of trifluoroacetic acid, and it is stirred overnight at room temperature. It is evaporated to dryness in a vacuum, and the residue is recrystallized from hexane/diethyl ether.

Yield: 20.54 g (92% of theory) of a colorless, crystalline solid.

Elementary analysis:

Cld: C, 28.45; H, 1.67; F, 58.51. Fnd: C, 28.36; H, 1.60; F, 58.62.

c) Gadolinium complex of 10-[2-hydroxy-4-aza-5-oxo-7-oxa-10,10,11,11,12,12,13,13,14,14,15,15,15-tridecafluoro-pentadecyl]-1,4,7-tris(carboxymethyl)-1,4,7,10-tetraazacyclododecane 7.21 g (17.09 mmol) of the title compound of Example 31b and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C., and it is stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of the gadolinium complex of 10-(3-amino-2-hydroxypropyl)-1,4,7-tris(carboxymethyl)-1,4,7,10-tetraazacyclododecane (WO 95/17451), dissolved in 50 ml of water, is added, and it is stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18/mobile solvent: gradient consisting of water/n-propanol/acetonitrile).

Yield: 12.68 g (71% of theory) of a colorless, vitreous solid.

Water content: 6.4%

Elementary analysis (relative to anhydrous substance):

Cld: C, 33.16; H, 3.61; F, 25.26; Gd, 16.08; N, 7.16. Fnd: C, 32.85; H, 3.84; F, 25.01; Gd, 15.87; N, 7.03.

EXAMPLE 32 a) 15,15,15,14,14,13,13,12,12,11,11,10,10,9,9,8,8-7, 7-Henicosafluoro-3-oxapenta-decanoic acid-tert-butyl ester 19.51 g (100.0 mmol) of bromoacetic acid-tert-butyl ester is added in drops to a mixture of 42.72 g (75.73 mmol) of 1H,1H,2H,2H-perfluorooctan-1-ol and 2.57 g (7.57 mmol) of tetrabutylammonium hydrogen sulfate in 300 ml of 60% aqueous potassium hydroxide solution/200 ml of toluene while being stirred vigorously at 0° C. It is stirred for one hour at 0° C., the organic phase is separated, and the aqueous phase is extracted twice with 50 ml of toluene. The combined organic extracts are dried on sodium sulfate and concentrated by evaporation in a vacuum. The residue is chromatographed on silica gel (mobile solvent: dichloromethane).

Yield: 42.12 g (82% of theory) of a colorless oil.
Elementary analysis:
Cld: C, 31.87; H, 2.23; F, 58.82. Fnd: C, 31.73; H, 2.20; F, 58.90.

b) 15,15,15,14,14,13,13,12,12,11,11,10,10,9,9,8,8,7, 7-Henicosafluoro-3-oxapentadecanoic acid-tert-butyl ester 35.87 g (52.88 mmol) of the title compound of Example 1a) is dissolved in 300 ml of trifluoroacetic acid, and it is stirred overnight at room temperature. It is evaporated to dryness in a vacuum, and the residue is recrystallized from hexane/diethyl ether.

Yield: 30.60 g (93% of theory) of a colorless, crystalline solid.
Elementary analysis:
Cld: C, 27.03; H, 1.13; F, 64.12. Fnd: C, 26.91; H, 1.20; F, 64.02.

c) Gadolinium complex of 10-[2-hydroxy-4-aza-5-oxo-7-oxa-10,10,11,11,12,12,13,13,14,14,15,15,16, 16,17,17,18,18,19,19,19-henicosafluoro-nonadecyl]-1,4,7-tris(carboxymethyl)-1,4,7-tris(carboxymethyl)-1,4,7,10-tetraazacyclododecane 10.63 g (17.09 mmol) of the title compound of Example 32b and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C., and it is stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of the gadolinium complex of 10-(3-amino-2-hydroxy-propyl)-1, 4,7-tris(carboxymethyl)-1,4,7,10-tetraazacyclododecane (WO 95/17451), dissolved in 50 ml of water, is added, and it is stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18/mobile solvent: gradient consisting of water/n-propanol/acetonitrile).

Yield: 14.73 g (69% of theory) of a colorless, vitreous solid.
Water content: 5.7%
Elementary analysis (relative to anhydrous substance):
Cld: C, 31.61; H, 2.99; F, 33.87; Gd, 13.35; N, 5.95. Fnd: C, 31.49; H, 3.15; F, 33.68; Gd, 13.21; N, 6.01.

EXAMPLE 33 a) N-(2-Bromopropionyl)glycine-benzyl ester 55.9 g (326.1 mmol) of 2-bromopropionic acid chloride is added in drops to 100 g (296.4 mmol) of glycine benzyl ester-p-toluenesulfonic acid salt and 33.0 g (326.1 mmol) of triethylamine in 400 ml of methylene chloride at 0° C. The temperature is not allowed to exceed 5° C. After the addition is completed, it is stirred for one hour at 0° C., then for 2 hours at room temperature. 500 ml of ice water is added, and the water phase is adjusted to pH 2 with 10% aqueous hydrochloric acid. The organic phase is separated and washed once each with 300 ml of 5% aqueous soda solution and 400 ml of water. The organic phase is dried on magnesium sulfate and evaporated to dryness in a vacuum. The residue is recrystallized from diisopropyl ether.

Yield: 68.51 g (75% of theory) of a colorless, crystalline powder
Melting point: 69-70° C.
Elementary analysis:
Cld: C, 48.02; H, 4.70; N, 4.67; Br, 26.62. Fnd: C, 47.91; H, 4.82; N, 4.51; Br, 26.47.

b) 1-(4-(Benzyloxycarbonyl)-1-methyl-2-oxo-3-azabutyl]-1,4,7,10-tetraazacyclododecane 50 g (162.2 mmol) of the title compound of Example 1a) is added to 55.8 g (324.4 mmol) of 1,4,7,10-tetraazacyclododecane, dissolved in 600 ml of chloroform, and it is stirred overnight at room temperature. 500 ml of water is added, the organic phase is separated, and it is washed twice with 400 ml of water in each case. The organic phase is dried on magnesium sulfate and evaporated to dryness in a vacuum. The residue is chromatographed on silica gel (mobile solvent: chloroform/methanol/aqueous 25% ammonia=10/5/1).

Yield: 40.0 g (63% of theory relative to 1a) used] of a light yellowish viscous oil.
Elementary analysis:
Cld: C, 61.36; H, 8.50; N, 17.39. Fnd: C, 61.54; H, 8.68; N, 17.68.

c) 10-[4-(Benzyloxycarbonyl)-1-methyl-2-oxo-3-azabutyl]-1,4,7-tris(tert-butoxy-carbonylmethyl)-1,4, 7,10-tetraazacyclododecane (sodium bromide complex)

33 g (169 mmol) of bromoacetic acid-tert-butyl ester is added to 20 g (51.08 mmol) of the title compound of Example 1b) and 17.91 g (169 mmol) of sodium carbonate in 300 ml of acetonitrile, and it is stirred for 24 hours at 60° C. It is cooled to 0° C., salts are filtered out, and the filtrate is evaporated to dryness. The residue is chromatographed on silica gel (mobile solvent: ethyl acetate/ethanol: 15/1). The fractions that contain the product are concentrated by evaporation, and the residue is recrystallized from diisopropyl ether.

Yield: 34.62 g (81% of theory) of a colorless, crystalline powder
Melting point: 116-117° C.
Elementary analysis:
Cld: C, 54.54; H, 7.59; N, 8.37; Na, 2.74; Br, 9.56. Fnd: C, 54.70; H, 7.65; N, 8.24; Na, 2.60; Br, 9.37.

d) 10-(4-Carboxy-1-methyl-2-oxo-3-azabutyl)-1,4,7-tris(tert-butoxycarbonylmethyl)-1,4,7,10-tetraazacyclododecane (sodium bromide complex)

30 g (35.85 mmol) of the title compound of Example 1c is dissolved in 500 ml of isopropanol, and 3 g of palladium catalyst (10% Pd/C) is added. It is hydrogenated overnight at room temperature. Catalyst is filtered out, the filtrate is evaporated to dryness in a vacuum and recrystallized from acetone.

Yield: 22.75 g (85% of theory) of a colorless, crystalline powder

Melting point: 225° C. (decomposition)

Elementary analysis:
Cld: C, 49.86; H, 7.69; N, 9.38; Na, 3.07; Br, 10.71. Fnd: C, 49.75; H, 7.81; N, 9.25; Na, 2.94; Br, 10.58.

e) 10-[1-Methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane 10 g (13.39 mmol) of the title compound of Example 33d and 7.61 g (13.39 mmol) of the title compound of Example 27a are dissolved in 150 ml of tetrahydrofuran. 3.97 g (16.07 mmol) of N-ethoxycarbonyl-2-ethoxy-1,2-dihydroquinoline (EEDQ) is added at 0° C., stirred for 3 hours at 0° C., then for 12 hours at room temperature. It is evaporated to dryness in a vacuum. The residue is taken up in 150 ml of trifluoroacetic acid and stirred for 12 hours at room temperature. It is evaporated to dryness, the residue is dissolved in water and adjusted to pH 3.2 with 10% aqueous sodium hydroxide solution. For purification, it is chromatographed on RP-18 (gradient consisting of water/acetonitrile/tetrahydrofuran).

Yield: 9.67 g (63% of theory) of a hygroscopic solid.

Water content: 10.5%

Elementary analysis (relative to anhydrous substance):
Cld: C, 36.30; H, 3.93; N, 9.56; F, 31.49; S, 3.13. Fnd: C, 36.14; H, 3.98; N, 9.40; F, 31.67; S, 3.02.

f) Gadolinium complex of 10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane 5 g (4.87 mmol) of the title compound of Example 33e is dissolved in 60 ml of water, and 0.883 g (2.44 mmol) of gadolinium oxide is added. It is stirred for 3 hours at 90° C. The solution is filtered, and the filtrate is freeze-dried.

Yield: 6.47 g (quantitative) of a voluminous, amorphous powder

Water content: 11.3%

Elementary analysis (relative to anhydrous substance):
Cld: C, 31.56; H, 3.16; N, 8.31; F, 27.37; S, 2.72; Gd, 13.33. Fnd: C, 31.37; H, 3.35; N, 8.18; F, 27.19; S, 2.92; Gd, 13.05.

EXAMPLE 34 a) 4-Perfluorooctanesulfonylpiperazin-1-ylpentanediamic acid

A solution of 10.62 g (105.0 mmol) of triethylamine and 59.67 g (105.0 mmol) of the title compound of Example 27a) in 50 ml of tetrahydrofuran are added in drops to a suspension of 11.41 g (100.0 mmol) of glutaric anhydride in 100 ml of tetrahydrofuran while being stirred vigorously at 0° C., and it is allowed to come to room temperature overnight.

The reaction mixture is acidified with 100 ml of 2N HCl and extracted three times with 100 ml of tetrahydrofuran. The combined organic extracts are dried with sodium sulfate, filtered and concentrated by evaporation. The residue is recrystallized from 2-propanol/ethyl acetate.

Yield: 52.30 g (73% of theory) of a colorless, crystalline solid.

Elementary analysis:
Cld: C, 29.92; H, 2.22; N, 4.11; F, 47.33; S, 4.70. Fnd: C, 29.90; H, 2.18; N, 4.07; F, 47.42; S, 4.79.

b) Gadolinium complex of 10-[2-hydroxy-4-aza-5,9-dioxo-9-{4-perfluorooctyl)-piperazin-1-yl}-nonyl]-1,4,7-tris(carboxymethyl)-1,4,7-tris(carboxymethyl)-1,4,7,10-tetraazacyclododecane 11.66 g (17.09 mmol) of the title compound of Example 34a and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C., and it is stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of the gadolinium complex of 10-(3-amino-2-hydroxypropyl)-1,4,7-tris(carboxymethyl)-1,4,7,10-tetraazacyclododecane (WO 95/17451), dissolved in 50 ml of water, is added, and it is stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18/mobile solvent: gradient consisting of water/n-propanol/acetonitrile).

Yield: 16.7 g (73% of theory) of a colorless, vitreous solid.

Water content: 7.5%

Elementary analysis (relative to anhydrous substance):
Cld: C, 32.99; H, 3.50; F, 26.09; Gd, 12.70; N, 7.92; S, 2.59. Fnd: C, 32.75; H, 3.68; F, 25.88; Gd, 12.55; N, 7.84; S, 2.63.

EXAMPLE 35 a) N-Benzylperfluorooctanesulfonamide 50.21 g (100.0 mmol) of perfluorooctanesulfonyl fluoride is added in drops to a mixture of 10.62 g (105.0 mmol) of triethylamine and 10.72 g (100.0 mmol) of benzylamine at 80° C. while being stirred vigorously. It is stirred for 2 days at 80° C., the reaction mixture is mixed with 300 ml of water and extracted 3 times with ethyl acetate. The combined organic extracts are dried on sodium sulfate, filtered and concentrated by evaporation. The residue is chromatographed on silica gel (mobile solvent: dichloromethane/methanol=4/1).

Yield: 45.96 g (78% of theory) of a colorless liquid

Elementary analysis:
Cld: C, 30.57; H, 1.37; N, 2.38; S, 5.44; F, 54.81. Fnd: C, 30.49; H, 1.30; N, 2.42; S, 5.50; F, 54.90.

b) N-Benzyl-N-(perfluorooctylsulfonyl)-aminoacetic acid-t-butyl ester 22.4 g (37.94 mmol) of the title compound of Example 35a and 15.73 g (113.8 mmol) of potassium carbonate are suspended in 200 ml of acetone, and 14.80 g (75.87 mmol) of bromoacetic acid-tert-butyl ester is added in drops at 60°

C. It is stirred for 3 hours at 60° C. Salts are filtered out, and the filtrate is evaporated to dryness in a vacuum. The residue is chromatographed on silica gel (mobile solvent: hexane/dichloromethane/acetone=10/10/1). After the product-containing fractions are concentrated by evaporation, the residue is recrystallized from methanol/ether.

Yield: 24.02 g (90% of theory) of a waxy, colorless solid

Elementary analysis:

Cld: C, 35.86; H, 2.58; N, 1.99; S, 4.56; F, 45.91. Fnd: C, 35.67; H, 2.71; N, 2.13; S, 4.45; F, 45.83.

c) N-Benzyl-N-(perfluorooctylsulfonyl)-aminoacetic acid 20 g (28.43 mmol) of the title compound of Example 35b is dissolved in 200 ml of trifluoroacetic acid, and it is stirred overnight at room temperature. It is evaporated to dryness in a vacuum. The residue is recrystallized from methanol/ether.

Yield: 17.48 g (95% of theory) of a colorless, crystalline solid

Elementary analysis:

Cld: C, 31.54; H, 1.56; N, 2.16; S, 4.95; F, 49.89. Fnd: C, 31.38; H, 1.70; N, 2.05; S, 4.87; F, 49.71.

d) Gadolinium Complex of 10-[2-hydroxy-4-aza-5-oxo-7-aza-7-(perfluorooctylsulfonyl)-8-phenyl-octyl]-1,4,7-tris(carboxymethyl)-1,4,7,10-tetraazacyclododecane 11.06 g (17.09 mmol) of the title compound of Example 35c and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C., and it is stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of the gadolinium complex of 10-(3-amino-2-hydroxy-propyl)-1,4,7-tris(carboxymethyl)-1,4,7,10-tetraazacyclododecane (WO 95/17451), dissolved in 50 ml of water, is added and stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18-mobile solvent: gradient consisting of water/n-propanol/acetonitrile).

Yield: 16.49 g (75% of theory) of a colorless, vitreous solid

Water content: 6.5%

Elementary analysis:

Cld: C, 33.95; H, 3.18; N, 6.99; S, 2.67; F, 26.85; Gd, 13.07. Fnd: C, 33.81; H, 3.24; N, 6.82; S, 2.54; F, 26.64; Gd, 12.91.

EXAMPLE 36 a) N-Decylperfluorooctanesulfonamide 50.21 g (100.0 mmol) of perfluorooctanesulfonyl fluoride is added in drops to a mixture of 10.62 g (105.0 mmol) of triethylamine and 15.73 g (100.0 mmol) of decylamine at 80° C. while being stirred vigorously. It is stirred for 2 days at 80° C., the reaction mixture is mixed with 300 ml of water and extracted three times with ethyl acetate. The combined organic extracts are dried on sodium sulfate, filtered and concentrated by evaporation. The residue is chromatographed on silica gel (mobile solvent: dichloromethane/methanol=4/1).

Yield: 43.48 g (68% of theory) of a colorless, viscous liquid

Elementary analysis:

Cld: C, 33.81; H, 3.47; N, 2.19; S, 5.02; F, 50.51. Fnd: C, 33.71; H, 3.39; N, 2.15; S, 4.93; F, 50.31.

b) N-Decyl-N-(perfluorooctylsulfonyl)-aminoacetic acid-t-butyl ester 24.26 g (37.94 mmol) of the title compound of Example 36a and 15.73 g (113.8 mmol) of potassium carbonate are suspended in 200 ml of acetone, and 14.80 g (75.87 mmol) of bromoacetic acid-tert-butyl ester is added in drops at 60° C. It is stirred for 3 hours at 60° C. Salts are filtered out, and the filtrate is evaporated to dryness in a vacuum. The residue is chromatographed on silica gel (mobile solvent: hexane/dichloromethane/acetone=10/10/1). After the product-containing fractions are concentrated by evaporation, the residue is recrystallized from methanol/ether.

Yield: 24.87 g (87% of theory) of a waxy, colorless solid

Elementary analysis:

Cld: C, 38.25; H, 4.28; N, 1.86; S, 4.26; F, 42.86. Fnd: C, 38.09; H, 4.41; N, 1.74; S, 4.10; F, 42.67.

c) N-Decyl-N-(perfluorooctylsulfonyl)-aminoacetic acid 20 g (26.54 mmol) of the title compound of Example 36b is dissolved in 200 ml of trifluoroacetic acid and stirred overnight at room temperature. It is evaporated to dryness in a vacuum. The residue is recrystallized from methanol/ether.

Yield: 17.22 g (93% of theory) of a colorless, crystalline solid

Elementary analysis:

Cld: C, 34.44; H, 3.47; N, 2.01; S, 4.60; F, 46.31. Fnd: C, 34.28; H, 3.30; N, 1.95; S, 4.65; F, 46.28.

d) Gadolinium complex of 10-[2-hydroxy-4-aza-5-oxo-7-aza-7-(perfluorooctylsulfonyl)-heptadecyl]-1,4,7-tris(carboxymethyl)-1,4,7,10-tetraazacyclododecane 11.92 g (17.09 mmol) of the title compound of Example 36c and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C., and it is stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of the gadolinium complex of 10-(3-amino-2-hydroxy-propyl)-1,4,7-tris(carboxymethyl)-1,4,7,10-tetraazacyclododecane (WO 95/17451), dissolved in 50 ml of water, is added, and it is stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18 mobile solvent: gradient consisting of water/n-propanol/acetonitrile).

Yield: 16.76 g (71% of theory) of a colorless, vitreous solid

Water content: 6.5%

Elementary analysis:

Cld: C, 35.46; H, 4.18; N, 6.71; S, 2.56; F, 25.77; Gd, 12.55. Fnd: C, 35.28; H, 4.33; N, 6.80; S, 2.61; F, 25.65; Gd, 12.41.

EXAMPLE 37 a) N-Hexylperfluorooctanesulfonamide 50.21 g (100.0 mmol) of perfluoroctanesulfonyl fluoride is added in drops to a mixture of 10.62 g (105.0 mmol) of triethylamine and 10.12 g (100.0 mmol) of benzylamine at 80° C. while being stirred vigorously. It is stirred for 2 days at 80° C., the reaction mixture is mixed with 300 ml of water and extracted three times with ethyl acetate. The combined organic extracts are dried on sodium sulfate, filtered and concentrated by evaporation. The residue is chromatographed on silica gel (mobile solvent: dichloromethane/methanol=4/1).

Yield: 45.50 g (78% of theory) of a colorless liquid
Elementary analysis:
Cld: C, 28.83; H, 2.42; N, 2.40; S, 5.50; F, 55.37. Fnd: C, 28.29; H, 2.39; N, 2.44; S, 5.55; F, 55.50.

b) N-Hexyl-N-(perfluorooctylsulfonyl)-aminoacetic acid-t-butyl ester 22.13 g (37.94 mmol) of the title compound of Example 37a and 15.73 g (113.8 mmol) of potassium carbonate are suspended in 200 ml of acetone, and 14.80 g (75.87 mmol) of bromoacetic acid-tert-butyl ester is added in drops at 60° C. It is stirred for 3 hours at 60° C. Salts are filtered out, and the filtrate is evaporated to dryness in a vacuum. The residue is chromatographed on silica gel (mobile solvent: hexane/dichloromethane/acetone=10/10/1). After the product-containing fractions are concentrated by evaporation, the residue is recrystallized from methanol/ether.

Yield: 23.02 g (87% of theory) of a waxy, colorless solid
Elementary analysis:
Cld: C, 34.44; H, 3.47; N, 2.01; S, 4.60; F, 46.31. Fnd: C, 34.31; H, 3.61; N, 1.97; S, 4.65; F, 46.25.

c) N-Hexyl-N-(perfluorooctylsulfonyl)-aminoacetic acid 20 g (28.43 mmol) of the title compound of Example 37b is dissolved in 200 ml of trifluoroacetic acid, and it is stirred overnight at room temperature. It is evaporated to dryness in a vacuum. The residue is recrystallized from methanol/ether.

Yield: 16.74 g (91% of theory) of a colorless, crystalline solid
Elementary analysis:
Cld: C, 29.96; H, 2.51; N, 2.18; S, 5.00; F, 50.36. Fnd: C, 29.87; H, 2.70; N, 2.05; S, 4.84; F, 50.17.

d) Gadolinium Complex of 10-[2-hydroxy-4-aza-5-oxo-7-aza-7-(perfluorooctylsulfonyl)-tridecyl]-1,4,7-tris(carboxymethyl)-1,4,7,10-tetraazacyclododecane 10.96 g (17.09 mmol) of the title compound of Example 37c and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C., and it is stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of the gadolinium complex of 10-(3-amino-2-hydroxy-propyl)-1,4,7-tris(carboxymethyl)-1,4,7,10-tetraazacyclododecane (WO 95/17451), dissolved in 50 ml of water, is added, and it is stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18 mobile solvent: gradient consisting of water/n-propanol/acetonitrile).

Yield: 16.46 g (75% of theory) of a colorless, vitreous solid
Water content: 6.8%
Elementary analysis:
Cld: C, 33.11; H, 3.70; N, 7.02; S, 2.68; F, 26.98; Gd, 13.14. Fnd: C, 33.01; H, 3.84; N, 6.95; S, 2.57; F, 26.85; Gd, 13.03.

EXAMPLE 38 a) 11-[N-Ethyl-N-(perfluorooctylsulfonyl)-amino]-hexanoic acid benzyl ester 20 g (37.94 mmol) of N-ethyl-N-perfluorooctylsulfonylamide and 15.73 g (113.8 mmol) of potassium carbonate are suspended in 200 ml of acetone, and 21.64 g (75.87 mmol) of 6-bromohexanoic acid benzyl ester is added in drops at 60° C. It is stirred for 3 hours at 60° C. Salts are filtered out, and the filtrate is evaporated to dryness in a vacuum. The residue is chromatographed on silica gel (mobile solvent: hexane/dichloromethane/acetone 10/10/1). After the product-containing fractions are concentrated by evaporation, the residue is recrystallized from methanol/ether.

Yield: 25.26 g (91% of theory) of a colorless, crystalline powder
Elementary analysis:
Cld: C, 37.77; H, 3.03; N, 1.91; S, 4.38; F, 44.15. Fnd: C, 37.61; H, 3.18; N, 1.84; S, 4.27; F, 44.01.

b) 11-[N-Ethyl-N-(perfluorooctylsulfonyl)-amino]-hexanoic acid 20 g (27.34 mmol) of the title compound of Example 38b is dissolved in 300 ml of isopropanol/200 ml of dichloromethane, and 3 g of palladium catalyst (10% Pd/C) is added. It is hydrogenated overnight at room temperature. Catalyst is filtered out, and the filtrate is evaporated to dryness in a vacuum. The residue is recrystallized from ether/hexane.

Yield: 16.13 g (92% of theory) of a colorless, crystalline solid
Elementary analysis:
Cld: C, 29.96; H, 2.51; N, 2.18; S, 5.00; F, 50.36. Fnd: C, 29.81; H, 2.70; N, 2.09; S, 4.93; F, 50.14.

d) Gadolinium Complex of 10-[2-hydroxy-4-aza-5-oxo-11-aza-11-(perfluorooctylsulfonyl)-tridecyl]-1,4,7-tris(carboxymethyl)-1,4,7,10-tetraazacyclododecane 10.96 g (17.09 mmol) of the title compound of Example 38b and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C., and it is stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of the gadolinium complex of 10-(3-amino-2-hydroxy-propyl)-1,4,7-tris(carboxymethyl)-1,4,7,10-tetraazacyclododecane (WO 95/17451), dissolved in 50 ml of water, is added, and it is stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18 mobile solvent: gradient consisting of water/n-propanol/acetonitrile).

Yield: 15.0 g (69% of theory) of a colorless, vitreous solid
Water content: 5.9%
Elementary analysis:
Cld: C, 33.11; H, 3.70; N, 7.02; S, 2.68; F, 26.98; Gd, 13.14. Fnd: C, 33.01; H, 3.83; N, 6.91; S, 2.49; F, 26.83; Gd, 13.05.

EXAMPLE 39

Blood Elimination Kinetics of Contrast Media

The blood elimination kinetics of contrast media was examined in rats (Han Wistar, Schering SPF, ≈250 g of body weight). For this purpose, after one-time intravenous administration (via a caudal vein) of the substances (dose: 50-100 μmol of Me per kg of body weight), the substance concentration in the blood (based on the Gd or Dy content) was determined over a period of up to 300 minutes p.i. with the aid of ICP-AES. The pharmacokinetic parameters: distribution volume (Vss), total clearance (CLtot) and elimination half-life (tβ) were calculated with a special computer program (TOPFIT 2.0; Thomae, Schering, Gödecke), whereby a one- or two-compartment distribution model was used as a basis.

In comparison to Dy-DTPA (the dysprosium analogue of Magnevist®), the fluorine compounds according to the invention (e.g., Example 1c) showed considerably slower elimination from the blood and, in addition, a smaller distribution volume (see also FIG. 1 and Table 1).

It has been determined, surprisingly enough, that these compounds have an extended retention in the blood space and therefore are suitable as "blood pool contrast media"—e.g., for the visualization of blood vessels with suitable techniques—even at relatively small dosages of ≦50 μmol of Gd per kg of body weight.

FIG. 1:

Elimination from the blood (in % of the injected dose) of Dy-DTPA (dose: 100 μmol of Dy per kg of body weight, n=3) and of the fluorine compounds of Example 1c according to the invention (dose: 50 μmol of Gd per kg of body weight, n=2) after one-time intravenous administration of substances in rats (Han Wistar, Schering SPF, ≈250 g of body weight).

The Gd and Dy contents in the blood were determined with the aid of ICP-AES.

[Key to Table:]
% der injizierten dosis=% of injected dose
Beispiel 1c=Example 1c

TABLE 1

Pharmacokinetic parameters: distribution volume (Vss), total clearance (CLtot) and elimination half-life (tβ) of Dy-DTPA and the fluorine compounds of Example 1c according to the invention (calculated with TOPFIT 2.0; one- or two-compartment model).

|  | Vss (l/kg) | | CLtot(ml/(min · kg)) | | tβ (min) | |
| --- | --- | --- | --- | --- | --- | --- |
|  | MEAN | SD | MEAN | SD | MEAN | SD |
| Dy-DTPA | 0.17 | 0.00 | 9.27 | 0.60 | 14.98 | 0.73 |
| Example 1c | 0.14 | 0.02 | 1.07 | 0.09 | 95.01 | 10.37 |

For further details see text for FIG. 1

EXAMPLE 40

Lymph Node Concentration in Guinea Pigs

Various fluorine-containing gadolinium and manganese complexes were examined 90 minutes to 24 hours after subcutaneous administration (2.5-10 μmol of total gadolinium/kg of body weight, hind paw s.c.)-to stimulated guinea pigs (complete Freund's adjunct; 0.1 ml i.m. respectively in the right and left thigh and lower leg: 2 weeks before administration of test substances) to determine their lymph node concentration in three successive lymph node stations (popliteal, inguinal, iliac). In this case, the results (determination of gadolinium concentration with the aid of ICP-AES) that are listed below in Table 2 were obtained:

TABLE 2

| Substance Example No. | Time of lymph node removal (dose) | Gadolinium or manganese concentration in three successive lymph node stations [μmol/l] [% dose/g of tissue] | | | |
| --- | --- | --- | --- | --- | --- |
|  |  | popliteal | inguinal | iliac | ratio |
| 1c) | 4 h (2.5 μmol/kg) | 120 μmol/l 17.2% | 29 μmol/l 4.2% | 40 μmol/l 5.6% | 10:2.4:3.3 |
| 2c) | 4 h (10 μmol/kg) | 435 μmol/l 10.5% | 84 μmol/l 2.0% | 150 μmol/l 3.6% | 10:2.0:3.5 |
| 1e) | 90 min (10 μmol/kg) | 559 μmol/l 15% | 224 μmol/l 6.0% | 290 μmol/l 7.8% | 10:4.0:5.2 |
| 3c) | 90 min (10 μmol/kg) | 880 μmol/l 21.4% | 277 μmol/l 6.7% | 339 μmol/l 8.3% | 10:3.1:3.9 |

EXAMPLE 41

Figure 1:
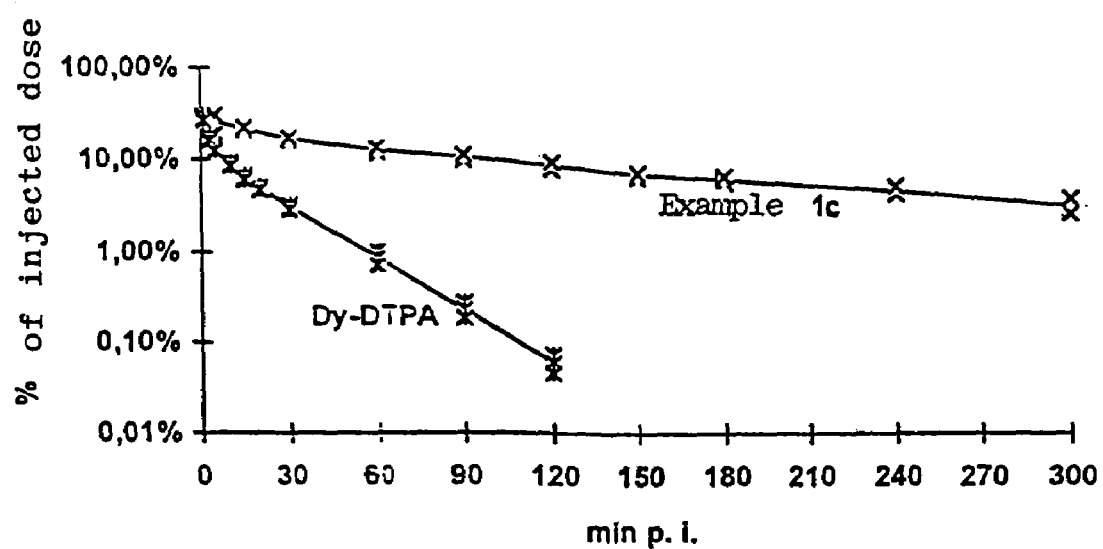
FIG. 1. before and after contrast MR recordings of lymph nodes with a compound of the invention.
Figure 2:
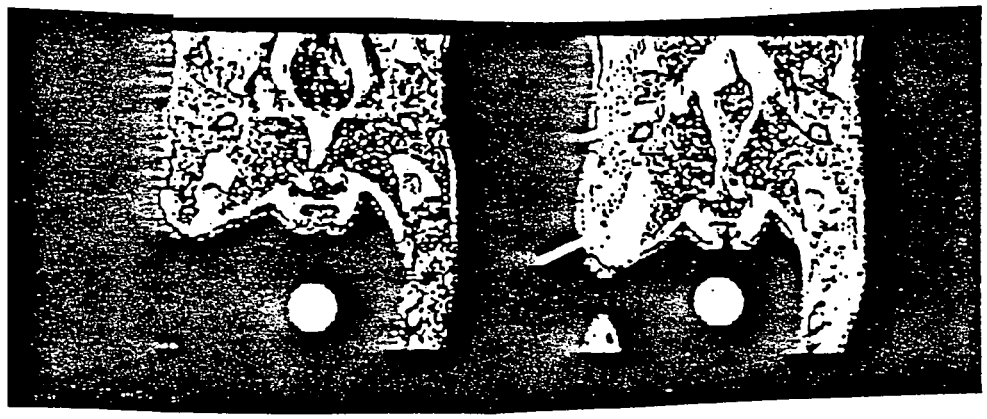
FIG. 2. shows before and after contrast MR images.

Lymph Node Visualization (MRT) after Interstitial Administration of the Contrast Medium FIG. 1 shows MR recordings of popliteal and inguinal lymph nodes both before (left side: precontrast) and 120 minutes after (right side) subcutaneous administration (guinea pigs, hind paw, interdigital space) of the Gd complex of Example 2c (referred to in the figure as Gd-D03A-γ-aminoamide-perfluorooctylether) (10 μmol of Gd/kg of body weight). The $T^1$-weighted spin echo recordings (TR 400 ms, TE 15 ms) illustrate the strong signal rise in the popliteal and inguinal lymph nodes of the injected side of the body (straight arrow) in comparison to the non-injected side of the body (curved arrow), or to the precontrast image.

EXAMPLE 42

Elimination of the Contrast Medium after i.p. Administration

After administration of a perfluorinated gadolinium complex according to the invention (100 μmol of total gadolinium/kg of body weight) in the intraperitoneal space of rats, the retention of metal in the liver as well as in the remainder of the body was examined 14 days after administration. In this test, fluorine-containing compound 2c) was used. After 14 days p.i., the gadolinium concentration was 0.22% of the administered dose in the liver and 1.1% of the administered dose in the remainder of the body.

In comparison with this, Gd-DPTA-polylysine as polymeric material is not completely eliminated. After 14 days, the body still contains 7% of the original dose.

EXAMPLE 43

Determination of $T^1$-Relaxivity of Selected Compounds

The relaxivity of the following compounds was determined with a Minispec pc 20 (20 MHz, 0.47 T) at 37° C. in water and human plasma and compared to that of Gd-DTPA-polylysine and Magnevist® as comparison substances.

TABLE 3

| Substance Example No. | $R^1$ [L/mmol*sec] at 0.47 T and 37° C. | |
|---|---|---|
| | Water | Plasma |
| 1c) | 41 | 49 |
| 2c) | 19 | 33 |
| 3c) | 15.2 | 27.5 |
| 22f) | 6.9 | 20.5 |
| 30c) | 21.1 | 26.9 |
| 31c) | 5.2 | 29.1 |
| 32c) | 19.4 | 24.8 |
| 33f) | 31.5 | 35.7 |
| 34b) | 25.9 | 24.9 |
| 35d) | 23.1 | 34.0 |
| 37d) | 19.9 | n.m. |
| 38c) | 23.3 | 30.5 |
| Comparison substances: | | |
| Magnevist(R) | 3.8 | 4.8 |
| Gd-DTPA-polylysine[1] | 13.1 | 16.8 |

[1]from Invest. Radiol. 1992, 346
n.m. = not measured

The invention claimed is:

1. A method of imaging lymph nodes, comprising conducting said imaging in conjunction with administration of a contrast agent comprising a perfluoroalkyl-containing compound of formula I $$R^F—L—A \qquad I$$

in which
$R^F$ is a perfluorinated, straight-chain or branched carbon chain with formula $—C_nF_{2n}X$, in which
X represents a terminal fluorine, chlorine, bromine, iodine or hydrogen atom, and n is 6-10,
L means a direct bond, a methylene group, an —NHCO group, or a group $$—\!\!\left[\!(CH_2)_u—NHCOCH_2—(CH_2)_p\!\right]_q\!\!—\overset{R^1}{\underset{|}{N}}—SO_2—,$$

whereby p means numbers 0 to 10, q and u, independently of one another, mean numbers 0 or 1 and
$R^1$ is a hydrogen atom, a methyl group, a —CH₂—OH group, a —CH₂—CO₂H group or a $C_2$-$C_{15}$ chain, which optionally is interrupted by 1 to 3 oxygen atoms, 1 to 2 CO groups or an optionally substituted aryl group and/or is substituted with 1 to 4 hydroxyl groups, 1 to 2 $C_1$-$C_4$ alkoxy groups, 1 to 2 carboxy groups, a group —SO₃H, or L is a straight-chain, branched, saturated or unsaturated $C_2$-$C_{30}$ carbon chain, which optionally contains 1 to 10 oxygen atoms, 1 to 3 —NR¹ groups, 1 to 2 sulfur atoms, a piperazine, a —CONR¹ group, an —SO₂ group, an —NR¹—CO₂ group, 1 to 2 —CO groups, a group —CO—N—T—N(R¹)—SO₂—$R^F$ or 1 to 2 optionally substituted aryls and/or is interrupted by these groups and/or is optionally substituted with 1 to 3 —OR¹ groups, 1 to 2 oxo groups, 1 to 2 —NH—COR¹ groups, 1 to 2 —CONHR¹ groups, 1 to 2 —(CH₂)$_p$—CO₂H groups, 1 to 2 groups of —(CH₂)$_p$—(O)$_q$—CH₂CH₂—$R^F$, whereby
$R^1$, $R^F$ and p and q have the above-indicated meanings, and
T means a $C_2$-$C_{10}$ chain, which optionally is interrupted by 1 to 2 oxygen atoms or 1 to 2 —NHCO groups,
A stands for a complexing agent, a metal complex, or a salt of said complexing agent or metal complex with an organic and/or inorganic base or amino acid or amino acid amide, said complexing agent or complex having formula II in which $R^3$, $Z^1$ and Y are independent of one another, and
$R^3$ has the meaning of $R^1$ or means —(CH₂)$_m$—L—$R^F$, whereby m is 0, 1 or 2 and L and $R^F$ have the above-mentioned meaning,
$Z^1$ independently of one another, mean a hydrogen atom or a metal ion equivalent of atomic numbers 21-29, 39, 42, 44 or 57-83,
Y means —OZ¹ or whereby $Z^1$, L, $R^F$ and $R^3$ have the above-mentioned meanings, or
said complexing agent or complex having formula III in which $R^3$ and $Z^1$ have the above-mentioned meanings and $R^2$ has the meaning of $R^1$, or
   said complexing agent or complex having formula IV

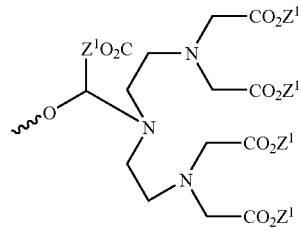

(IV)

in which $Z^1$ has the above-mentioned meaning,
or
   said complexing agent or complex having formula V

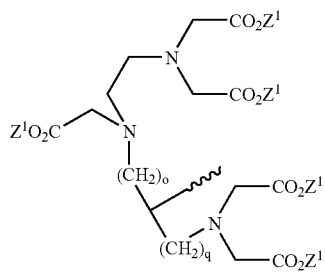

(V)

in which $Z^1$ has the above-mentioned meaning, and o and q stand for numbers 0 or 1 and the sum o+q=1 results,
or
   said complexing agent or complex having formula VI

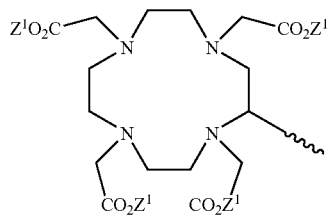

(VI)

in which $Z^1$ has the above-mentioned meaning
or
   said complexing agent or complex having formula VII

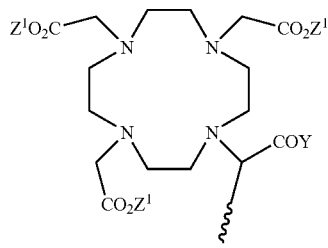

(VII)

in which $Z^1$ and Y have the above-mentioned meanings or
   said complexing agent or complex having formula VIII

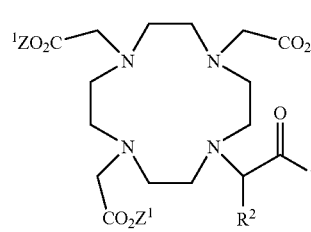

(VIII)

in which $R^3$ and $Z^1$ have the above-mentioned meanings, and $R^2$ has the above-mentioned meaning of $R^1$,
or
   said complexing agent or complex having formula IX

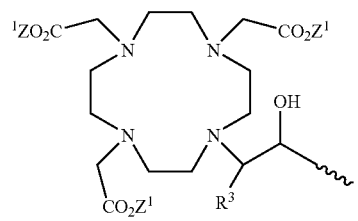

(IX)

in which $R^3$ and $Z^1$ have the above-mentioned meanings,
or
   said complexing agent or complex having formula X

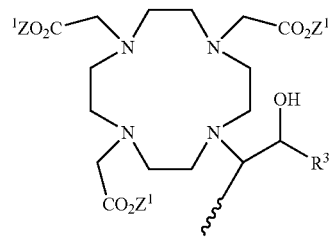

(X)

in which $R^3$ and $Z^1$ have the above-mentioned meanings,
or
   said complexing agent or complex having formula XI

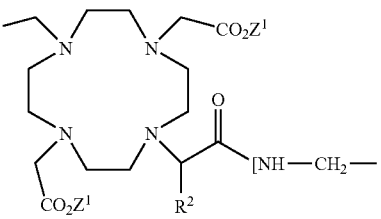

-continued

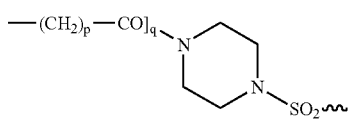

in which $Z^1$, p and q have the above-mentioned meaning and $R^2$ has the meaning of $R^1$, or said complexing agent or complex having formula XII

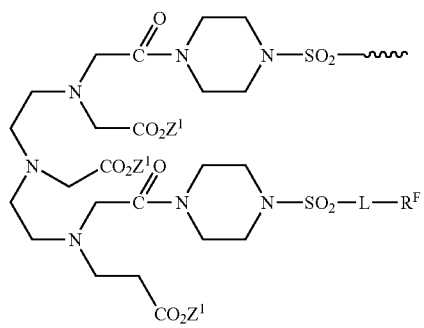

(XII)

in which L, $R^F$ and $Z^1$ have the above-mentioned meanings, or said complexing agent or complex having formula XIII

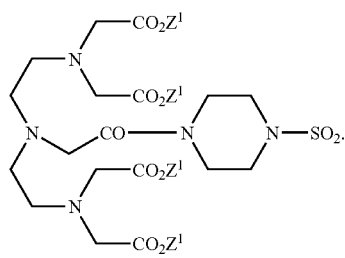

(XIII)

2. A method according to claim 1, wherein $Z^1$ stands for a hydrogen atom.

3. A method according to claim 1, wherein X in formula —$C_nF_{2n}X$ means a fluorine atom.

4. A method according to claim 1, wherein L stands for —$CH_2$—, —$CH_2CH_2$—, —$(CH_2)_s$—, —$CH_2$—O—$CH_2CH_2$—, —$CH_2$—(O—$CH_2$—$CH_2$—)$_t$, —$CH_2$—NH—CO—,
—$CH_2$NH—CO—$CH_2$—N($CH_2$COOH)—$SO_2$—,
—$CH_2$—NH—CO—$CH_2$—N($C_2H_5$)$SO_2$—,
—$CH_2$—NH—CO—$CH_2$—N($CH_2$COOH)—$SO_2$—,
—$CH_2$—NH—CO—$CH_2$—N($C_6H_{13}$)—$SO_2$—,
—$CH_2$—NH—CO—$(CH_2)_{10}$—N($C_2H_5$)—$SO_2$—,
—$CH_2$—NH—CO—$CH_2$—N(—$CH_2$—$CH_2$—OH) $SO_2$—, —$CH_2$—NHCO($CH_2)_{10}$—S—$CH_2CH_2$—,
—$CH_2$NHCOCH$_2$—O—$CH_2CH_2$—, —$CH_2$NHCO $(CH_2)_{10}$—S—$CH_2CH_2$—,
—$CH_2$—$C_6H_4$—O—$CH_2CH_2$—,
—$CH_2$O—$CH_2$—C($CH_2$—O$CH_2CH_2$—$C_6F_{13}$)$_2$—$Ch_2$—O$CH_2$—$CH_2$—,
—$CH_2$NHCOCH$_2$CH$_2$CON—$CH_2CH_2$NHCOCH$_2$N $(C_2H_5)SO_2C_8F_{17}$,
$CH_2$—$CH_2$NHCOCH$_2$N($C_2H_5$)—$SO_2$—
—$CH_2$—O—$CH_2$—CH(O$C_{10}H_{21}$)—$CH_2$—O—$CH_2CH_2$,
—$CH_2$—O$CH_2$C($CH_2$OH)$_2$—$CH_2$—O—$CH_2CH_2$,

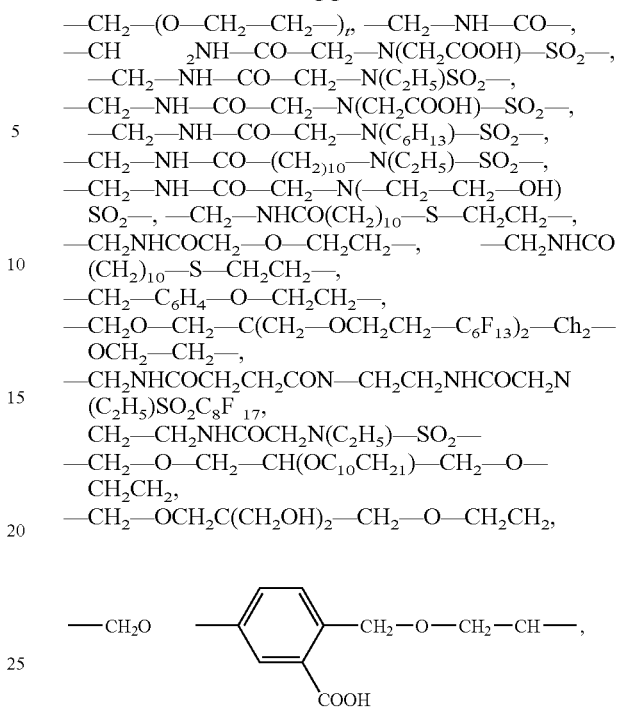

—$CH_2$NHCOCH$_2$N($C_6H_5$)—$SO_2$—,
—NHCO—$CH_2$—$CH_2$—, —NH—CO—, —NH—CO—$CH_2$—N($CH_2$COOH)—$SO_2$—,
—NH—CO—$CH_2$—N($C_2H_5$)—$SO_2$—, —NH—CO—$CH_2$—N($C_{10}H_{21}$)—$SO_2$—,
—NH—CO—$CH_2$—N($C_6H_{13}$)—$SO_2$—, —NH—CO—$(CH_2)_{10}$—N($C_2H_5$)—$SO_2$—,
—NH—CO—$CH_2$—N(—$CH_2$—$C_6H_5$)—$SO_2$—,
—NH—CO—$CH_2$—N(—$CH_2$—$CH_2$—OH)$SO_2$—,
—NH—CO—$CH_2$—, —$CH_2$—O—$C_6H_4$—O—$CH_2$—$CH_2$—, —$CH_2$—$C_6$—$H_4$—O—$CH_2$—$CH_2$—,
—N($C_5H_5$)—$SO_2$—, —N($C_{10}H_{21}$)—$SO_2$—,
—N($C_6H_{13}$)—$SO_2$—, or
—N($C_2H_4$OH)—$SO_2$—, —N($CH_2$COOH)—$SO_2$—;
s stands for numbers 3-15; and
t stands for numbers 2-6.

5. A method according to claim 1, wherein the contrast agent is gadolinium complex of 10-[2-hydroxy-4-aza-5-oxo-7-aza-7-(perfluorooctylsulfonyl)-nonyl]-1,4,7-tris (carboxymethyl)-1,4,7,10-tetraazacyclododecane; or gadolinium complex of 10-[2-hydroxy-4-aza-5-oxo-7-oxa-10,10,11,11,12,12,13,13,14,14,15,15,16,16,17,17,17-heptadecafluoroheptadecyl]-1,4,7-tris (carboxymethyl)-1,4,7,10-tetraazacyclododecane.

\* \* \* \* \*

UNITED STATES PATENT AND TRADEMARK OFFICE
CERTIFICATE OF CORRECTION

PATENT NO.        : 7,226,578 B2
APPLICATION NO. : 10/957628
DATED             : June 5, 2007
INVENTOR(S)       : Johannes Platzek et al.

It is certified that error appears in the above-identified patent and that said Letters Patent is hereby corrected as shown below:

Column 88, line 4 reads "N(CH$_2$COOH)", should read -- N(C$_{10}$H$_{21}$) --

Signed and Sealed this

Nineteenth Day of February, 2008

JON W. DUDAS
*Director of the United States Patent and Trademark Office*